(12) United States Patent
Deckers et al.

(10) Patent No.: US 7,585,645 B2
(45) Date of Patent: *Sep. 8, 2009

(54) THIOREDOXIN AND THIOREDOXIN REDUCTASE CONTAINING OIL BODY BASED PRODUCTS

(75) Inventors: Harm M. Deckers, Calgary (CA); Gijs van Rooijen, Calgary (CA); Joseph Boothe, Calgary (CA); Janis Goll, Calgary (CA); Maurice M. Moloney, Calgary (CA); Bipin K. Dalmia, San Diego, CA (US)

(73) Assignee: Sembiosys Genetics Inc., Alberta (CA)

( * ) Notice: Subject to any disclaimer, the term of this patent is extended or adjusted under 35 U.S.C. 154(b) by 86 days.

This patent is subject to a terminal disclaimer.

(21) Appl. No.: 09/897,898

(22) Filed: Jul. 5, 2001

(65) Prior Publication Data

US 2002/0037303 A1    Mar. 28, 2002

Related U.S. Application Data

(63) Continuation-in-part of application No. 09/448,755, filed on Nov. 24, 1999, now abandoned.

(60) Provisional application No. 60/109,997, filed on Nov. 25, 1998.

(51) Int. Cl.
| | |
|---|---|
| C12P 21/04 | (2006.01) |
| A23J 1/00 | (2006.01) |
| C12N 15/00 | (2006.01) |
| C12N 5/00 | (2006.01) |
| A61K 38/00 | (2006.01) |
| C07H 21/04 | (2006.01) |
| C07K 1/00 | (2006.01) |
| C12N 5/04 | (2006.01) |
| C12N 9/00 | (2006.01) |

(52) U.S. Cl. .............. 435/69.1; 435/69.7; 435/440; 435/320.1; 435/183; 435/410; 435/419; 435/415; 435/416; 530/412; 530/350; 530/300; 536/23.2; 536/23.4

(58) Field of Classification Search ............... 424/401; 435/189, 325, 252.3, 69.7, 69.4, 468, 410, 435/419, 416, 412, 320.1, 69.1, 440, 195, 435/71.1, 4, 6, 186; 536/23.1, 23.2, 23.4, 536/23.7, 23.6; 530/320, 350, 412

See application file for complete search history.

(56) References Cited

U.S. PATENT DOCUMENTS

| | | | |
|---|---|---|---|
| 3,971,856 A | 7/1976 | Daftary | |
| 4,025,658 A | 5/1977 | Pominski et al. | |
| 4,088,795 A | 5/1978 | Goodnight, Jr. et al. | |
| 4,362,759 A | 12/1982 | Harris | |
| 4,771,036 A | 9/1988 | Pigiet et al. | |
| 4,935,231 A | 6/1990 | Pigiet | |
| 5,260,203 A | 11/1993 | Ladner et al. | |
| 5,444,041 A * | 8/1995 | Owen et al. | 514/2 |
| 5,602,183 A | 2/1997 | Martin et al. | |
| 5,643,583 A | 7/1997 | Voultoury et al. | |
| 5,646,016 A * | 7/1997 | McCoy et al. | 435/69.7 |
| 5,650,554 A | 7/1997 | Moloney | |
| 5,683,710 A | 11/1997 | Akemi et al. | |
| 5,683,740 A | 11/1997 | Voultoury et al. | |
| 5,763,733 A | 6/1998 | Whitlow et al. | |
| 5,767,260 A | 6/1998 | Whitlow et al. | |
| 5,792,506 A | 8/1998 | Buchanan et al. | |
| 5,856,452 A | 1/1999 | Moloney et al. | |
| 6,146,645 A * | 11/2000 | Deckers et al. | 424/401 |
| 6,183,762 B1 * | 2/2001 | Deckers et al. | 424/401 |
| 6,582,710 B2 * | 6/2003 | Deckers et al. | 424/401 |
| 6,596,287 B2 * | 7/2003 | Deckers et al. | 424/401 |
| 6,599,513 B2 * | 7/2003 | Deckers et al. | 424/401 |
| 6,761,914 B2 * | 7/2004 | Deckers et al. | 424/776 |
| 2002/0088025 A1 * | 7/2002 | Moloney et al. | 800/288 |

FOREIGN PATENT DOCUMENTS

| | | |
|---|---|---|
| EP | 0 475 160 | 8/1991 |
| EP | 0 550 162 A1 * | 7/1993 |
| EP | 0 680 751 A1 * | 4/1995 |
| JP | 9012471 A2 | 1/1997 |
| JP | 1129785 A2 | 10/1999 |
| JP | 103743 A2 | 4/2000 |
| WO | WO 91/04320 | 4/1991 |
| WO | WO 93/07278 | 4/1993 |
| WO | WO 93/21320 * | 10/1993 |
| WO | WO 96/21029 | 7/1996 |
| WO | WO 96/41543 | 12/1996 |
| WO | WO 97/02352 | 1/1997 |
| WO | WO 98/27115 | 6/1998 |
| WO | WO 98/53698 | 12/1998 |
| WO | WO99/20122 | 4/1999 |
| WO | WO 00/30602 | 6/2000 |
| WO | WO 00/36126 | 6/2000 |
| WO | WO 00/44781 | 8/2000 |
| WO | WO00/58352 | 10/2000 |

OTHER PUBLICATIONS

Loer et al. Plant Phsiol. (1993) 101:993-998.*

(Continued)

*Primary Examiner*—Yong D Pak
(74) *Attorney, Agent, or Firm*—Stephen A. Bent; Foley & Lardner LLP

(57) ABSTRACT

The present invention provides novel emulsion formulations which comprise oil bodies. The invention also provides a method for preparing the emulsions and the use of the emulsions in a variety of products including food products, personal care products and pharmaceutical products. In a preferred embodiment the emulsions comprise thioredoxin and/or thioredoxin reductase.

6 Claims, 30 Drawing Sheets

OTHER PUBLICATIONS

Wieles et al. Unique gene organization of thioredoxin and thioredoxin reductase in Mycobacterium leprae.*
NiceZyme: EC 1.8.1.9.*
Millichip, M., et al., "Purification and characterization of oil-bodies (oleosomes) and oil-body boundary proteins (oleosins) from the developing cotyledons of sunflower (*Helianthus annuus L.*)", 1996, Biochemistry Journal, 314, pp. 333-337.
Murphy, D.J. and Cummins I., "Seed Oil-Bodies: Isolation, Composition and Role of Oil-Body Apolipoproteins", 1989, Phytochemistry, vol. 28, No. 8, pp. 2063-2069.
Murphy, D.J., "Structure and function of oleosins in oil plants", 1993, INFORM, vol. 4, No. 8, pp. 922-932.
Chen et al., "Enhancement of Skin Penetration", Novel Cosmetic Delivery, Marcel Dekker, Inc. New York pp. 51-69.
Huang, "Oil Bodies and Oleosins in Seeds", Annu. Rev. Plant Mol. Biol., 1992, 43:177-200.
T. J. Jakes et al., "Isolation and physicochemical characterization of the half-unit membranes of oilseed lipid Bodies", J. of the Amer. Oil Soc. vol. 67(6):353-361, 1990.
S. Nacht, "Encapsulation and Other topical delivery systems" Cosmetics & Toiletries Magz. vol. 110:25-30, Sep. 1995.
Aguilar et al., 1991, Journal of Texture studies 22(1):59-84.
Alting-Mees et al., 2000, IBC's Annual International Conf. on Antibody Engineering, Poster #1.
Aota et al., 1996, J. Cardiov, Pharmacol., 27:727-732.
Armentia et al., 1993., Clin. Exp. Allergy 23:410-415.
Bower et al. Plant Cell 8:1641-1650.
Cater et al., 1974, J. Am. Oil Chem. Soc. 51:137-141.
Cater et al., 1997, J. Am. Oil Chemists' Soc., 54:90A-93A.
Carugo et al., 1997, Proteins 28:10-28.
Chen et al, 1999, Plant Cell Physiol. 40(10):1079-1086.
Davies, P.L. et al. 1990, FASEB J. 4: 2460-2468.
Del Val et al., 1999, J. Allerg. Clin. Immunol. 103:690-697.
Galkin et al., 1997, Protein Eng. 10:687-690.
Gautier et al., 1998, Eur. J. Biochem. 252(2):314-324.
Hatzopoulos et al. 1990, Plant Cell, vol. 2, 457-467.
Hoeoeg et al., 1984, Biosci. Rep., 4:917-923.
Holbrook et al., Plant Physiol., 1991, 97: 1051-1058.
Holmberg et al., 1999, Protein Eng. 12:851-856.
Hotta et al., J. Exp. Med. 188:1445-1451.
Huang, 1992, Ann. Rev. Plant. Mol. Biol. 43:177-200.
Hurley et la., 1996, Biochemistry 35:5670-5678.
Ishiwatari et al., 1995, Planta 195:456-463.
Jacks, T. J. et al., 1990, JAOCS, 67(6): 353-361.
Jiao, J. et al., 1992, J. Agric. Food Chem. 40:2333-2336.
Johnson et al., 1984, J. of Bact. vol. 158, 3:1061-1069.
Knauf, V. C., 1994, Fat. Sci. Techn. 96:408.
Kobrehel et al., 1994, Gluten Proteins:Asso. of Cereal Research; Detmold, Germany.
Kumar et al., 1995, INFORM 6 (11):1217-1240.
Lawhon et al., 1977, J. Am. Oil, Chem. Soc. 54:75-80.
Leber R. et al., 1994, Yeast 10: 1421-1428.
Lee and Huang, 1991, Plant Physiol. 96:1395-1397.
Luthman et al., 1982, Biochemistry, vol. 21, 26:6628-2233.
MacNee et al., 1999, Am. J. Respir. Crit. Care Med. 160:S58-S65.
MacNee, 2000, Chest, 117:3035-3175.
Marty et al., 1991, Plant Mol. Biol. 17:143-148.
Millichip, M., et al., 1996, Biochemistry Journal, 31:333-337.
Monsalve et al., 1997, Clin. Exp. Allergy 27: 833-841.
Murphy, D. J. and Cummins I., 1989, Phytochemistry, 28: 2063-2069.
Murphy, D.J., 1993, INFORM, 4(8):922-932.
Naested et al., 2000, Plant Mol. Biol. 44(4):463-476.
Ogawa et al. 1993, Biosci. Biotechnol. Biochem., 57(6):1030-1033.
Pieper-Fürst et al., 1994, J. Bacterol. 176: 4328-4337.
Qu and Huang, 1990, J. Biol. Chem. vol. 265, 4:2238-2243.
Rivera-Madrid, 1995, Proc. Natl. Acad. Sci. 92:5620-5624.
Ross et al., Plant Science, 1993, 93:203-210.
Roessler, P.G., 1988, J. Physiol. (London) 24: 394-400.
Russel et al., 1988, J. Biol. Chem. 263:9015-9019.
Shi et al., 1996, Plant Mol. Biol. 32:653-662.
Shiraishi et al. , 1998, Arch. Biochem. Biophys. 358: 104-115.
Terashima et al. 1999, DNA Seq. 10(3):203-205.
Ting et al., 1997, Journal Biol. Chem. 272(6):3699-3706.
van Rooijen et al., 1991, Plant Mol. Bio. 18:1177-1179.
van Rooijen and Moloney, 1995, Plant Physiol. 109:1353-1361.
Wong et al., 1993, J. Cereal Chem. 70:113-114.
Romanowski et al., "Stability testing of cosmetic products"., Marcek Dekker, Inc. New York pp. 115-130.

* cited by examiner

FIGURE 3

ClustalW Formatted Alignments

FIGURE 4

```
  1 ATG AAT GGT CTC GAA ACT CAC AAC ACA AGG CTC TGT ATC GTA GGA AGT GGC CCA GCG GCA   60
  1  M   N   G   L   E   T   H   N   T   R   L   C   I   V   G   S   G   P   A   A    20

61 CAC ACG GCG GCG ATT TAC GCA GCT AGG GCT GAA CTT AAA CCT CTT CTC TTC GAA GGA TGG  120
 21  H   T   A   A   I   Y   A   A   R   A   E   L   K   P   L   L   F   E   G   W    40

121 ATG GCT AAC GAC ATC GCT CCC GGT GGT CAA CTA ACA ACC ACC ACC GAC GTC GAG AAT TTC  180
 41  M   A   N   D   I   A   P   G   G   Q   L   T   T   T   D   V   E   N   F        60

181 CCC GGA TTT CCA GAA GGT ATT CTC GGA GTA GAG CTC ACT GAC AAA TTC CGT AAA CAA TCG  240
 61  P   G   F   P   E   G   I   L   G   V   E   L   T   D   K   F   R   K   Q   S    80

241 GAG CGA TTC GGT ACT ACG ATA TTT ACA GAG ACG GTG ACG AAA GTC GAT TTC TCT TCG AAA  300
 81  E   R   F   G   T   T   I   F   T   E   T   V   T   K   V   D   F   S   S   K   100

301 CCG TTT AAG CTA TTC ACA GAT TCA AAA GCC ATT CTC GCT GAC GCT GTG ATT CTC GCT ACT  360
101  P   F   K   L   F   T   D   S   K   A   I   L   A   D   A   V   I   L   A   T   120

361 GGA GCT GTG GCT AAG CGG CTT AGC TTC GTT GGA TCT GGT GAA GGT TCT GGA GGT TTC TGG  420
121  G   A   V   A   K   R   L   S   F   V   G   S   G   E   G   S   G   G   F   W   140

421 AAC CGT GGA ATC TCC GCT TGT GCT GTT TGC GAC GGA GCT GCT CCG ATA TTC CGT AAC AAA  480
141  N   R   G   I   S   A   C   A   V   C   D   G   A   A   P   I   F   R   N   K   160

481 CCT CTT GCG GTG ATC GGT GGA GGC GAT TCA GCA ATG GAA GAA GCA AAC TTT CTT ACA AAA  540
161  P   L   A   V   I   G   G   G   D   S   A   M   E   E   A   N   F   L   T   K   180

541 TAT GGA TCT AAA GTG TAT ATA ATC CAT AGG AGA GAT GCT TTT AGA GCG TCT AAG ATT ATG  600
181  Y   G   S   K   V   Y   I   I   H   R   R   D   A   F   R   A   S   K   I   M   200

601 CAG CAG CGA GCT TTG TCT AAT CCT AAG ATT GAT GTG ATT TGG AAC TCG TCT GTT GTG GAA  660
201  Q   Q   R   A   L   S   N   P   K   I   D   V   I   W   N   S   S   V   V   E   220

661 GCT TAT GGA GAT GGA GAA AGA GAT GTG CTT GGA GGA TTG AAA GTG AAG AAT GTG GTT ACC  720
221  A   Y   G   D   G   E   R   D   V   L   G   G   L   K   V   K   N   V   V   T   240

721 GGA GAT GTT TCT GAT TTA AAA GTT TCT GGA TTG TTC TTT GCT ATT GGT CAT GAG CCA GCT  780
241  G   D   V   S   D   L   K   V   S   G   L   F   F   A   I   G   H   E   P   A   260

781 ACC AAG TTT TTG GAT GGT GGT GTT GAG TTA GAT TCG GAT GGT TAT GTT GTC ACG AAG CCT  840
261  T   K   F   L   D   G   G   V   E   L   D   S   D   G   Y   V   V   T   K   P   280

841 GGT ACT ACA CAG ACT AGC GTT CCC GGA GTT TTC GCT GCG GCT CAT GTT CAG GAT AAG AAG  900
281  G   T   T   Q   T   S   V   P   G   V   F   A   A   A   H   V   Q   D   K   K   300

901 TAT AGG CAA GCC ATC ACT GCT GCA GGA ACT GGG TGC ATG GCA GCT TTG GAT GCA GAG CAT  960
301  Y   R   Q   A   I   T   A   A   G   T   G   C   M   A   A   L   D   A   E   H   320

961 TAC TTA CAA GAG ATT GGA TCT CAG CAA GGT AAG AGT GAT TGA                          1002
321  Y   L   Q   E   I   G   S   Q   Q   G   K   S   D   *                            334
```

FIGURE 5

ClustalW Formatted Alignments

```
                          10            20            30            40            50            60
Translation of ATTHIREDB  MNGLETHNTRLCIVGSGPAAHIAAIYAARAELKPLLPEGWMANDIAPGGQLN Q P P - R ENP
Translation of TR         MNGLETHNTRLCIVGSGPAAHIAAIYAARAELKPLLPEGWMANDIAPGGQLT T T T D V ENP 70            80            90           100           110           120
Translation of ATTHIREDB  PGFPEGILGVELTDKFRKQSERFGTTIFTETVTKVDFSSKPFKLFTDSKAILADAVILA I
Translation of TR         PGFPEGILGVELTDKFRKQSERFGTTIFTETVTKVDFSSKPFKLFTDSKAILADAVILA T 130           140           150           160           170           180
Translation of ATTHIREDB  GAVAK WLSFVGSGE L GL WNRGISACAVCDGAAPIFRNKPLAVIGGGDSAMEEANFLTK
Translation of TR         GAVAK R LSFVGSGE G S GGF WNRGISACAVCDGAAPIFRNKPLAVIGGGDSAMEEANFLTK 190           200           210           220           230           240
Translation of ATTHIREDB  YGSKVV I D RRDAFRASKIMQQRALSNPKIDVIWNSSVVEAVGDGERDVLGGLKVKNVV T
Translation of TR         YGSKVV I I H RRDAFRASKIMQQRALSNPKIDVIWNSSVVEAVGDGERDVLGGLKVKNVV T 250           260           270           280           290           300
Translation of ATTHIREDB  GDVSDLKVSGLFFAIGHEPATKFLDGGVELDSDGYVVTKPGTTQTSVPGVFAAGDVQDKK
Translation of TR         GDVSDLKVSGLFFAIGHEPATKFLDGGVELDSDGYVVTKPGTTQTSVPGVFAAGDVQDKK 310           320           330           340           350           360
Translation of ATTHIREDB  YRQAITAAGTGCMAALDAEHYLQEIGSQQGKSD
Translation of TR         YRQAITAAGTGCMAALDAEHYLQEIGSQQGKSD
```

FIGURE 6

```
     PstI
   1 ctgcaggaattcattgtactcccagtatcattatagtgaaagttttggctctctcgccggtggttttttacctctattta    80

81 aagggttttccacctaaaaattctggtatcattctcactttacttgttactttaatttctcataatctttggttgaaat   160

161 tatcacgcttccgcacacgatatccctacaaatttattatttgttaaacatttcaaaccgcataaaatttatgaagtc   240

241 ccgtctatctttaatgtagtctaacatttccatattgaaatatataatttacttaattttagcgttggtagaaagcataa   320

321 tgatttattcttattcttcttcatataaatgtttaatatacaatataaacaaattctttaccttaagaaggatttcccat   400

401 tttatattttaaaaatatatttatcaaatattttttcaaccacgtaaatctcataataataagttgtttcaaaagtaataa   480

481 aatttaactccataatttttttattcgactgatcttaaagcaacacccagtgacacaactagccattttttttctttgaat   560

561 aaaaaaatccaattatcattgtatttttttatacaatgaaaatttcaccaaacaatcatttgtggtatttctgaagcaa   640

641 gtcatgttatgcaaaattctataattcccatttgacactacggaagtaactgaagatctgcttttacatgcgagacacat   720

721 cttctaaagtaattttaataatagttactatattcaagatttcatatatcaaatactcaatattacttctaaaaaattaa   800

801 ttagatataattaaaatattacttttttaattttaagtttaattgttgaatttgtgactattgatttattattctactat   880

881 gtttaaattgttttatagatagtttaaagtaaatataagtaatgtagtagagtgttagagtgttaccctaaaccataaac   960

961 tataagatttatggtggactaattttcatatatttcttattgcttttaccttttcttggtatgtaagtccgtaactggaa  1040

1041 ttactgtgggttgccatggcactctgtggtcttttggttcatgcatggatgcttgcgcaagaaaaagacaaagaacaaag  1120

1121 aaaaagacaaaacagagagacaaaacgcaatcacacaaccaactcaaattagtcactggctgatcaagatcgccgcgtc  1200

1201 catgtatgtctaaatgccatgcaaagcaacacgtgcttaacatgcactttaaatggctcacccatctcaacccacacaca  1280

1281 aacacattgccttttcttcatcatcaccacaaccacctgtatatattcattctcttccgccacctcaatttcttcactt  1360

1361 caacacacgtcaacctgcatatgcgtgtcatcccatgcccaaatctccatgcatgttccaaccaccttctctcttatata  1440

1441 atacctataaatacctctaatatcactcacttctttcatcatccatccatccagagtactactactctactactataata  1520

1521 ccccaacccaactcatattcaatactactctact ATG GCT TCG GAA GAA GGA CAA GTG ATC GCC TGC  1587
   1                                    M   A   S   E   E   G   Q   V   I   A   C    11

1588 CAC ACC GTT GAG ACA TGG AAC GAG CAG CTT CAG AAG GCT AAT GAA TCC AAA ACT CTT GTG  1647
  12 H   T   V   E   T   W   N   E   Q   L   Q   K   A   N   E   S   K   T   L   V    31

1648 GTG GTT GAT TTC ACG GCT TCT TGG TGT GGA CCA TGT CGT TTC ATC GCT CCA TTC TTT GCT  1707
  32 V   V   D   F   T   A   S   W   C   G   P   C   R   F   I   A   P   F   F   A    51

1708 GAT TTG GCT AAG AAA CTT CCT AAC GTG CTT TTC CTC AAG GTT GAT ACT GAT GAA TTG AAG  1767
  52 D   L   A   K   K   L   P   N   V   L   F   L   K   V   D   T   D   E   L   K    71
```

FIGURE 6 (CONT'D)

```
1768 TCG GTG GCA AGT GAT TGG GCG ATA CAG GCG ATG CCA ACC TTC ATG TTT TTG AAG GAA GGG 1827
 72   S   V   A   S   D   W   A   I   Q   A   M   P   T   F   M   F   L   K   E   G   91

1828 AAG ATT TTG GAC AAA GTT GTT GGA GCC AAG AAA GAT GAG CTT CAG TCT ACC ATT GCC AAA 1887
 92   K   I   L   D   K   V   V   G   A   K   K   D   E   L   Q   S   T   I   A   K  111
                   HindIII
1888 CAC TTG GCT TAA gcttaataagtatgaactaaaatgcatgtaggtgtaagagctcatggagagcatggaatattgt 1963
112   H   L   A   *                                                                   115

1964 atccgaccatgtaacagtataataactgagctccatctcacttcttctatgaataaacaaaggatgttatgatatattaa 2043

2044 cactctatctatgcaccttattgttctatgataaatttcctcttattattataaatcatctgaatcgtgacggcttatgg 2123

2124 aatgcttcaaatagtacaaaaacaaatgtgtactataagactttctaaacaattctaactttagcattgtgaacgagaca 2203

2204 taagtgttaagaagacataacaattataatggaagaagtttgtctccatttatatattatatattacccacttatgtatt 2283

2284 atattaggatgttaaggagacataacaattataaagagagaagtttgtatccatttatatattatatactacccatttat 2363

2364 atattatacttatccacttatttaatgtctttataaggtttgatccatgatatttctaatattttagttgatatgtatat 2443

2444 gaaagggtactatttgaactctcttactctgtataaaggttggatcatccttaaagtgggtctatttaatttattgctt 2523

2524 cttacagataaaaaaaaaattatgagttggtttgataaaatattgaaggatttaaaataataataaataataaataacat 2603

2604 ataatatatgtatataaatttattataatataacatttatctataaaaaagtaaatattgtcataaatctatacaatcgt 2683

2684 ttagccttgctggacgactctcaattatttaaacgagagtaaacatatttgacttttggttatttaacaaattattatt 2763

2764 taacactatatgaaatttttttttttatcggcaaggaaataaaattaaattaggagggacaatggtgtgtcccaatcct 2843

2844 tatacaaccaacttccacaggaaggtcaggtcggggacaacaaaaaaacaggcaagggaaatttttttaatttgggttgtc 2923

2924 ttgtttgctgcataatttatgcagtaaaacactacacataaccctttttagcagtagagcaatggttgaccgtgtgcttag 3003

3004 cttcttttatttttatttttttatcagcaaagaataaataaaataaaatgagacacttcagggatgtttcaacccttatac 3083

3084 aaaccccaaaaacaagtttcctagcaccctaccaactaaggtacc                                        3129
                                          KpnI
```

FIGURE 7

```
     PstI
   1 ctgcaggaattcattgtactcccagtatcattatagtgaaagttttggctctctcgccggtggttttttacctctattta  80

81 aagggttttccacctaaaaattctggtatcattctcactttacttgttactttaatttctcataatctttggttgaaat  160

161 tatcacgcttccgcacacgatatccctacaaatttattatttgttaaacattttcaaaccgcataaaatttatgaagtc  240

241 ccgtctatctttaatgtagtctaacattttcatattgaaatatataatttacttaattttagcgttggtagaaagcataa  320

321 tgatttattcttattcttcttcatataaatgtttaatatacaatataaacaaattctttaccttaagaaggatttcccat  400

401 tttatattttaaaaatatatttatcaaatattttttcaaccacgtaaatctcataataataagttgtttcaaaagtaataa  480

481 aatttaactccataatttttttattcgactgatcttaaagcaacacccagtgacacaactagccatttttttctttgaat  560

561 aaaaaaatccaattatcattgtatttttttatacaatgaaaatttcaccaaacaatcatttgtggtatttctgaagcaa  640

641 gtcatgttatgcaaaattctataattcccatttgacactacggaagtaactgaagatctgcttttacatgcgagacacat  720

721 cttctaaagtaatttaataatagttactatattcaagatttcatatatcaaatactcaatattacttctaaaaaattaa  800

801 ttagatataattaaaatattacttttttaattttaagtttaattgttgaatttgtgactattgatttattattctactat  880

881 gtttaaattgttttatagatagtttaaagtaaatataagtaatgtagtagagtgttagagtgttaccctaaaccataaac  960

961 tataagatttatggtggactaattttcatatatttcttattgcttttacctttcttggtatgtaagtccgtaactggaa  1040

1041 ttactgtgggttgccatggcactctgtggtcttttggttcatgcatggatgcttgcgcaagaaaaagacaaagaacaaag  1120

1121 aaaaagacaaaacagagagacaaaacgcaatcacacaaccaactcaaattagtcactggctgatcaagatcgccgcgtc  1200

1201 catgtatgtctaaatgccatgcaaagcaacacgtgcttaacatgcactttaaatggctcacccatctcaaccacacaca  1280

1281 aacacattgccttttcttcatcatcaccacaaccacctgtatatattcattctcttccgccacctcaatttcttcactt  1360

1361 caacacacgtcaacctgcatatgcgtgtcatcccatgcccaaatctccatgcatgttccaaccaccttctctcttatata  1440

1441 atacctataaatacctctaatatcactcacttctttcatcatccatccatccagagtactactactctactactataata  1520

1521 ccccaacccaactcatattcaatactactctact ATG GCG GAT ACA GCT AGA GGA ACC CAT CAC GAT  1587
   1                                    M   A   D   T   A   R   G   T   H   H   D    11

1588 ATC ATC GGC AGA GAC CAG TAC CCG ATG ATG GGC CGA GAC CGA GAC CAG TAC CAG ATG TCC  1647
  12  I   I   G   R   D   Q   Y   P   M   M   G   R   D   R   D   Q   Y   Q   M   S   31

1648 GGA CGA GGA TCT GAC TAC TCC AAG TCT AGG CAG ATT GCT AAA GCT GCA ACT GCT GTC ACA  1707
  32  G   R   G   S   D   Y   S   K   S   R   Q   I   A   K   A   A   T   A   V   T   51

1708 GCT GGT GGT TCC CTC CTT GTT CTC TCC AGC CTT ACC CTT GTT GGA ACT GTC ATA GCT TTG  1767
  52  A   G   G   S   L   L   V   L   S   S   L   T   L   V   G   T   V   I   A   L   71
```

FIGURE 7 (CONT'D)

```
1768 ACT GTT GCA ACA CCT CTG CTC GTT ATC TTC AGC CCA ATC CTT GTC CCG GCT CTC ATC ACA 1827
  72 T   V   A   T   P   L   L   V   I   F   S   P   I   L   V   P   A   L   I   T    91

1828 GTT GCA CTC CTC ATC ACC GGT TTT CTT TCC TCT GGA GGG TTT GGC ATT GCC GCT ATA ACC 1887
  92 V   A   L   L   I   T   G   F   L   S   S   G   G   F   G   I   A   A   I   T   111

1888 GTT TTC TCT TGG ATT TAC AA gtaagcacacatttatcatcttacttcataatttTgtgcaatatgtgcatgca 1960
 112 V   F   S   W   I   Y   K                                                         118

1961 tgtgttgagccagtagctttggatcaattttTTTtggtcgaataacaaatgtaacaataagaaattgcaaattctagggaa 2040

2041 catttggttaactaaatacgaaatttgacctagctagcttgaatgtgtctgtgtatatcatctatataggtaaaatgctt 2120

2121 ggtatgataccTattgattgtgaatag G TAC GCA ACG GGA GAG CAC CCA CAG GGA TCA GAC AAG 2184
 119                               Y   A   T   G   E   H   P   Q   G   S   D   K   130

2185 TTG GAC AGT GCA AGG ATG AAG TTG GGA AGC AAA GCT CAG GAT CTG AAA GAC AGA GCT CAG 2244
 131 L   D   S   A   R   M   K   L   G   S   K   A   Q   D   L   K   D   R   A   Q   150

2245 TAC TAC GGA CAG CAA CAT ACT GGT GGG GAA CAT GAC CGT GAC CGT ACT CGT GGT GGC CAG 2304
 151 Y   Y   G   Q   Q   H   T   G   G   E   H   D   R   D   R   T   R   G   G   Q   170
                         NcoI
2305 CAC ACT ACC ATG GCT TCG GAA GAA GGA CAA GTG ATC GCC TGC CAC ACC GTT GAG ACA TGG 2364
 171 H   T   T   M   A   S   E   E   G   Q   V   I   A   C   H   T   V   E   T   W   190

2365 AAC GAG CAG CTT CAG AAG GCT AAT GAA TCC AAA ACT CTT GTG GTG GTT GAT TTC ACG GCT 2424
 191 N   E   Q   L   Q   K   A   N   E   S   K   T   L   V   V   V   D   F   T   A   210

2425 TCT TGG TGT GGA CCA TGT CGT TTC ATC GCT CCA TTC TTT GCT GAT TTG GCT AAG AAA CTT 2484
 211 S   W   C   G   P   C   R   F   I   A   P   F   F   A   D   L   A   K   K   L   230

2485 CCT AAC GTG CTT TTC CTC AAG GTT GAT ACT GAT GAA TTG AAG TCG GTG GCA AGT GAT TGG 2544
 231 P   N   V   L   F   L   K   V   D   T   D   E   L   K   S   V   A   S   D   W   250

2545 GCG ATA CAG GCG ATG CCA ACC TTC ATG TTT TTG AAG GAA GGG AAG ATT TTG GAC AAA GTT 2604
 251 A   I   Q   A   M   P   T   F   M   F   L   K   E   G   K   I   L   D   K   V   270

2605 GTT GGA GCC AAG AAA GAT GAG CTT CAG TCT ACC ATT GCC AAA CAC TTG GCT TAA gcttaata 2666
 271 V   G   A   K   K   D   E   L   Q   S   T   I   A   K   H   L   A   *            288

2667 agtatgaactaaaatgcatgtaggtgtaagagctcatggagagcatggaatattgtatccgaccatgtaacagtataata 2746

2747 actgagctccatctcacttcttctatgaataaacaaaggatgttatgatatattaacactctatctatgcaccttattgt 2826

2827 tctatgataaatttcctcttattattataaatcatctgaatcgtgacggcttatggaatgcttcaaatagtacaaaaaca 2906

2907 aatgtgtactataagactttctaaacaattctaactttagcattgtgaacgagacataagtgttaagaagacataacaat 2986

2987 tataatggaagaagtttgtctccatttatatattatatattacccacttatgtattatattaggatgttaaggagacata 3066
```

FIGURE 7 (CONT'D)

```
3067 acaattataaagagagaagtttgtatccatttatatattatatactacccatttatatattatacttatccacttattta 3146

3147 atgtctttataaggtttgatccatgatatttctaatattttagttgatatgtatatgaaagggtactatttgaactctct 3226

3227 tactctgtataaaggttggatcatccttaaagtgggtctatttaattttattgcttcttacagataaaaaaaaaattatg 3306

3307 agttggtttgataaaatattgaaggatttaaaataataataaataataaataacatataatatatgtatataaatttatt 3386

3387 ataatataacatttatctataaaaaagtaaatattgtcataaatctatacaatcgtttagccttgctggacgactctcaa 3466

3467 ttatttaaacgagagtaaacatatttgacttttggttatttaacaaattattatttaacactatatgaaattttttttt 3546

3547 tttatcggcaaggaaataaaattaaattaggagggacaatggtgtgtcccaatccttatacaaccaacttccacaggaag 3626

3627 gtcaggtcggggacaacaaaaaaacaggcaagggaaattttttaatttgggttgtcttgtttgctgcataaatttatgcag 3706

3707 taaaacactacacataacccttttagcagtagagcaatggttgaccgtgtgcttagcttcttttatttttatttttttatc 3786

3787 agcaaagaataaataaaataaaatgagacacttcagggatgtttcaacccttatacaaaaccccaaaaacaagtttccta 3866

3867 gcaccctaccaactaaggtacc                                                          3888
                       KpnI
```

FIGURE 8

```
      PstI
   1  ctgcaggaattcattgtactcccagtatcattatagtgaaagttttggctctctcgccggtggttttttacctctattta  80

81  aagggttttccacctaaaaattctggtatcattctcacttttacttgttactttaatttctcataatctttggttgaaat  160

161  tatcacgcttccgcacacgatatccctacaaatttattatttgttaaacattttcaaaccgcataaaatttatgaagtc  240

241  ccgtctatctttaatgtagtctaacattttcatattgaaatatataatttacttaattttagcgttggtagaaagcataa  320

321  tgatttattcttattcttcttcatataaatgtttaatatacaatataaacaaattctttaccttaagaaggatttcccat  400

401  tttatattttaaaaatatatttatcaaatattttttcaaccacgtaaatctcataataataagttgtttcaaaagtaataa  480

481  aatttaactccataatttttttattcgactgatcttaaagcaacacccagtgacacaactagccatttttttctttgaat  560

561  aaaaaaatccaattatcattgtattttttttatacaatgaaaatttcaccaaacaatcatttgtggtatttctgaagcaa  640

641  gtcatgttatgcaaaattctataattcccatttgacactacggaagtaactgaagatctgcttttacatgcgagacacat  720

721  cttctaaagtaattttaataatagttactatattcaagatttcatatatcaaatactcaatattacttctaaaaaattaa  800

801  ttagatataattaaaatattacttttttaattttaagtttaattgttgaatttgtgactattgatttattattctactat  880

881  gtttaaattgttttatagatagtttaaagtaaatataagtaatgtagtagagtgttagagtgttaccctaaaccataaac  960

961  tataagatttatggtggactaattttcatatatttcttattgcttttacctttttcttggtatgtaagtccgtaactggaa  1040

1041  ttactgtgggttgccatggcactctgtggtcttttggttcatgcatggatgcttgcgcaagaaaaagacaaagaacaaag  1120

1121  aaaaaagacaaaacagagagacaaaacgcaatcacacaaccaactcaaattagtcactggctgatcaagatcgccgcgtc  1200

1201  catgtatgtctaaatgccatgcaaagcaacacgtgcttaacatgcactttaaatggctcacccatctcaacccacacaca  1280

1281  aacacattgccttttcttcatcatcaccacaaccacctgtatatattcattctcttccgccacctcaatttcttcactt  1360

1361  caacacacgtcaacctgcatatgcgtgtcatcccatgcccaaatctccatgcatgttccaaccaccttctctcttatata  1440

1441  atacctataaatacctctaatatcactcacttctttcatcatccatccatccagagtactactactctactactataata  1520

1521  ccccaacccaactcatattcaatactactctact ATG GCT TCG GAA GAA GGA CAA GTG ATC GCC TGC    1587
   1                                       M   A   S   E   E   G   Q   V   I   A   C    11

1588  CAC ACC GTT GAG ACA TGG AAC GAG CAG CTT CAG AAG GCT AAT GAA TCC AAA ACT CTT GTG    1647
  12  H   T   V   E   T   W   N   E   Q   L   Q   K   A   N   E   S   K   T   L   V    31

1648  GTG GTT GAT TTC ACG GCT TCT TGG TGT GGA CCA TGT CGT TTC ATC GCT CCA TTC TTT GCT    1707
  32  V   V   D   F   T   A   S   W   C   G   P   C   R   F   I   A   P   F   F   A    51

1708  GAT TTG GCT AAG AAA CTT CCT AAC GTG CTT TTC CTC AAG GTT GAT ACT GAT GAA TTG AAG    1767
  52  D   L   A   K   K   L   P   N   V   L   F   L   K   V   D   T   D   E   L   K    71
```

FIGURE 8 (CONT'D)

```
1768 TCG GTG GCA AGT GAT TGG GCG ATA CAG GCG ATG CCA ACC TTC ATG TTT TTG AAG GAA GGG 1827
  72 S   V   A   S   D   W   A   I   Q   A   M   P   T   F   M   F   L   K   E   G    91

1828 AAG ATT TTG GAC AAA GTT GTT GGA GCC AAG AAA GAT GAG CTT CAG TCT ACC ATT GCC AAA 1887
  92 K   I   L   D   K   V   V   G   A   K   K   D   E   L   Q   S   T   I   A   K   111

1888 CAC TTG GCT ATG GCG GAT ACA GCT AGA GGA ACC CAT CAC GAT ATC ATC GGC AGA GAC CAG 1947
 112 H   L   A   M   A   D   T   A   R   G   T   H   H   D   I   I   G   R   D   Q   131

1948 TAC CCG ATG ATG GGC CGA GAC CGA GAC CAG TAC CAG ATG TCC GGA CGA GGA TCT GAC TAC 2007
 132 Y   P   M   M   G   R   D   R   D   Q   Y   Q   M   S   G   R   G   S   D   Y   151

2008 TCC AAG TCT AGG CAG ATT GCT AAA GCT GCA ACT GCT GTC ACA GCT GGT GGT TCC CTC CTT 2067
 152 S   K   S   R   Q   I   A   K   A   A   T   A   V   T   A   G   G   S   L   L   171

2068 GTT CTC TCC AGC CTT ACC CTT GTT GGA ACT GTC ATA GCT TTG ACT GTT GCA ACA CCT CTG 2127
 172 V   L   S   S   L   T   L   V   G   T   V   I   A   L   T   V   A   T   P   L   191

2128 CTC GTT ATC TTC AGC CCA ATC CTT GTC CCG GCT CTC ATC ACA GTT GCA CTC CTC ATC ACC 2187
 192 L   V   I   F   S   P   I   L   V   P   A   L   I   T   V   A   L   L   I   T   211

2188 GGT TTT CTT TCC TCT GGA GGG TTT GGC ATT GCC GCT ATA ACC GTT TTC TCT TGG ATT TAC 2247
 212 G   F   L   S   S   G   G   F   G   I   A   A   I   T   V   F   S   W   I   Y   231

2248 AA gtaagcacacatttatcatcttacttcataatttttgtgcaatatgtgcatgcatgtgttgagccagtagctttggat 2326
 232 K                                                                                232

2327 caatttttttggtcgaataacaaatgtaacaataagaaattgcaaattctagggaacatttggttaactaaatacgaaat 2406

2407 ttgacctagctagcttgaatgtgtctgtgtatatcatctatataggtaaaatgcttggtatgatacctattgattgtgaa 2486

2487 tag G TAC GCA ACG GGA GAG CAC CCA CAG GGA TCA GAC AAG TTG GAC AGT GCA AGG ATG 2544
 233     Y   A   T   G   E   H   P   Q   G   S   D   K   L   D   S   A   R   M   250

2545 AAG TTG GGA AGC AAA GCT CAG GAT CTG AAA GAC AGA GCT CAG TAC TAC GGA CAG CAA CAT 2604
 251 K   L   G   S   K   A   Q   D   L   K   D   R   A   Q   Y   Y   G   Q   Q   H   270
                                                                              HindIII
2605 ACT GGT GGG GAA CAT GAC CGT GAC CGT ACT CGT GGT GGC CAG CAC ACT ACT TAA gcttaata 2666
 271 T   G   G   E   H   D   R   D   R   T   R   G   G   Q   H   T   T   *           288

2667 agtatgaactaaaatgcatgtaggtgtaagagctcatggagagcatggaatattgtatccgaccatgtaacagtataata 2746

2747 actgagctccatctcacttcttctatgaataaacaaggatgttatgatatattaacactctatctatgcaccttattgt 2826

2827 tctatgataaatttcctcttattattataaatcatctgaatcgtgacggcttatggaatgcttcaaatagtacaaaaaca 2906

2907 aatgtgtactataagactttctaaacaattctaactttagcattgtgaacgagacataagtgttaagaagacataacaat 2986

2987 tataatggaagaagtttgtctccatttatatattatatattacccacttatgtattatattaggatgttaaggagacata 3066
```

FIGURE 8 (CONT'D)

```
3067 acaattataaagagagaagtttgtatccatttatatattatatactacccatttatatattatacttatccacttattta 3146

3147 atgtctttataaggtttgatccatgatatttctaatattttagttgatatgtatatgaaagggtactatttgaactctct 3226

3227 tactctgtataaaggttggatcatccttaaagtgggtctatttaattttattgcttcttacagataaaaaaaaaattatg 3306

3307 agttggtttgataaaatattgaaggatttaaaataataataaataataaataacatataatatatgtatataaatttatt 3386

3387 ataatataacatttatctataaaaaagtaaatattgtcataaatctatacaatcgtttagccttgctggacgactctcaa 3466

3467 ttatttaaacgagagtaaacatatttgacttttggttatttaacaaattattatttaacactatatgaaatttttttttt 3546

3547 tttatcggcaaggaaataaaattaaattaggagggacaatggtgtgtcccaatccttatacaaccaacttccacaggaag 3626

3627 gtcaggtcggggacaacaaaaaaacaggcaagggaattttttaatttgggttgtcttgtttgctgcataatttatgcag 3706

3707 taaaacactacacataaccctttagcagtagagcaatggttgaccgtgtgcttagcttcttttatttatttttttatc 3786

3787 agcaaagaataaataaaataaaatgagacacttcagggatgtttcaacccttatacaaaaccccaaaaacaagtttccta 3866

3867 gcaccctaccaactaaggtacc                                                           3888
                    KpnI
```

FIGURE 9

```
     PstI
   1 ctgcaggaattcattgtactcccagtatcattatagtgaaagttttggctctctcgccggtggttttttacctctattta   80

81 aagggttttccacctaaaaattctggtatcattctcactttacttgttactttaatttctcataatctttggttgaaat  160

161 tatcacgcttccgcacacgatatccctacaaatttattatttgttaaacattttcaaaccgcataaaatttatgaagtc  240

241 ccgtctatctttaatgtagtctaacattttcatattgaaatatataatttacttaattttagcgttggtagaaagcataa  320

321 tgatttattcttattcttcttcatataaatgtttaatatacaatataaacaaattctttaccttaagaaggatttcccat  400

401 tttatatttaaaaatatatttatcaaatattttcaaccacgtaaatctcataataataagttgtttcaaaagtaataa   480

481 aatttaactccataattttttattcgactgatcttaaagcaacacccagtgacacaactagccattttttttctttgaat  560

561 aaaaaaatccaattatcattgtatttttttatacaatgaaaatttcaccaaacaatcatttgtggtatttctgaagcaa   640

641 gtcatgttatgcaaaattctataatcccatttgacactacggaagtaactgaagatctgcttttacatgcgagacacat   720

721 cttctaaagtaattttaataatagttactatattcaagatttcatatatcaaatactcaatattacttctaaaaaattaa   800

801 ttagatataattaaaatattacttttttaattttaagtttaattgttgaatttgtgactattgatttattattctactat   880

881 gtttaaattgttttatagatagtttaaagtaaatataagtaatgtagtagagtgttagagtgttaccctaaaccataaac  960

961 tataagatttatggtggactaattttcatatatttcttattgcttttaccttttcttggtatgtaagtccgtaactggaa 1040

1041 ttactgtgggttgccatggcactctgtggtcttttggttcatgcatggatgcttgcgcaagaaaaagacaaagaacaaag 1120

1121 aaaaaagacaaaacagagagacaaaacgcaatcacacaaccaactcaaattagtcactggctgatcaagatcgccgcgtc 1200

1201 catgtatgtctaaatgccatgcaaagcaacacgtgcttaacatgcactttaaatggctcacccatctcaacccacacaca 1280

1281 aacacattgccttttcttcatcatcaccacaaccacctgtatatattcattctcttccgccacctcaatttcttcactt 1360

1361 caacacacgtcaacctgcatatgcgtgtcatcccatgcccaaatctccatgcatgttccaaccaccttctctcttatata 1440

1441 atacctataaatacctctaatatcactcacttctttcatcatccatccatccagagtactactactctactactataata 1520

1521 ccccaacccaactcatattcaatactactctact ATG AAT GGT CTC GAA ACT CAC AAC ACA AGG CTC     1587
   1                                     M   N   G   L   E   T   H   N   T   R   L    11

1588 TGT ATC GTA GGA AGT GGC CCA GCG GCA CAC ACG GCG GCG ATT TAC GCA GCT AGG GCT GAA   1647
  12 C   I   V   G   S   G   P   A   A   H   T   A   A   I   Y   A   A   R   A   E    31

1648 CTT AAA CCT CTT CTC TTC GAA GGA TGG ATG GCT AAC GAC ATC GCT CCC GGT GGT CAA CTA   1707
  32 L   K   P   L   L   F   E   G   W   M   A   N   D   I   A   P   G   G   Q   L    51

1708 ACA ACC ACC ACC GAC GTC GAG AAT TTC CCC GGA TTT CCA GAA GGT ATT CTC GGA GTA GAG   1767
  52 T   T   T   T   D   V   E   N   F   P   G   F   P   E   G   I   L   G   V   E    71
```

FIGURE 9 (CONT'D)

```
1768 CTC ACT GAC AAA TTC CGT AAA CAA TCG GAG CGA TTC GGT ACT ACG ATA TTT ACA GAG ACG 1827
 72  L   T   D   K   F   R   K   Q   S   E   R   F   G   T   T   I   F   T   E   T    91

1828 GTG ACG AAA GTC GAT TTC TCT TCG AAA CCG TTT AAG CTA TTC ACA GAT TCA AAA GCC ATT 1887
 92  V   T   K   V   D   F   S   S   K   P   F   K   L   F   T   D   S   K   A   I   111

1888 CTC GCT GAC GCT GTG ATT CTC GCT ACT GGA GCT GTG GCT AAG CGG CTT AGC TTC GTT GGA 1947
112  L   A   D   A   V   I   L   A   T   G   A   V   A   K   R   L   S   F   V   G   131

1948 TCT GGT GAA GGT TCT GGA GGT TTC TGG AAC CGT GGA ATC TCC GCT TGT GCT GTT TGC GAC 2007
132  S   G   E   G   S   G   G   F   W   N   R   G   I   S   A   C   A   V   C   D   151

2008 GGA GCT GCT CCG ATA TTC CGT AAC AAA CCT CTT GCG GTG ATC GGT GGA GGC GAT TCA GCA 2067
152  G   A   A   P   I   F   R   N   K   P   L   A   V   I   G   G   G   D   S   A   171

2068 ATG GAA GAA GCA AAC TTT CTT ACA AAA TAT GGA TCT AAA GTG TAT ATA ATC CAT AGG AGA 2127
172  M   E   E   A   N   F   L   T   K   Y   G   S   K   V   Y   I   I   H   R   R   191

2128 GAT GCT TTT AGA GCG TCT AAG ATT ATG CAG CAG CGA GCT TTG TCT AAT CCT AAG ATT GAT 2187
192  D   A   F   R   A   S   K   I   M   Q   Q   R   A   L   S   N   P   K   I   D   211

2188 GTG ATT TGG AAC TCG TCT GTT GTG GAA GCT TAT GGA GAT GGA GAA AGA GAT GTG CTT GGA 2247
212  V   I   W   N   S   S   V   V   E   A   Y   G   D   G   E   R   D   V   L   G   231

2248 GGA TTG AAA GTG AAG AAT GTG GTT ACC GGA GAT GTT TCT GAT TTA AAA GTT TCT GGA TTG 2307
232  G   L   K   V   K   N   V   V   T   G   D   V   S   D   L   K   V   S   G   L   251

2308 TTC TTT GCT ATT GGT CAT GAG CCA GCT ACC AAG TTT TTG GAT GGT GGT GTT GAG TTA GAT 2367
252  F   F   A   I   G   H   E   P   A   T   K   F   L   D   G   G   V   E   L   D   271

2368 TCG GAT GGT TAT GTT GTC ACG AAG CCT GGT ACT ACA CAG ACT AGC GTT CCC GGA GTT TTC 2427
272  S   D   G   Y   V   V   T   K   P   G   T   T   Q   T   S   V   P   G   V   F   291

2428 GCT GCG GGT GAT GTT CAG GAT AAG AAG TAT AGG CAA GCC ATC ACT GCT GCA GGA ACT GGG 2487
292  A   A   G   D   V   Q   D   K   K   Y   R   Q   A   I   T   A   A   G   T   G   311

2488 TGC ATG GCA GCT TTG GAT GCA GAG CAT TAC TTA CAA GAG ATT GGA TCT CAG CAA GGT AAG 2547
312  C   M   A   A   L   D   A   E   H   Y   L   Q   E   I   G   S   Q   Q   G   K   331

2548 AGT GAT TGA agcttaataagtatgaactaaaatgcatgtaggtgtaagagctcatggagagcatggaatattgtatc 2624
332  S   D   *   HindIII                                                              334

2625 cgaccatgtaacagtataataactgagctccatctcacttcttctatgaataaacaaaggatgttatgatatattaacac 2704

2705 tctatctatgcaccttattgttctatgataaatttcctcttattattataaatcatctgaatcgtgacggcttatggaat 2784

2785 gcttcaaatagtacaaaaacaaatgtgtactataagactttctaaacaattctaactttagcattgtgaacgagacataa 2864

2865 gtgttaagaagacataacaattataatggaagaagtttgtctccatttatatattatatattacccacttatgtattata 2944
```

FIGURE 9 (CONT'D)

```
2945 ttaggatgttaaggagacataacaattataaagagagaagtttgtatccatttatatattatatactacccatttatata 3024

3025 ttatacttatccacttatttaatgtctttataaggtttgatccatgatatttctaatattttagttgatatgtatatgaa 3104

3105 agggtactatttgaactctcttactctgtataaaggttggatcatccttaaagtgggtctatttaattttattgcttctt 3184

3185 acagataaaaaaaaaattatgagttggtttgataaaatattgaaggatttaaaataataataaataataaataacatata 3264

3265 atatatgtatataaatttattataatataacatttatctataaaaaagtaaatattgtcataaatctatacaatcgttta 3344

3345 gccttgctggacgactctcaattatttaaacgagagtaaacatatttgacttttggttatttaacaaattattatttaa 3424

3425 cactatatgaaattttttttttttatcggcaaggaaataaaattaaattaggagggacaatggtgtgtcccaatccttat 3504

3505 acaaccaacttccacaggaaggtcaggtcggggacaacaaaaaaacaggcaagggaaattttttaatttgggttgtcttg 3584

3585 tttgctgcataatttatgcagtaaaacactacacataacccttttagcagtagagcaatggttgaccgtgtgcttagctt 3664

3665 cttttatttattttttttatcagcaaagaataaataaaataaaatgagacacttcagggatgtttcaaccccttatacaaa 3744

3745 accccaaaaacaagtttcctagcaccctaccaactaaggtacc                                       3787
                                              KpnI
```

FIGURE 10

```
     PstI
  1  ctgcaggaattcattgtactcccagtatcattatagtgaaagttttggctctctcgccggtggttttttacctctattta    80

81  aagggttttccacctaaaaattctggtatcattctcactttacttgttactttaatttctcataatctttggttgaaat    160

161  tatcacgcttccgcacacgatatccctacaaatttattatttgttaaacattttcaaaccgcataaaattttatgaagtc    240

241  ccgtctatctttaatgtagtctaacattttcatattgaaatatataatttacttaattttagcgttggtagaaagcataa    320

321  tgatttattcttattcttcttcatataaatgtttaatatacaatataaacaaattctttaccttaagaaggatttcccat    400

401  tttatattttaaaaatatatttatcaaatattttttcaaccacgtaaatctcataataataagttgtttcaaaagtaataa    480

481  aatttaactccataatttttttattcgactgatcttaaagcaacacccagtgacacaactagccatttttttctttgaat    560

561  aaaaaaatccaattatcattgtatttttttatacaatgaaaatttcaccaaacaatcatttgtggtatttctgaagcaa    640

641  gtcatgttatgcaaaattctataattcccatttgacactacggaagtaactgaagatctgcttttacatgcgagacacat    720

721  cttctaaagtaattttaataatagttactatattcaagatttcatatatcaaatactcaatattacttctaaaaaattaa    800

801  ttagatataattaaaatattacttttttaattttaagtttaattgttgaatttgtgactattgatttattattctactat    880

881  gtttaaattgttttatagatagtttaaagtaaatataagtaatgtagtagagtgttagagtgttaccctaaaccataaac    960

961  tataagatttatggtggactaattttcatatatttcttattgcttttacctttcttggtatgtaagtccgtaactggaa    1040

1041 ttactgtgggttgccatggcactctgtggtcttttggttcatgcatggatgcttgcgcaagaaaaagacaaagaacaaag    1120

1121 aaaaaagacaaaacagagagacaaaacgcaatcacacaaccaactcaaattagtcactggctgatcaagatcgccgcgtc    1200

1201 catgtatgtctaaatgccatgcaaagcaacacgtgcttaacatgcactttaaatggctcacccatctcaacccacacaca    1280

1281 aacacattgccttttcttcatcatcaccacaaccacctgtatatattcattctcttccgccacctcaatttcttcactt    1360

1361 caacacacgtcaacctgcatatgcgtgtcatcccatgcccaaatctccatgcatgttccaaccaccttctctcttatata    1440

1441 atacctataaatacctctaatatcactcacttctttcatcatccatccatccagagtactactactctactactataata    1520

1521 ccccaacccaactcatattcaatactactctact ATG GCG GAT ACA GCT AGA GGA ACC CAT CAC GAT    1587
   1                                    M   A   D   T   A   R   G   T   H   H   D     11

1588 ATC ATC GGC AGA GAC CAG TAC CCG ATG ATG GGC CGA GAC CGA GAC CAG TAC CAG ATG TCC    1647
  12  I   I   G   R   D   Q   Y   P   M   M   G   R   D   R   D   Q   Y   Q   M   S     31

1648 GGA CGA GGA TCT GAC TAC TCC AAG TCT AGG CAG ATT GCT AAA GCT GCA ACT GCT GTC ACA    1707
  32  G   R   G   S   D   Y   S   K   S   R   Q   I   A   K   A   A   T   A   V   T     51

1708 GCT GGT GGT TCC CTC CTT GTT CTC TCC AGC CTT ACC CTT GTT GGA ACT GTC ATA GCT TTG    1767
```

1768 ACT GTT GCA ACA CCT CTG CTC GTT ATC TTC AGC CCA ATC CTT GTC CCG GCT CTC ATC ACA 1827
  72 T   V   A   T   P   L   L   V   I   F   S   P   I   L   V   P   A   L   I   T    91

1828 GTT GCA CTC CTC ATC ACC GGT TTT CTT TCC TCT GGA GGG TTT GGC ATT GCC GCT ATA ACC 1887
  92 V   A   L   L   I   T   G   F   L   S   S   G   G   F   G   I   A   A   I   T   111

1888 GTT TTC TCT TGG ATT TAC AA gtaagcacacatttatcatcttacttcataatttttgtgcaatatgtgcatgca 1960
 112 V   F   S   W   I   Y   K                                                        118

1961 tgtgttgagccagtagctttggatcaattttttggtcgaataacaaatgtaacaataagaaattgcaaattctagggaa 2040

2041 catttggttaactaaatacgaaatttgacctagctagcttgaatgtgtctgtgtatatcatctatataggtaaaatgctt 2120

2121 ggtatgatacctattgattgtgaatag G TAC GCA ACG GGA GAG CAC CCA CAG GGA TCA GAC AAG      2184
 119                             Y   A   T   G   E   H   P   Q   G   S   D   K        130

2185 TTG GAC AGT GCA AGG ATG AAG TTG GGA AGC AAA GCT CAG GAT CTG AAA GAC AGA GCT CAG 2244
 131 L   D   S   A   R   M   K   L   G   S   K   A   Q   D   L   K   D   R   A   Q   150

2245 TAC TAC GGA CAG CAA CAT ACT GGT GGG GAA CAT GAC CGT GAC CGT ACT CGT GGT GGC CAG 2304
 151 Y   Y   G   Q   Q   H   T   G   G   E   H   D   R   D   R   T   R   G   G   Q   170

2305 CAC ACT ACC ATG AAT GGT CTC GAA ACT CAC AAC ACA AGG CTC TGT ATC GTA GGA AGT GGC 2364
 171 H   T   T   M   N   G   L   E   T   H   N   T   R   L   C   I   V   G   S   G   190

2365 CCA GCG GCA CAC ACG GCG GCG ATT TAC GCA GCT AGG GCT GAA CTT AAA CCT CTT CTC TTC 2424
 191 P   A   H   T   A   A   I   Y   A   A   R   A   E   L   K   P   L   L   F   210

2425 GAA GGA TGG ATG GCT AAC GAC ATC GCT CCC GGT GGT CAA CTA ACA ACC ACC ACC GAC GTC 2484
 211 E   G   W   M   A   N   D   I   A   P   G   G   Q   L   T   T   T   T   D   V   230

2485 GAG AAT TTC CCC GGA TTT CCA GAA GGT ATT CTC GGA GTA GAG CTC ACT GAC AAA TTC CGT 2544
 231 E   N   F   P   G   F   P   E   G   I   L   G   V   E   L   T   D   K   F   R   250

2545 AAA CAA TCG GAG CGA TTC GGT ACT ACG ATA TTT ACA GAG ACG GTG ACG AAA GTC GAT TTC 2604
 251 K   Q   S   E   R   F   G   T   T   I   F   T   E   T   V   T   K   V   D   F   270

2605 TCT TCG AAA CCG TTT AAG CTA TTC ACA GAT TCA AAA GCC ATT CTC GCT GAC GCT GTG ATT 2664
 271 S   S   K   P   F   K   L   F   T   D   S   K   A   I   L   A   D   A   V   I   290

2665 CTC GCT ACT GGA GCT GTG GCT AAG CGG CTT AGC TTC GTT GGA TCT GGT GAA GGT TCT GGA 2724
 291 L   A   T   G   A   V   A   K   R   L   S   F   V   G   S   G   E   G   S   G   310

2725 GGT TTC TGG AAC CGT GGA ATC TCC GCT TGT GCT GTT TGC GAC GGA GCT GCT CCG ATA TTC 2784
 311 G   F   W   N   R   G   I   S   A   C   A   V   C   D   G   A   A   P   I   F   330

2785 CGT AAC AAA CCT CTT GCG GTG ATC GGT GGA GGC GAT TCA GCA ATG GAA GAA GCA AAC TTT 2844
 331 R   N   K   P   L   A   V   I   G   G   G   D   S   A   M   E   E   A   N   F   350
```

FIGURE 10 (CONT'D)

```
2845 CTT ACA AAA TAT GGA TCT AAA GTG TAT ATA ATC CAT AGG AGA GAT GCT TTT AGA GCG TCT 2904
351  L   T   K   Y   G   S   K   V   Y   I   I   H   R   R   D   A   F   R   A   S   370

2905 AAG ATT ATG CAG CAG CGA GCT TTG TCT AAT CCT AAG ATT GAT GTG ATT TGG AAC TCG TCT 2964
371  K   I   M   Q   Q   R   A   L   S   N   P   K   I   D   V   I   W   N   S   S   390

2965 GTT GTG GAA GCT TAT GGA GAT GGA GAA AGA GAT GTG CTT GGA GGA TTG AAA GTG AAG AAT 3024
391  V   V   E   A   Y   G   D   G   E   R   D   V   L   G   G   L   K   V   K   N   410

3025 GTG GTT ACC GGA GAT GTT TCT GAT TTA AAA GTT TCT GGA TTG TTC TTT GCT ATT GGT CAT 3084
411  V   V   T   G   D   V   S   D   L   K   V   S   G   L   F   F   A   I   G   H   430

3085 GAG CCA GCT ACC AAG TTT TTG GAT GGT GGT GTT GAG TTA GAT TCG GAT GGT TAT GTT GTC 3144
431  E   P   A   T   K   F   L   D   G   G   V   E   L   D   S   D   G   Y   V   V   450

3145 ACG AAG CCT GGT ACT ACA CAG ACT AGC GTT CCC GGA GTT TTC GCT GCG GGT GAT GTT CAG 3204
451  T   K   P   G   T   T   Q   T   S   V   P   G   V   F   A   A   G   D   V   Q   470

3205 GAT AAG AAG TAT AGG CAA GCC ATC ACT GCT GCA GGA ACT GGG TGC ATG GCA GCT TTG GAT 3264
471  D   K   K   Y   R   Q   A   I   T   A   A   G   T   G   C   M   A   A   L   D   490

3265 GCA GAG CAT TAC TTA CAA GAG ATT GGA TCT CAG CAA GGT AAG AGT GAT TGA agcttaataagt 3327
491  A   E   H   Y   L   Q   E   I   G   S   Q   Q   G   K   S   D   *   HindIII     507

3328 atgaactaaaatgcatgtaggtgtaagagctcatggagagcatggaatattgtatccgaccatgtaacagtataataact 3407

3408 gagctccatctcacttcttctatgaataaacaaaggatgttatgatatattaacactctatctatgcaccttattgttct 3487

3488 atgataaatttcctcttattattataaatcatctgaatcgtgacggcttatggaatgcttcaaatagtacaaaaacaaat 3567

3568 gtgtactataagactttctaaacaattctaactttagcattgtgaacgagacataagtgttaagaagacataacaattat 3647

3648 aatggaagaagtttgtctccatttatatattatatattacccacttatgtattatattaggatgttaaggagacataaca 3727

3728 attataaagagagaagtttgtatccatttatatattatatactacccatttatatattatacttatccacttatttaatg 3807

3808 tctttataaggtttgatccatgatatttctaatatttagttgatatgtatatgaaagggtactatttgaactctcttac 3887

3888 tctgtataaaggttggatcatccttaaagtgggtctatttaatttattgcttcttacagataaaaaaaaaattatgagt 3967

3968 tggtttgataaaatattgaaggatttaaaataataataaataataaataacatataatatatgtatataaatttattata 4047

4048 ataacatttatctataaaaaagtaaatattgtcataaatctatacaatcgtttagccttgctggacgactctcaatta 4127

4128 tttaaacgagagtaaacatatttgacttttggttatttaacaaattattatttaacactatatgaaatttttttttttt 4207

4208 atcggcaaggaaataaaattaaattaggagggacaatggtgtgtcccaatccttatacaaccaacttccacaggaaggtc 4287
```

FIGURE 10 (CONT'D)

```
4288 aggtcggggacaacaaaaaaacaggcaagggaaatttttttaatttgggttgtcttgtttgctgcataatttatgcagtaa 4367

4368 aacactacacataacccttttagcagtagagcaatggttgaccgtgtgcttagcttcttttatttattttttttatcagc 4447

4448 aaagaataaataaaataaaatgagacacttcagggatgtttcaacccttatacaaaacccaaaaacaagtttcctagca 4527

4528 ccctaccaactaaggtacc                                                            4546
              KpnI
```

FIGURE 11

```
      PstI
   1 ctgcaggaattcattgtactcccagtatcattatagtgaaagttttggctctctcgccggtggttttttacctctattta    80

81 aagggttttccacctaaaaattctggtatcattctcactttacttgttactttaatttctcataatctttggttgaaat   160

161 tatcacgcttccgcacacgatatccctacaaatttattatttgttaaacattttcaaaccgcataaaattttatgaagtc   240

241 ccgtctatctttaatgtagtctaacattttcatattgaaatatataatttacttaattttagcgttggtagaaagcataa   320

321 tgatttattcttattcttcttcatataaatgtttaatatacaatataaacaaattctttaccttaagaaggatttcccat   400

401 tttatattttaaaaatatatttatcaaatattttttcaaccacgtaaatctcataataataagttgtttcaaaagtaataa   480

481 aatttaactccataatttttttattcgactgatcttaaagcaacacccagtgacacaactagccattttttctttgaat    560

561 aaaaaaatccaattatcattgtatttttttttatacaatgaaaatttcaccaaacaatcatttgtggtatttctgaagcaa   640

641 gtcatgttatgcaaaattctataattcccatttgacactacggaagtaactgaagatctgcttttacatgcgagacacat   720

721 cttctaaagtaattttaataatagttactatattcaagatttcatatatcaaatactcaatattacttctaaaaaattaa   800

801 ttagatataattaaaatattactttttttaatttttaagtttaattgttgaatttgtgactattgatttattattctactat   880

881 gtttaaattgttttatagatagtttaaagtaaatataagtaatgtagtagagtgttagagtgttaccctaaaccataaac   960

961 tataagatttatggtggactaattttcatatatttcttattgcttttaccttttcttggtatgtaagtccgtaactggaa  1040

1041 ttactgtgggttgccatggcactctgtggtcttttggttcatgcatggatgcttgcgcaagaaaaagacaaagaacaaag  1120

1121 aaaaaagacaaaacagagagacaaaacgcaatcacacaaccaactcaaattagtcactggctgatcaagatcgccgcgtc  1200

1201 catgtatgtctaaatgccatgcaaagcaacacgtgcttaacatgcactttaaatggctcacccatctcaacccacacaca  1280

1281 aacacattgccttttcttcatcatcaccacaaccacctgtatatattcattctcttccgccacctcaatttcttcactt   1360

1361 caacacacgtcaacctgcatatgcgtgtcatcccatgcccaaatctccatgcatgttccaaccaccttctctcttatata   1440

1441 atacctataaatacctctaatatcactcacttctttcatcatccatccatccagagtactactactctactactataata   1520

1521 ccccaacccaactcatattcaatactactctact ATG AAT GGT CTC GAA ACT CAC AAC ACA AGG CTC     1587
   1                                    M   N   G   L   E   T   H   N   T   R   L     11

1588 TGT ATC GTA GGA AGT GGC CCA GCG GCA CAC ACG GCG GCG ATT TAC GCA GCT AGG GCT GAA   1647
  12 C   I   V   G   S   G   P   A   A   H   T   A   A   I   Y   A   A   R   A   E    31

1648 CTT AAA CCT CTT CTC TTC GAA GGA TGG ATG GCT AAC GAC ATC GCT CCC GGT GGT CAA CTA   1707
  32 L   K   P   L   L   F   E   G   W   M   A   N   D   I   A   P   G   G   Q   L    51

1708 ACA ACC ACC ACC GAC GTC GAG AAT TTC CCC GGA TTT CCA GAA GGT ATT CTC GGA GTA GAG   1767
  52 T   T   T   T   D   V   E   N   F   P   G   F   P   E   G   I   L   G   V   E    71
```

FIGURE 11 (CONT'D)

```
1768 CTC ACT GAC AAA TTC CGT AAA CAA TCG GAG CGA TTC GGT ACT ACG ATA TTT ACA GAG ACG 1827
  72  L   T   D   K   F   R   K   Q   S   E   R   F   G   T   T   I   F   T   E   T   91

1828 GTG ACG AAA GTC GAT TTC TCT TCG AAA CCG TTT AAG CTA TTC ACA GAT TCA AAA GCC ATT 1887
  92  V   T   K   V   D   F   S   S   K   P   F   K   L   F   T   D   S   K   A   I  111

1888 CTC GCT GAC GCT GTG ATT CTC GCT ACT GGA GCT GTG GCT AAG CGG CTT AGC TTC GTT GGA 1947
 112  L   A   D   A   V   I   L   A   T   G   A   V   A   K   R   L   S   F   V   G  131

1948 TCT GGT GAA GGT TCT GGA GGT TTC TGG AAC CGT GGA ATC TCC GCT TGT GCT GTT TGC GAC 2007
 132  S   G   E   G   S   G   G   F   W   N   R   G   I   S   A   C   A   V   C   D  151

2008 GGA GCT GCT CCG ATA TTC CGT AAC AAA CCT CTT GCG GTG ATC GGT GGA GGC GAT TCA GCA 2067
 152  G   A   A   P   I   F   R   N   K   P   L   A   V   I   G   G   D   S   A  171

2068 ATG GAA GAA GCA AAC TTT CTT ACA AAA TAT GGA TCT AAA GTG TAT ATA ATC CAT AGG AGA 2127
 172  M   E   E   A   N   F   L   T   K   Y   G   S   K   V   Y   I   I   H   R   R  191

2128 GAT GCT TTT AGA GCG TCT AAG ATT ATG CAG CAG CGA GCT TTG TCT AAT CCT AAG ATT GAT 2187
 192  D   A   F   R   A   S   K   I   M   Q   Q   R   A   L   S   N   P   K   I   D  211

2188 GTG ATT TGG AAC TCG TCT GTT GTG GAA GCT TAT GGA GAT GGA GAA AGA GAT GTG CTT GGA 2247
 212  V   I   W   N   S   S   V   V   E   A   Y   G   D   G   E   R   D   V   L   G  231

2248 GGA TTG AAA GTG AAG AAT GTG GTT ACC GGA GAT GTT TCT GAT TTA AAA GTT TCT GGA TTG 2307
 232  G   L   K   V   K   N   V   V   T   G   D   V   S   D   L   K   V   S   G   L  251

2308 TTC TTT GCT ATT GGT CAT GAG CCA GCT ACC AAG TTT TTG GAT GGT GGT GTT GAG TTA GAT 2367
 252  F   F   A   I   G   H   E   P   A   T   K   F   L   D   G   G   V   E   L   D  271

2368 TCG GAT GGT TAT GTT GTC ACG AAG CCT GGT ACT ACA CAG ACT AGC GTT CCC GGA GTT TTC 2427
 272  S   D   G   Y   V   V   T   K   P   G   T   T   Q   T   S   V   P   G   V   F  291

2428 GCT GCG GGT GAT GTT CAG GAT AAG AAG TAT AGG CAA GCC ATC ACT GCT GCA GGA ACT GGG 2487
 292  A   A   G   D   V   Q   D   K   K   Y   R   Q   A   I   T   A   A   G   T   G  311

2488 TGC ATG GCA GCT TTG GAT GCA GAG CAT TAC TTA CAA GAG ATT GGA TCT CAG CAA GGT AAG 2547
 312  C   M   A   A   L   D   A   E   H   Y   L   Q   E   I   G   S   Q   Q   G   K  331

2548 AGT GAT ATG GCG GAT ACA GCT AGA GGA ACC CAT CAC GAT ATC ATC GGC AGA GAC CAG TAC 2607
 332  S   D   M   A   D   T   A   R   G   T   H   H   D   I   I   G   R   D   Q   Y  351

2608 CCG ATG ATG GGC CGA GAC CGA GAC CAG TAC CAG ATG TCC GGA CGA GGA TCT GAC TAC TCC 2667
 352  P   M   M   G   R   D   R   D   Q   Y   Q   M   S   G   R   G   S   D   Y   S  371

2668 AAG TCT AGG CAG ATT GCT AAA GCT GCA ACT GCT GTC ACA GCT GGT GGT TCC CTC CTT GTT 2727
 372  K   S   R   Q   I   A   K   A   A   T   A   V   T   A   G   G   S   L   L   V  391
```

FIGURE 11 (CONT'D)

```
2728 CTC TCC AGC CTT ACC CTT GTT GGA ACT GTC ATA GCT TTG ACT GTT GCA ACA CCT CTG CTC 2787
392  L   S   S   L   T   L   V   G   T   V   I   A   L   T   V   A   T   P   L   L   411

2788 GTT ATC TTC AGC CCA ATC CTT GTC CCG GCT CTC ATC ACA GTT GCA CTC CTC ATC ACC GGT 2847
412  V   I   F   S   P   I   L   V   P   A   L   I   T   V   A   L   L   I   T   G   431

2848 TTT CTT TCC TCT GGA GGG TTT GGC ATT GCC GCT ATA ACC GTT TTC TCT TGG ATT TAC AA g 2907
432  F   L   S   S   G   G   F   G   I   A   A   I   T   V   F   S   W   I   Y   K   451

2908 taagcacacatttatcatcttacttcataatttgtgcaatatgtgcatgcatgtgttgagccagtagctttggatcaat 2987

2988 tttttggtcgaataacaaatgtaacaataagaaattgcaaattctagggaacatttggttaactaaatacgaaatttga 3067

3068 cctagctagcttgaatgtgtctgtgtatatcatctatataggtaaaatgcttggtatgatacctattgattgtgaatag 3146

3147 G TAC GCA ACG GGA GAG CAC CCA CAG GGA TCA GAC AAG TTG GAC AGT GCA AGG ATG AAG 3204
452    Y   A   T   G   E   H   P   Q   G   S   D   K   L   D   S   A   R   M   K   470

3205 TTG GGA AGC AAA GCT CAG GAT CTG AAA GAC AGA GCT CAG TAC TAC GGA CAG CAA CAT ACT 3264
471  L   G   S   K   A   Q   D   L   K   D   R   A   Q   Y   Y   G   Q   Q   H   T   490

3265 GGT GGG GAA CAT GAC CGT GAC CGT ACT CGT GGT GGC CAG CAC ACT ACT TAA gcttaataagta 3327
491  G   G   E   H   D   R   D   R   T   R   G   G   Q   H   T   T   *   HindIII  507

3328 tgaactaaaatgcatgtaggtgtaagagctcatggagagcatggaatattgtatccgaccatgtaacagtataataactg 3407

3408 agctccatctcacttcttctatgaataaacaaaggatgttatgatatattaacactctatctatgcaccttattgttcta 3487

3488 tgataaatttcctcttattattataaatcatctgaatcgtgacggcttatggaatgcttcaaatagtacaaaaacaaatg 3567

3568 tgtactataagactttctaaacaattctaactttagcattgtgaacgagacataagtgttaagaagacataacaattata 3647

3648 atggaagaagtttgtctccatttatatattatatattacccacttatgtattatattaggatgttaaggagacataacaa 3727

3728 ttataaagagagaagtttgtatccatttatatattatatactacccatttatatattatacttatccacttatttaatgt 3807

3808 ctttataaggtttgatccatgatatttctaatatttttagttgatatgtatatgaaagggtactatttgaactctcttact 3887

3888 ctgtataaaggttggatcatccttaaagtgggtctatttaattttattgcttcttacagataaaaaaaaaattatgagtt 3967

3968 ggtttgataaaatattgaaggatttaaaataataataaataataaataacatataatatatgtatataaatttattataa 4047

4048 tataacatttatctataaaaaagtaaatattgtcataaatctatacaatcgtttagccttgctggacgactctcaattat 4127

4128 ttaaacgagagtaaacatatttgacttttggttatttaacaaattattatttaacactatatgaaattttttttttta 4207

4208 tcggcaaggaaataaaattaaattaggagggacaatggtgtgtcccaatccttatacaaccaacttccacaggaaggtca 4287
```

FIGURE 11 (CONT'D)

```
4288 ggtcggggacaacaaaaaaacaggcaagggaaattttttaatttgggttgtcttgtttgctgcataatttatgcagtaaa 4367

4368 acactacacataaccctttttagcagtagagcaatggttgaccgtgtgcttagcttctttttatttttattttttttatcagca 4447

4448 aagaataaataaaataaaatgagacacttcagggatgtttcaacccttatacaaaaccccaaaaacaagtttcctagcac 4527

4528 cctaccaactaaggtacc                                                              4545
                     KpnI
```

A  B

THIOREDOXIN AND THIOREDOXIN REDUCTASE CONTAINING OIL BODY BASED PRODUCTS

CROSS REFERENCE OF RELATED APPLICATIONS

This application is a continuation-in-part of U.S. application Ser. No. 09/448,755, filed Nov. 24, 1999, now abandoned, which claims the benefit of U.S. Provisional Application No. 60/109,997, filed Nov. 25, 1998.

FIELD OF THE INVENTION

The present invention provides novel emulsions which comprise oil bodies. The invention also provides a method for preparing the emulsions and the use of the emulsions in various products including pharmaceutical products, personal care products and food products.

BACKGROUND OF THE INVENTION

Emulsions are mixtures prepared from two mutually insoluble components. It is possible to generate mixtures of homogenous macroscopic appearance from these components through proper selection and manipulation of mixing conditions. The most common type of emulsions are those in which an aqueous component and a lipophilic component are employed and which in the art are frequently referred to as oil-in-water and water-in-oil emulsions. In oil-in-water emulsions the lipophilic phase is dispersed in the aqueous phase, while in water-in-oil emulsions the aqueous phase is dispersed in the lipophilic phase. Commonly known emulsion based formulations that are applied to the skin include cosmetic products such as creams, lotions, washes, cleansers, milks and the like as well as dermatological products comprising ingredients to treat skin conditions, diseases or abnormalities.

Generally emulsions are prepared in the presence of a multiplicity of other substances in order to achieve a desirable balance of emulsification, viscosity, stability and appearance. For example, the formulation of emulsions usually requires at least one, and frequently a combination of several, emulsifying agents. These agents facilitate the dispersal of one immiscible phase into the other and assist in stabilizing the emulsion. A comprehensive overview of emulsifying agents and their applications may be found in Becher, P. Encyclopedia of Emulsion Technology, Dekker Ed., 1983. Active agents beneficial to the skin, such as compounds to treat skin diseases, are also frequently formulated as emulsions in order to enhance their stability and to facilitate application of the active agent to the skin.

In the seeds of oilseed crops, which include economically important crops, such as soybean, rapeseed, sunflower and palm, the water insoluble oil fraction is stored in discrete subcellular structures variously known in the art as oil bodies, oleosomes, lipid bodies or spherosomes (Huang 1992, Ann. Rev. Plant Mol. Biol. 43: 177-200). Besides a mixture of oils (triacylglycerides), which chemically are defined as glycerol esters of fatty acids, oil bodies comprise phospholipids and a number of associated proteins, collectively termed oil body proteins. From a structural point of view, oil bodies are considered to be a triacylglyceride matrix encapsulated by a monolayer of phospholipids in which oil body proteins are embedded (Huang, 1992, Ann. Rev. Plant Mol. Biol. 43: 177-200). The seed oil present in the oil body fraction of plant species is a mixture of various triacylglycerides, of which the exact composition depends on the plant species from which the oil is derived. It has become possible through a combination of classical breeding and genetic engineering techniques, to manipulate the oil profile of seeds and expand on the naturally available repertoire of plant oil compositions. For an overview of the ongoing efforts in his area, see Designer Oil Crops/Breeding, Processing and Biotechnology, D. J. Murphy Ed., 1994, VCH Verlagsgesellschaft, Weinheim, Germany.

Plant seed oils are used in a variety of industrial applications, including the personal care industry. In order to obtain the plant oils used in these applications, seeds are crushed or pressed and subsequently refined using processes such as organic extraction, degumming, neutralization, bleaching and filtering. Aqueous extraction of plant oil seeds has also been documented (for example, Embong and Jelen, 1977, Can. Inst. Food Sci. Technol. J. 10: 239-243). Since the objective of the processes taught by the prior art is to obtain pure oil, oil bodies in the course of these production processes lose their structural integrity. Thus, the prior art emulsions formulated from plant oils generally do not comprise intact oil bodies.

Although fossil oil based products dominate certain markets, in other applications, oils derived from plant sources and fossil sources are in direct competition.

Lauric oils, for example, which are widely used in the manufacture of detergents, are obtained from fossil oils as well as from coconut oil and more recently from genetically engineered rapeseed (Knauf, V. C., 1994, Fat. Sci. Techn. 96: 408). However, there is currently an increasing demand for biodegradable sources of raw materials. The plant oil body based emulsions of the present invention offer an advantage over similar mineral oil based formulations, in that the oil fraction is derived from a renewable and environmentally friendly source. In one aspect, the present invention relates to thioredoxin and thioredoxin reductase. Thioredoxins are relatively small proteins (typically approximately 12 kDa) that belong to the family of thioltransferases, which catalyze oxido-reductions via the formation or hydrolysis of disulfide bonds and are widely, if not universally, distributed throughout the animal plant and bacterial kingdom. In order to reduce the oxidized thioredoxin, two cellular reductants provide the reduction equivalents, reduced ferredoxin and NADPH. These reduction equivalents are supplied via different thioredoxin reductases including the NADPH thioredoxin reductase and ferredoxin thioredoxin reductase. The latter thioredoxin reductase is involved in the reduction of plant thioredoxins designated as TRx and TRm, both of which are involved in the regulation of photosynthetic processes in the chloroplast. The NADPH/thioredoxin active in plant seeds is designated TRh and is capable of the reduction of a wide range of proteins thereby functioning as an important cellular redox buffer.

Thioredoxins have been obtained from several organisms including *Arabidopsis thaliana* (Riveira Madrid et al. (1995) Proc. Natl. Acad. Sci. 92: 5620-5624), wheat (Gautier et al. (1998) Eur. J. Biochem. 252: 314-324); *Escherichia coli* (Hoeoeg et al (1984) Biosci. Rep. 4: 917-923) and thermophylic microorganisms such as *Methanococcus jannaschii* and *Archaeoglobus fulgidus* (PCT Patent Application 00/36126). Thioredoxins have also been recombinantly expressed in several host systems including bacteria (Gautier et al. (1998) Eur J. Biochem. 252: 314-324) and plants (PCT Patent Application WO 00/58453) Commercial preparations of *E. coli* sourced thioredoxins are readily available from for example: Sigma Cat No. T 0910 Thioredoxin (*E. coli*, recombinant; expressed in *E. coli*).

NADPH-thioredoxin reductase is a cytosolic homodimeric enzyme comprising typically 300-500 amino acids. Crystal structures of both *E. coli* and plant NADPH-thioredoxin reductase have been obtained (Waksman et al. (1994) J. Mol. Biol. 236: 800-816; Dai et al. (1996) J. Allergy Clin. Immunol. 103: 690-697). NADPH-thioredoxin reductases have been expressed in heterologous hosts, for example the Arabidopsis NADPH-thioredoxin reductase has been expressed in *E. coli* (Jacquot et al. (1994) J. Mol. Biol. 235: 1357-1363) and wheat (PCT Patent Application 00/58453).

U.S. Pat. Nos. 5,683,740 to Voultoury et al. and 5,613,583 to Voultoury et al. disclose emulsions comprising lipid vesicles that have been prepared from crushed oleagenous plant seeds. In the course of the crushing process, oil bodies substantially lose their structural integrity. Accordingly, these patents disclose that in the crushing process, 70% to 90% of the seed oil is released in the form of free oil. Thus the emulsions which are the subject matter of these patents are prepared from crushed seeds from which a substantial amount of free oil has been released while the structural integrity of the oil bodies is substantially lost. In addition, the emulsions disclosed in both of these patents are prepared from relatively crude seed extracts and comprise numerous endogenous seed components including glycosylated and non-glycosylated non-oil body seed proteins. It is a disadvantage of the emulsions to which these patents relate that they comprise contaminating seed components imparting a variety of undesirable properties, which may include allergenicity and undesirable odour, flavour, color and organoleptic characteristics, to the emulsions. Due to the presence of seed contaminants, the emulsions disclosed in these patents have limited applications.

SUMMARY OF THE INVENTION

The present invention relates to novel emulsion formulations which are prepared from oil bodies. The emulsion formulations of the subject invention are obtainable in non-toxic and food grade forms. In addition, the emulsion formulations are advantageously prepared from an oil body preparation which is creamy in texture and thus may be readily applied in a variety of products including pharmaceutical products personal care products and food products.

The invention also provides methods for preparing the emulsion formulations comprising oil bodies. Accordingly, the present invention provides a method for preparing emulsion formulations comprising: 1) obtaining oil bodies from a cell; 2) washing the oil bodies; and 3) formulating the washed oil bodies into an emulsion.

In a preferred embodiment of the invention, the washed oil body preparation is obtained from plant seeds, including seeds obtainable from flax, safflower, rapeseed, soybean, maize and sunflower. Accordingly, the invention provides a method for preparing the emulsion formulations from plant seeds comprising:

(a) grinding plant seeds to obtain ground seeds comprising substantially intact oil bodies;
(b) removing solids from the ground seeds;
(c) separating the oil body phase from the aqueous phase;
(d) washing the oil body phase to yield a washed oil body preparation; and
(e) formulating the washed oil body preparation into an emulsion.

In a preferred embodiment of the invention, a liquid phase is added to the seeds prior to or while grinding the seeds.

In a further preferred embodiment of the invention, formulating the emulsion comprises stabilizing the washed oil body preparation to prevent degradation of the oil bodies either by physical forces or chemical forces.

In a preferred embodiment the oil bodies are formulated with the redox proteins thioredoxin and/or thioredoxin reductase. Accordingly the present invention further provides a method for the preparation of an emulsion formulation comprising: 1) obtaining oil bodies from a cell; 2) washing the oil bodies; and 3) formulating the washed oil bodies with thioredoxin or thioredoxin reductase.

In a further preferred embodiment thioredoxin or thioredoxin reductase are produced in a cell. The thioredoxin or thioredoxin reductase are obtained from the cell by association of the thioredoxin or thioredoxin reductase with oil bodies through an oil body targeting protein capable of association with the oil body and the thioredoxin and thioredoxin reductase. The oil bodies associated with the thioredoxin or thioredoxin reductase are then used to prepare an emulsion.

Accordingly the present invention provides a method for preparing an emulsion formulation comprising oil bodies said method comprising:

(a) producing in a cell a thioredoxin or thioredoxin reductase;

(b) associating said thioredoxin or thioredoxin reductase with oil bodies through an oil body targeting protein capable of associating with said thioredoxin or thioredoxin reductase and said oil bodies;

(c) obtaining said oil bodies associated with said thioredoxin or thioredoxin reductase;

(d) washing the oil bodies to obtain a washed oil body preparation comprising thioredoxin or thioredoxin reductase; and (e) formulating said washed oil bodies associated with thioredoxin or thioredoxin reductase into an emulsion.

In a further aspect the present invention provides an emulsion comprising washed oil bodies and thioredoxin or thioredoxin reductase.

Additional objects, advantages and features of the present invention will become apparent after consideration of the accompanying drawings and the following detailed description of the invention.

BRIEF DESCRIPTION OF THE DRAWINGS

FIG. 3 shows the comparison of the published NADPH thioredoxin reductase sequence (SEQ.ID.NO.1) (ATTHIREDB, Jacquot et al. J. Mol. Biol. (1994) 235 (4):1357-63.) with the sequence isolated in this report (TR) (SEQ.ID.NO.2).

FIG. 4 show the nucleotide sequence (SEQ.ID.NO.2) and deduced amino acid sequence (SEQ.ID.NO.3) of the NADPH Thioredoxin reductase sequence isolated in this report.

FIG. 5 shows the comparison of the deduced amino acid sequence of the published NADPH thioredoxin reductase sequence (SEQ.ID.NO.4) (ATTHIREDB Jacquot et al. J.

Figure 1:
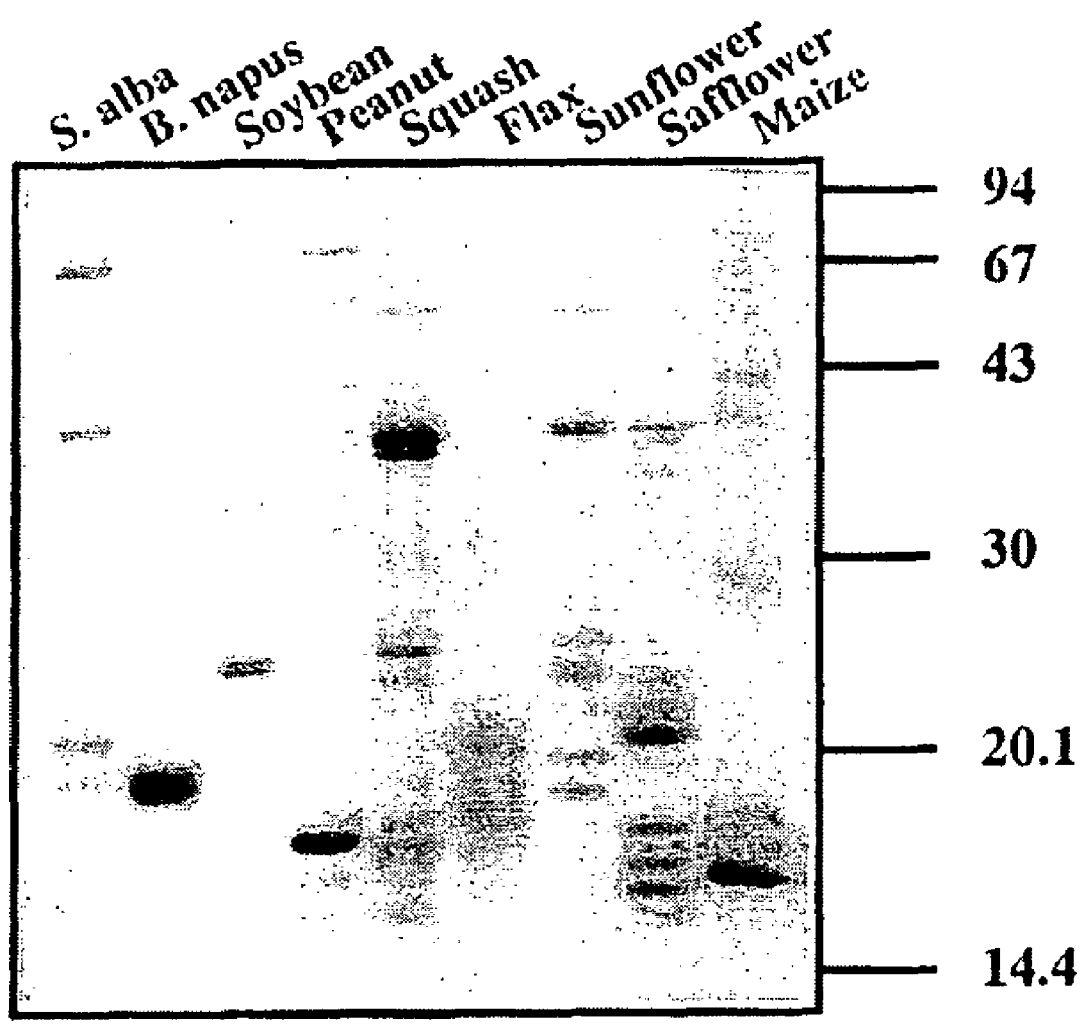
FIG. 1 is a Coomassie blue stained gel of a washed oil body preparation from white mustard, rapeseed (*Brassica napus*), soybean, peanut, squash, flax, sunflower, safflower and maize.

Mol. Biol. (1994) 235 (4):1357-63.) with the sequence isolated in this report (TR) (SEQ.ID.NO.3).

FIG. 6 shows the nucleotide sequence of the phaseolin promoter-Arabidopsis Trxh-phaseolin terminator sequence (SEQ.ID.NO.5). The Trxh coding sequence and its deduced amino acid sequence is indicated (SEQ.ID.NO.6). The phaseolin promoter corresponds to nucleotide 6-1554, and the phaseolin terminator corresponds to nucleotide sequence 1905-3124. The promoter was furnished with a PstI site (nt 1-6) and the terminator was furnished with a HindIII site (nt 1898-1903) and a KpnI site (nt 3124-3129) to facilitate cloning.

FIG. 7 shows the nucleotide sequence of the phaseolin promoter-oleosin Trxh-phaseolin terminator sequence (SEQ.ID.NO.7). The oleosin-Trxh coding sequence and its deduced amino acid sequence (SEQ.ID.NOS.8 and 9) is indicated. As in FIG. 4, the phaseolin promoter corresponds to nucleotide 6-1554. The sequence encoding oleosin corresponds to nt 1555-2313, the intron in this sequence (nt 1908-2147) is indicated in italics. The Trxh coding sequence corresponds to nt 2314-2658. The phaseolin terminator corresponds to nucleotide sequence 2664-3884. As in FIG. 4 the synthetic PstI, HindIII and KpnI sites are also indicated.

FIG. 8 shows the nucleotide sequence of the phaseolin promoter-Trxh oleosin-phaseolin terminator sequence (SEQ.ID.NO.10). The Trxh oleosin-coding sequence and its deduced amino acid sequence is indicated (SEQ.ID.NOS. 11 and 12). As in FIGS. 4 and 5, the phaseolin promoter corresponds to nucleotide 6-1554. The Trxh coding sequence corresponds to nt 1555-1896. The sequence encoding oleosin corresponds to nt 1897-2658, the intron in this sequence (nt 2250-2489) is indicated in italics. The phaseolin terminator corresponds to nucleotide sequence 2664-3884. As in FIGS. 4 and 5 the synthetic PstI, HindIII and KpnI sites are also indicated.

FIG. 9 shows the nucleotide sequence of the phaseolin promoter-thioredoxin reductase-phaseolin terminator sequence (SEQ.ID.NO.13). The thioredoxin reductase coding sequence and its deduced aminoacid sequence is indicated (SEQ.ID.NO.14). The phaseolin promoter corresponds to nucleotide 6-1554. The thioredoxin reductase coding sequence corresponds to nt 1555-2556. The phaseolin terminator corresponds to nucleotide sequence 2563-3782. The synthetic PstI, HindIII and KpnI sites are also indicated.

FIG. 10 shows the nucleotide sequence of the phaseolin promoter-oleosin thioredoxin reductase-phaseolin terminator sequence (SEQ.ID.NO.15). The oleosin-thioredoxin reductase coding sequence and its deduced amino acid sequence is indicated (SEQ.ID.NOS.16 and 17). The phaseolin promoter corresponds to nucleotide 6-1554. The sequence encoding oleosin corresponds to nt 1555-2313, the intron in this sequence (nt 1980-2147) is indicated in italics. The thioredoxin reductase coding sequence corresponds to nt 2314-3315. The phaseolin terminator corresponds to nucleotide sequence 3321-4540. The synthetic PstI, HindIII and KpnI sites are also indicated.

FIG. 11 shows the nucleotide sequence of the phaseolin promoter-thioredoxin reductase oleosin-phaseolin terminator sequence (SEQ.ID.NO.18). The thioredoxin reductase coding sequence and its deduced amino acid sequence is indicated (SEQ.ID.NOS.19 and 20). The phaseolin promoter corresponds to nucleotide 6-1554. The thioredoxin reductase coding sequence corresponds to nt 1555-2553. The sequence encoding oleosin corresponds to nt 2554-3315, the intron in this sequence (nt 2751-3146) is indicated in italics. The phaseolin terminator corresponds to nucleotide sequence 3321-4540. The synthetic PstI, HindIII and KpnI sites are also indicated.

FIGS. 12A and B are a gel and Western blot, respectively, showing the analysis of total seed extracts (Lane 1 and 2) and oil body protein extract (Lane 3) of wt Arabidopsis (Lane 1) and Arabidopsis transformed with pSBS2510 (oleosin-thioredoxin). Panel A; coomassie stained gel, Panel B; Western blot treated with a monoclonal antibody raised against Arabidopsis oleosin followed by an alkaline phosphatase linked secondary antibody and NBT/BCIP color reaction. Indicated are the most abundant native oleosin (red arrow) and the oleosin-thioredoxin fusion protein (green arrow).

FIGS. 13A and B are a gel and Western blot, respectively, showing the analysis of total seed extracts (Lane 2) and oil body protein extract (Lane 1 and 3) of wt Arabidopsis (Lane 1) and Arabidopsis transformed with pSBS2521 (thioredoxin-oleosin, Lane 2 and 3). Panel A; coomassie stained gel, Panel B; Western blot treated with a polyclonal antibody raised against Arabidopsis thioredoxin protein followed by an alkaline phosphatase linked secondary antibody and NBT/BCIP color reaction. Panel C; Western blot treated with a monoclonal antibody raised against Arabidopsis oleosin followed by an alkaline phosphatase linked secondary antibody and NBT/BCIP color reaction. Indicated is the most abundant native oleosin (red arrow) and the thoredoxin oleosin fusion protein (blue arrow).

FIGS. 14A and B are a gel and Western blot, respectively, showing the analysis of total seed extracts of wt Arabidopsis (lane 1) and Arabidopsis transformed with pSBS2520 ("free" thioredoxin, lane 2, 3, 4, 5, 6, 7, 8) Panel A; coomassie stained gel, Panel B; Western blot treated with a polyclonal antibody raised against Arabidopsis thioredoxin protein followed by an alkaline phosphatase linked secondary antibody and NBT/BCIP color reaction. Indicated is the band reacting with the anti-thioredoxin antibody. A strong signal can be detected in lane 3, 5, 6, 7, 8 and no signal can be detected in the wt extract (Lane 1) and two seed extracts derived from 2 different transgenic lines (Lane 2, 4). The lack of detectable thioredoxin expression (as shown in Lane 2, 4) could be due to either a position effect or we are looking or these seeds could be derived from a non-trangenic (escape or false-positive) plant.

FIGS. 15A and B are Western blots showing the analysis of total seed of wt Arabidopsis (wt) and Arabidopsis transformed with pSBS2529 (thioredoxin reductase-oleosin, Lane 1, 2 and 3). Panel A; Western blot treated with a polyclonal antibody raised against Arabidopsis thioredoxin reductase protein followed by an alkaline phosphatase linked secondary antibody and NBT/BCIP color reaction. Panel B; Western blot treated with a monoclonal antibody raised against Arabidopsis oleosin followed by an alkaline phosphatase linked secondary antibody and NBT/BCIP color reaction. Indicated is the most abundant native oleosin and the thoredoxin reductase oleosin fusion protein (blue arrow).

Figure 16:
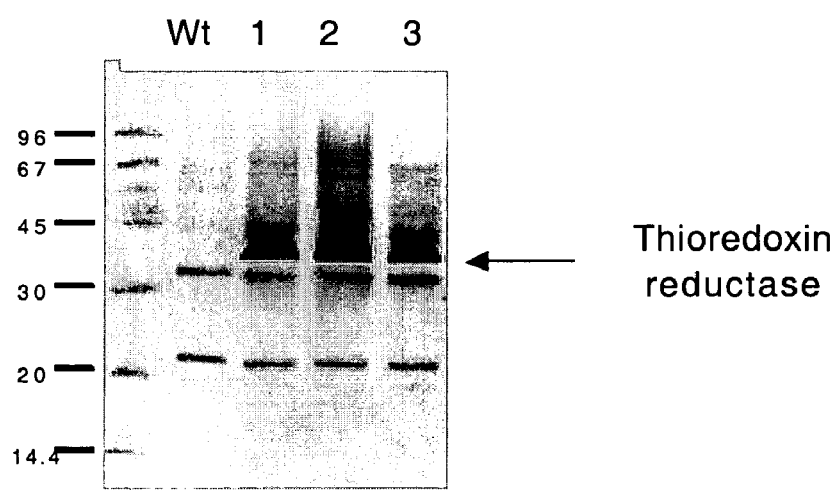

FIG. 16 is a Western blot showing the analysis of total seed extracts of wt Arabidopsis (wt) and Arabidopsis transformed with pSBS2527 ("free" thioredoxin reductase, Lane 1, 2, 3). Indicated is a Western blot treated with a polyclonal antibody raised against Arabidopsis thioredoxin reductase protein followed by an alkaline phosphatase linked secondary antibody and NBT/BCIP color reaction. Indicated is the overexpressed thioredoxin reductase in Lane 1, 2 and 3.

FIGS. 17A and B are a gel and Western blot, respectively, showing the analysis of total seed extracts (Lane 1 and 2) and oil body protein extract (Lane 3) of wt Arabidopsis (Lane 1) and Arabidopsis transformed with pSBS2531 (oleosin-Thioreoxin reductasePanel A; Coomassie stained gel, Panel B; Western blot treated with a monoclonal antibody raised against Arabidopsis oleosin followed by an alkaline phosphatase-linked secondary antibody and NBT/BCIP color reaction. Indicated are the most abundant native oleosin (red arrow) and the oleosin-DMSR fusion protein (green arrow). The oil bodies as shown in lane 3 were not washed. As a result some (contaminating) seed proteins can be seen in the oil body extract as well. However the most abundant proteins in this extract are native oleosin and oleosin-DMSR fusion protein. As expected the wt seed extract (lane 1) showed reactivity only with the native oleosin.

DETAILED DESCRIPTION OF THE INVENTION

As hereinbefore mentioned, the present invention relates to emulsion formulations comprising oil bodies derived from a cell. In one embodiment, the present invention provides an emulsion formulation comprising washed oil bodies.

In another embodiment, the present invention provides a method for preparing an emulsion formulation comprising: 1) obtaining oil bodies from a cell; 2) washing the oil bodies; and 3) formulating the washed oil bodies into an emulsion.

In a preferred embodiment of the invention, formulating the washed oil bodies comprises stabilization of the washed oil bodies so that an oil body preparation is obtained that is chemically as well as physically stable.

The cell can be any cell that contains oil bodies (or oil body-like structures) including plant cells, animal cells, fungal cells and bacterial cells. In a preferred embodiment of the invention the oil bodies are obtained from a plant cell. The oil bodies may be obtained from a plant cell by rupturing the plant cell membrane and cell wall using any method which releases the cells constituents without substantially compromising the structural integrity of the oil bodies. More preferably, the oil bodies are obtained from plant seeds. Accordingly, the present invention further provides a method for preparing an emulsion formulation comprising:

(1) obtaining oil bodies from plant seeds by a method that comprises:
   (a) grinding plant seeds to obtain ground seeds comprising substantially intact oil bodies;
   (b) removing solids from the ground seeds; and
   (c) separating the oil body phase from the aqueous phase;
(2) washing the oil body phase to yield a washed oil body preparation; and
(3) formulating the washed oil body preparation into an emulsion.

In a preferred embodiment of the invention, a liquid phase is added to the seeds prior to or while grinding the seeds.

The term "grinding" as used herein means milling, crushing, chopping or granulating the seeds and these terms may be used interchangeably throughout this application. In the process, the seed cells are broken open while the oil bodies remain substantially intact. The term "substantially intact" as used herein means that the oil bodies have not released greater than 50% (v/v) of their total seed oil content in the form of free oil. Preferably, grinding of the seeds results in release of less than about 50% (v/v) of the total seed oil content in the form of free oil, more preferably less than about 20% (v/v) and most preferably less than about 10% (v/v).

The term "solids" as used herein means any material that is not soluble in the aqueous phase or in the oil body phase, such as seed hulls.

The term "washing the oil bodies" as used herein means any process that removes cellular contaminants from the oil body phase, in particular any contaminant which imparts undesirable properties to the emulsion formulation, such as allergenic properties, undesirable color, odor, flavor or dermatological characteristics or any other undesirable property. Examples of methods of washing include gravitation based separation methods such as centrifugation and size exclusion based separation techniques such as membrane ultrafiltration and crossflow microfiltration. Washing methods and conditions are selected in accordance with the desired purity of the oil body preparation.

The term "washed oil body preparation" as used herein means a preparation of oil bodies from which a significant amount of cellular material has been removed including contaminants which impart undesirable properties to the emulsion formulation, such as allergenic properties, undesirable color, odor, taste or organoleptic characteristics or any other undesirable property. Preferably, the washed oil body preparation contains less than about 75% (w/w) of all endogenously present non-oil body seed proteins, more preferably the washed oil body preparation contains less than about 50% (w/w) of endogenously present non-oil body seed proteins and most preferably less than about 10% (w/w) of endogenously present non-oil body seed proteins.

By "formulating the oil bodies into an emulsion", it is meant that the washed oil body preparation is mixed, homogenized or prepared until an emulsion is formed. In a preferred embodiment, an additional ingredient is added, such as a liquid phase, and the washed oil body preparation and the additional ingredient are mixed until a homogenous mixture is attained. The emulsion formulation of the present invention is preferably prepared for use in any pharmaceutical product, personal care product or food product.

Properties of the Oil Bodies

The emulsion formulations of the present invention comprise intact washed oil bodies of approximately uniform size, shape and density. When viewed under the electron microscope, oil bodies are found to be more or less spherically shaped structures (see: Example Murphy, D. J. and Cummins I., 1989, Phytochemistry, 28: 2063-2069; Jacks, T. J. et al., 1990, JAOCS, 67: 353-361). Typical sizes of oil bodies vary between 0.4 micrometer and 1.5 micrometer (Murphy, D. J. and Cummins I., 1989, Phytochemistry, 28: 2063-2069). When analyzed using a Malvern Size Analyzer, it was found that oil bodies in a washed oil body preparation isolated from rapeseed were symmetrically and unimodally distributed around 1 micrometer. Using a Malvern Size Analyzer a washed oil body preparation could be clearly distinguished from commercially obtainable oil-in-water emulsions including soymilk, mayonnaise (Kraft Real Mayonnaise) and two coconut milk preparations (Tosca, Aroy-D). The exact size and density of the oil bodies depends at least in part on the precise protein/phospholipid/triacylglyceride composition which is present. Preparing washed oil bodies according to the present invention does not result in a substantive alteration in the shape of the oil bodies in comparison with those present in whole seed when viewed under the electron microscope.

Upon breaking open a cell containing oil bodies, the oil body fraction may be rapidly and simply separated from aqueous solutions since in aqueous solutions the oil body fraction will float upon application of centrifugal force. In solutions, where the density of the oil body fraction is greater than that of the solvent, such as 95% ethanol, the oil bodies will sediment under the same conditions. The oil body fraction may also be separated from the aqueous fraction through size-exclusion based separation techniques, such as membrane filtration, which may be advantageous in that more uniformly sized oil bodies may be acquired.

The oil bodies present in the washed oil body preparations of the present invention are resistant to exposure to strong acids and bases, including prolonged exposure to acidic conditions at least as low as pH 2 and alkaline conditions at least as high as pH 10. When exposed to pH 12, a slight loss of oil was observed, indicating a loss of integrity of the oil body structure. In addition, extraction with various organic solutions, including methanol, ethanol, hexane, isopropyl alcohol and ethyl acetate, does not or only slightly compromise the integrity of the oil bodies present in the washed oil body preparation. The oil bodies present in the washed oil body preparation were also found to withstand mixing with the anionic detergent, sodium dodecyl sulfate (SDS), the cationic, detergent hexadecyl trimethyl bromide and Tween-80, a non-ionic detergent. Boiling of the washed oil body preparation in the presence of SDS was found to result at least partly in disintegration of the oil body structure. The oil bodies present in the washed oil body preparation are stable when maintained for 2 hours up to at least 100° C. A slow freeze and thaw of washed oil body preparations resulted in a change in their physical appearance characterized by the formation of clumps as opposed to a homogeneous emulsion. Oil body clumping following a freeze-thaw could also be prevented to a large degree by either a) flash freezing in liquid nitrogen instead of slow freezing at −20° C. or b) adding glycerol in excess of 5% (v/v) to the oil body preparation prior to freezing. The resistance to relatively harsh chemical and physical conditions, is a unique characteristic of the oil bodies present in the washed oil body preparation of the subject invention.

The present invention provides emulsion formulations comprising oil bodies from which a significant amount of seed contaminants have been removed. These contaminants include proteins, volatiles and other compounds which may impart undesirable color, odor, flavor, organoleptic characteristics or other undesirable characteristics. A number of seed proteins have been reported to cause allergenic reactions. For example, Ogawa et al. (1993, Biosci. Biotechnol. Biochem., 57:1030-1033) report allergenicity of the soybean glycoprotein P34 (alternatively referred to as Gly m Bd 30K). Allergenic reactions against rapeseed, wheat and barley seed proteins have also been reported (Armentia et al., 1993., Clin. Exp. Allergy 23: 410-415; Monsalve et al., 1993, Clin. Exp. Allergy 27: 833-841). Hence removal of contaminating seed proteins is advantageous. Washing conditions may be selected such that a substantially pure oil body preparation is obtained. In that case, only the oil body proteins are substantially present in the preparation.

For many applications, it is also considered desirable that a purer better defined oil body preparation is obtained, as this allows more control over the formulation process of the final emulsion. In order for the washed oil body preparation to be included in a diverse set of emulsions it is desirable that volatiles are kept to a minimum and the color is preferably light or white. Washing of the oil body preparation results in a lighter colored preparation. In addition, a substantial amount of volatiles is removed. Also removed by washing are compounds which promote the growth of microorganisms as it was observed that a washed oil body preparation had a longer shelf life than an unwashed preparation. Other compounds which are removed by washing include anti-nutritional glucosinilates and/or breakdown products thereof and fibrous material. When heat treated to 60° C. or 80° C., it was observed that larger quantities of water remained absorbed by the washed oil body preparation when compared with an unwashed preparation. Upon cooling down to room temperature and centrifugation, it was observed that the washed oil body preparation remained stable, while phase separation occurred in the unwashed preparation. Given the enhanced stability of washed oil bodies, they are preferred where the formulation process involves the application of heat. When heated to 40° C., the washed oil body preparation was able to absorb a larger quantity of exogenously added water without resulting in phase separation. Thus in the formulation of aqueous emulsions, washed oil bodies are preferred. The capacity to absorb exogenously added oils was also compared between a preparation of washed oil bodies and an unwashed preparation. Larger amounts of exogenous oil could be added to the washed oil body preparation before an unstable emulsion was formed. This is advantageous in formulations where exogenous oils or waxes are added in the formulation process such as where personal care products are prepared. When viscosity was compared between a washed oil body preparation and an unwashed preparation it was found that the washed preparation was more viscous. A more viscous preparation of oil bodies is desirable as this allows for more flexibility in the formulation process and eliminates the need for the addition of thickening agents in the formulation process.

Thus the washed oil body preparation provided here is superior to an unwashed preparation in many respects. The washed oil body preparation of the present invention is a better defined preparation with a longer shelf life and more preferable color, odor and viscosity characteristics. The washed oil body preparation also has superior water and oil absorption characteristics. Finally due to the removal of a significant amount of seed proteins, allergenic reactions are less likely to occur. These characteristics allow the use of the washed oil body preparation in the formulation of a variety of domestic and industrial emulsions.

The above observations were made using washed and unwashed oil body preparations obtained from rapeseed and prepared as detailed in Example 2 of the present application. It is believed that resistance to relatively harsh chemical and physical conditions will be a characteristic of the oil bodies present in the washed oil preparation of the subject invention regardless of the source of the oil bodies. However one or more of the hereinbefore documented properties for rapeseed oil bodies may vary depending on the cells from which the washed oil bodies preparation is obtained. Nevertheless it is to be clearly understood that the subject invention is drawn to an oil body preparation which may be obtained from any cell comprising oil bodies.

In one embodiment of the present invention, the oil bodies are obtained from plant seeds. The presence of intact oil bodies in the emulsion and the described characteristics of these oil bodies clearly distinguish the subject emulsion formulation from other materials which may be prepared from plant seeds.

Sources and Preparation of the Oil Bodies

The washed oil body preparation of the subject may be obtained from any cell containing oil bodies or oil body-like organelles. This includes animal cells, plant cells, fungal cells, yeast cells (Leber, R. et al., 1994, Yeast 10: 1421-1428), bacterial cells (Pieper-Fürst et al., 1994, J. Bacteriol. 176: 4328-4337) and algae cells (Rossler, P. G., 1988, J. Physiol. (London) 24: 394-400).

In preferred embodiments of the invention the oil bodies are obtained from a plant cell which includes cells from pollens, spores, seed and vegetative plant organs in which oil bodies or oil body-like organelles are present (Huang, 1992, Ann. Rev. Plant Physiol. 43: 177-200).

More preferably, the washed oil body preparation of the subject invention is prepared from plant seeds. Among the plant seeds useful herein preferred are those seeds obtainable from plant species selected from the group of plant species consisting of almond (*Prunus dulcis*); anise (*Pimpinella anisum*); avocado (*Persea* spp.); beach nut (*Fagus sylvatica*); borage (also known as evening primrose) (*Boragio officinalis*); Brazil nut (*Bertholletia excelsa*); candle nut (*Aleuritis tiglium*); carapa (*Carapa guineensis*); cashew nut (*Ancardium occidentale*); castor (*Ricinus communis*); coconut (*Cocus nucifera*); coriander (*Coriandrum sativum*); cottonseed (*Gossypium* spp.); crambe (*Crambe abyssinica*); *Crepis alpina*; croton (*Croton tiglium*); *Cuphea* spp.; dill (*Anethum gravealis*); *Euphorbia lagascae*; *Dimorphoteca pluvialis*; false flax (*Camolina sativa*); fennel (*Foeniculum vulgaris*); groundnut (*Arachis hypogaea*); hazelnut (*coryllus avellana*); hemp (*Cannabis sativa*); honesty plant (*Lunnaria annua*); jojoba (*Simmondsia chinensis*); kapok fruit (*Ceiba pentandra*); kukui nut (*Aleuritis moluccana*); *Lesquerella* spp., linseed/flax (*Linum usitatissimum*); macademia nut (*Macademia* spp.); maize (*Zea mays*); meadow foam (*Limnanthes alba*); mustard (*Brassica* spp. and *Sinapis alba*); oil palm (*Elaeis guineeis*); oiticia (*Licania rigida*); paw paw (*Assimina triloba*); pecan (*Juglandaceae* spp.); perilla (*Perilla frutescens*); physic nut (*Gatropha curcas*); pilinut (*Canarium ovatum*); pine nut (pine spp.); pistachio (*Pistachia vera*); pongam (*Bongamin glabra*); poppy seed (*Papaver soniferum*); rapeseed (*Brassica* spp.); safflower (*Carthamus tinctorius*); sesame seed (*Sesamum indicum*); soybean (*Glycine max*); squash (*Cucurbita maxima*); sal tree (*Shorea rubusha*); Stokes aster (*Stokesia laevis*); sunflower (*Helianthus annuus*); tukuma (*Astocarya* spp.); tung nut (*Aleuritis cordata*); vemonia (*Vernonia galamensis*); and mixtures thereof.

More preferred for use herein are oil bodies obtained from plant seeds selected from the group of plant species consisting of Brazil nut (*Bertholletia excelsa*); castor (*Ricinus communis*); coconut (*Cocus nucifera*); coriander (*Coriandrum sativum*); cottonseed (*Gossypium* spp.); groundnut (*Arachis hypogaea*); jojoba (*Simmondsia chinensis*); linseed/flax (*Linum usitatissimum*); maize (*Zea mays*); mustard (Brassica spp. and *Sinapis alba*); oil palm (*Elaeis guineeis*); olive (*Olea europaea*); rapeseed (Brassica spp.); safflower (*Carthamus tinctorius*); soybean (*Glycine max*); squash (*Cucurbita maxima*); sunflower (*Helianthus annuus*); and mixtures thereof Most preferred for use herein are oil bodies prepared from safflower (*Carthamus tinctorius*).

Plants are grown and allowed to set seed using agricultural cultivation practises well known to a person skilled in the art. After harvesting the seed, and if desired removal of material such as stones or seed hulls (dehulling), by for example sieving or rinsing, and optionally drying of the seed, seeds are subsequently processed by mechanical pressing, grinding or crushing. In a preferred embodiment, a liquid phase is added prior to or while grinding the seeds. This is known as wet milling. Preferably the liquid is water although organic solvents such as ethanol may also be used. Wet milling in oil extraction processes has been reported for seeds from a variety of plant species including: mustard (Aguilar et al 1990, Journal of Texture studies 22:59-84), soybean (U.S. Pat. No. 3,971,856; Carter et al., 1974, J. Am. Oil Chem. Soc. 51:137-141), peanut (U.S. Pat. No. 4,025,658; U.S. Pat. No. 4,362,759), cottonseed (Lawhon et al., 1977, J. Am. Oil, Chem. Soc. 63:533-534) and coconut (Kumar et al., 1995, INFORM 6 (11):1217-1240). It may also be advantageous to imbibe the seeds for a time period from about fifteen minutes to about two days in a liquid phase prior grinding. Imbibing may soften the cell walls and facilitate the grinding process. Imbibition for longer time periods may mimic the germination process and result in certain advantageous alterations in the composition of the seed constituents. Preferably the added liquid phase is water.

The seeds are preferably ground using a colloid mill, such as the MZ130 (Fryma Inc.). Besides colloid mills, other milling and grinding equipment capable of processing industrial scale quantities of seed may also be employed in the here described invention including: flaking rolls, disk mills, colloid mills, pin mills, orbital mills, IKA mills and industrial scale homogenizers. The selection of the mill may depend on the seed throughput requirements as well as on the source of the seed which is employed. It is of critical importance that seed oil bodies remain substantially intact during the grinding process. Grinding of the seeds therefore results in the release of preferably less than about 50% (v/v) of the total seed oil content in the form of free oil, more preferably less than about 20% (v/v) and most preferably less than about 10% (w/w). Any operating conditions commonly employed in oil seed processing, which tend to disrupt oil bodies are unsuitable for use in the process of the subject invention. Milling temperatures are preferably between 10° C. and 90° C. and more preferably between 26° C. and 30° C., while the pH is preferably maintained between 2.0 and 10.

Solid contaminants, such as seed hulls, fibrous material, undissolved carbohydrates and proteins and other insoluble contaminants, are removed from the crushed seed fraction. Separation of solid contaminants, may be accomplished using a decantation centrifuge, such as a HASCO 200 2-phase decantation centrifuge or a NX310B (Alpha Laval). Depending on the seed throughput requirements, the capacity of the decantation centrifuge may be varied by using other models of decantation centrifuges, such as 3-phase decanters. Operating conditions vary depending on the particular centrifuge which is employed and must be adjusted so that insoluble contaminating materials sediment and remain sedimented upon decantation. A partial separation of the oil body phase and liquid phase may be observed under these conditions.

Following the removal of insoluble contaminants, the oil body phase is separated from the aqueous phase. In a preferred embodiment of the invention a tubular bowl centrifuge is employed. In other embodiments, hydrocyclones, disc stack centrifuges, or settling of phases under natural gravitation or any other gravity based separation method may be employed. It is also possible to separate the oil body fraction from the aqueous phase employing size exclusion methods, such as membrane ultrafiltration and crossflow microfiltration. In preferred embodiments the tubular bowl centrifuge is a Sharples model AS-16 (Alpha Laval) or a AS-46 Sharples (Alpha Laval). A critical parameter is the size of the ring dam used to operate the centrifuge. Ring dams are removable rings with a central circular opening varying, in the case of the AS-16, from 28 to 36 mm and regulate the separation of the aqueous phase from the oil body phase thus governing the purity of the oil body fraction which is obtained. In preferred embodiments, a ring dam size of 29 or 30 mm is employed when using the AS-16. The exact ring dam size employed depends on the type of oil seed which is used as well as on the desired final consistency of the oil body preparation. The efficiency of separation is further affected by the flow rate. Where the AS-16 is used flow rates are typically between 750-1000 ml/min (ring dam size 29) or between 400-600 ml/min (ring dam size 30) and temperatures are preferably maintained between 26° C. and 30° C. Depending on the model centrifuge used, flow rates and ring dam sizes must be adjusted so that an optimal separation of the oil body fraction from the aqueous phase is achieved. These adjustments will be readily apparent to a skilled artisan.

Separation of solids and separation of the aqueous phase from the oil body fraction may also be carried out concomitantly using a gravity based separation method such as 3-phase tubular bowl centrifuge or a decanter or a hydrocyclone or a size exclusion based separation method.

The compositions obtained at this stage in the process, generally are relatively crude and comprise numerous endogenous seed proteins, which includes glycosylated and non-glycosylated proteins and other contaminants such as starch or glucosinilates or breakdown products thereof. The present invention comprises the removal of a significant amount of seed contaminants. To accomplish removal of contaminating seed material, the oil body preparation obtained upon separation from the aqueous phase is washed at least once by resuspending the oil body fraction and centrifuging the resuspended fraction. This process yields what for the purpose of this application is referred to as a washed oil body preparation. The number of washes will generally depend on the desired purity of the oil body fraction. Depending on the washing conditions which are employed, an essentially pure oil body preparation may be obtained. In such a preparation the only proteins present would be oil body proteins. In order to wash the oil body fraction, tubular bowl centrifuges or other centrifuges such hydrocyclones or disc stack centrifuges may be used. Washing of oil bodies may be performed using water, buffer systems, for example, sodium chloride in concentrations between 0.01 M and at least 2 M, 0.1 M sodium carbonate at high pH (11-12), low salt buffer, such as 50 mM Tris-HCl pH 7.5, organic solvents, detergents or any other liquid phase. In preferred embodiments the washes are performed at high pH (11-12). The liquid phase used for washing as well as the washing conditions, such as the pH and temperature, may be varied depending on the type of seed which is used. Washing at a number of different pH's between pH 2 and pH 11-12 may be beneficial as this will allow the step-wise removal of contaminants, in particular proteins. Preferably washing conditions are selected such that the washed oil body preparation comprises less than about 75% (w/w) of all endogenously present non-oil body seed proteins, more preferably less than about 50% (w/w) of endogenously present non-oil body seed proteins and most preferably less than about 10% (w/w) of endogenously present non-oil body proteins. Washing conditions are selected such that the washing step results in the removal of a significant amount of contaminants without compromising the structural integrity of the oil bodies. In embodiments where more than one washing step is carried out, washing conditions may vary for different washing steps. SDS gel electrophoresis or other analytical techniques may conveniently be used to monitor the removal of endogenous seed proteins and other contaminants upon washing of the oil bodies. It is not necessary to remove all of the aqueous phase between washing steps and the final washed oil body preparation may be suspended in water, a buffer system, for example, 50 mM Tris-HCl pH 7.5, or any other liquid phase and if so desired the pH may be adjusted to any pH between pH 2 and pH 10.

The process to manufacture the washed oil body preparation may be performed in batch operations or in a continuous flow process. Particularly when tubular bowl centrifuges are used, a system of pumps operating between steps (a) and (b), (b) and (c), and (c) and (d) a continuous flow throughout the processing system is generated. In a preferred embodiment, the pumps are 1 inch M2 Wilden air operated double diaphragm pumps. In other embodiments, pumps, such as hydraulic or peristaltic pumps may be employed. In order to maintain a supply of homogenous consistency to the decantation centrifuge and to the tubular bowl centrifuge, homogenizers, such as an IKA homogenizer may be added between the separation steps. In-line homogenizers may also be added in between various centrifuges or size exclusion based separation equipment employed to wash the oil body preparations. Ring dam sizes, buffer compositions, temperature and pH may differ in each washing step from the ring dam size employed in the first separation step.

In embodiments of the invention where the oil bodies are isolated from softer tissues, for example the mesocarp tissue of olives, the techniques applied to break open the cell may vary somewhat from those used to break harder seeds. For example, pressure-based techniques may be preferred over crushing techniques. The methodology to isolate oil bodies on a small scale has been reported for isolation of oil bodies from mesocarp tissues in olive (*Olea europaea*) and avocado (*Persea americana*) (Ross et al., Plant Science, 1993, 93: 203-210) and from microspore-derived embryos of rapeseed (*Brassica napus*) (Holbrook et al., Plant Physiol., 1991, 97: 1051-1058).

In embodiments of the invention where oil bodies are obtained from non-plant cells, the washed oil body preparation is isolated following similar procedures as outlined above. The methodology for isolating oil bodies from yeast has been documented (Ting et al., 1997, Journal Biol. Chem. 272:3699-3706).

The chemical and physical properties of the oil fraction may be varied in at least two ways. Firstly, different plant species contain oil bodies with different oil compositions. For example, coconut is rich in lauric oils ($C_{12}$), while erucic acid oils ($C_{22}$) are abundantly present in some *Brassica* spp. Secondly, the relative amounts of oils may be modified within a particular plant species by applying breeding and genetic engineering techniques known to the skilled artisan. Both of these techniques aim at altering the relative activities of enzymes controlling the metabolic pathways involved in oil synthesis. Through the application of these techniques, seeds with a sophisticated set of different oils are obtainable. For example, breeding efforts have resulted in the development of a rapeseed with a low erucic acid content (Canola) (Bestor, T. H., 1994, Dev. Genet. 15: 458) and plant lines with oils with alterations in the position and number of double bonds, variation in fatty acid chain length and the introduction of desirable functional groups have been generated through genetic engineering (Töpfer et al., 1995, Science, 268: 681-685). Using similar approaches a person skilled in the art will be able to further expand on the presently available sources of oil bodies. Variant oil compositions will result in variant physical and chemical properties of the oil bodies. Thus by selecting oilseeds or mixtures thereof from different species or plant lines as a source for oil bodies, or by mixing oil bodies obtained from various species or plant lines, a broad repertoire of emulsions with different textures, different properties that are beneficial to the skin and different viscosities may be acquired.

Formulating the Emulsion

The washed oil body preparation may be formulated into an emulsion using techniques known in the art. Preferably, at least one additional ingredient is added to the washed oil body preparation. The additional ingredient may be any chemical compound, including without limitation any acid or base, any organic or inorganic molecule, any ionic or non-ionic compound, any polar or non-polar molecule and any lipophilic or hydrophilic compound or, if more than one additional ingredient is added, any mixture of these compounds. The additional ingredient may be added in any desirable form, for example, the additional ingredient may be added as a solution, suspension, a gel, a crystal, a liquid or solid and the additional ingredient may be of any desirable viscosity. Quantities of the additional ingredient may be as desired and will depend on the formulation. The additional ingredient may upon formulation become associated with the oil bodies for example by the formation of non-covalent or covalent chemical bonds with the oil body, remain suspended in solution, or form a suspension in which the oil bodies are dispersed. The additional ingredient may also penetrate the phospholipid monolayer surrounding the oil body or the triacylglyceride matrix. In a further preferred embodiment the liquid phase is water. Water may be added either directly or through moisture associated with another ingredient. The final amount of water is not critical, however generally, the compositions will contain at least 1% of water and up to 99% water.

The concentration of oil bodies in the final product may be as desired. Typically the final concentration of oil bodies varies from about 0.0000001% (w/v) to about 99.9999999% (w/v). Preferably the final concentration of oil bodies will vary from about 1% (w/v) to about 99% (w/v) and more preferably from about 2% (w/v) to about 60% (w/v). The final formulation may be a liquid or a solid and of any viscosity but in general the final formulation will be of a consistency and viscosity compatible with its use as a pharmaceutical, personal care or food product.

In the course of the formulation process the oil bodies generally will stay intact, however depending on the ingredients that are added or the formulation process employed, the oil body structure may be more or less disrupted and the oil bodies may completely or partially disintegrate.

In the course of the formulation process any type of emulsion may be formed, including without limitation an oil-in-water emulsion, a water-in-oil emulsion, a multiple (e.g. double, tri-multiple, quarter-multiple and quinque-multiple etc.) emulsion, and reverse emulsion. The compositions of the present invention preferably will be in the form two phases where one phase is uniformly dispersed in the other phase, and resulting in a homogenous macroscopic appearance. Where compositions comprising two or more non-uniformly dispersed phases are formed they generally need to be shaken or stirred prior to use for the intended application.

The final formulation may be of any pH, but is generally of a pH compatible with intended application of the emulsion. Usually the formulation process will require mixing to provide an adequate emulsion and it may be necessary to apply heat, pressure, freezing, one or more cycles of freeze thawing or other physical forces to formulate the emulsion.

The emulsion formulations may be used for application to the surface area of the human body and may comprise a wide variety of additional components and may be formulated in a wide range of products including pharmaceutical, personal care and food products. The following optional ingredients and mixtures thereof represent non-limiting examples of ingredients that may be formulated with oil bodies.

Emulsion Stabilizing Agents

In a preferred embodiment of the present invention, the washed oil body preparation is stabilized so that an emulsion is obtained which may be stored for longer periods of time. It is preferred that the oil body formulation is stabilized so that a final product may be obtained which may be stored and preserved for longer periods of time. For the purpose of the present invention the term "stabilized oil body preparation" refers to an oil body preparation that is prepared so that the formulation does not undergo undesirable physical or chemical alterations when the oil body preparation is stored. The stabilization requirements may vary depending on the final product. For example personal care products are preferably stable for at least one year at room temperature while additionally being able to withstand short temperature fluctuations. Pharmaceutical formulations for example may in some cases be less stable as they may be stored at lower temperatures thereby preventing the occurrence of undesirable reactions.

In general stabilization techniques that may be used in accordance with the present invention include any and all methods for the preservation of biological material including the addition of chemical agents, temperature modulation based methodologies, radiation-based technologies and combinations thereof. In preferred embodiments small amounts of stabilizing chemical agents are mixed with the oil body formulation to achieve stabilization. These chemical agents include inter alia preservatives, antioxidants, acids, salts, bases, viscosity modifying agents, emulsifiers, gelling agents and mixtures thereof and may all be used to stabilize the oil body preparation.

Diagnostic parameters to assess the stability of the oil body preparation may be as desired and include all parameters indicative of undesirable qualitative or quantitative changes with respect to chemical or physical stability. Typical parameters to assess the oil body preparation over time include color, odor, viscosity, texture, pH and microbial growth, and enzymatic activity.

It is preferred that the oil body formulation is stabilized prior to the addition of further ingredients that may be used to prepare the final product. However it is nevertheless possible to formulate the final formulation using non-stabilized oil bodies and stabilize the final formulation.

Uses of the Emulsion Formulation

It is noted that the emulsions may be applied in compositions which vary considerably in physical properties and use. The types and quantities of ingredients used to prepare different products will depend on the desired use of the product and may be varied in accordance with practices well known to those of ordinary skill in the art of preparing emulsion formulations.

The particular product and the particular form in which the emulsion is applied, however is not of critical importance and may be as desired. It is to be clearly understood that the emulsion formulated with the washed oil body preparation may be applied in any product.

Food Products

In accordance with the present invention food products comprising oil bodies may be formulated. The food products that may be formulated in accordance with the present invention vary widely and include any plant seed or nut containing or derived food product. Food products that further may be prepared in accordance with the present invention include dairy products, for example cheese, milk, ice cream, and yoghurt; oil or fat based products such as margarine, butter, salad dressings, vinaigrettes, mustards, mayonnaises; grain or flour based products, for example bread, cake-mix, dough and pasta; pudding; baby formula; a beverage for example a juice or soft drink; condiments; texturing agents; soup; sauce; shortening; icing; and candy including chewing gum. Examples 17-21 describe in further detail the preparation of several food products containing oil bodies.

Personal Care and Dermatological Products

In accordance with the present invention it is also possible to produce of emulsions that are generally useful in topical application to the surface area of the human body, including skin, hair, teeth, nails and lips and includes personal care and dermatological products. For the purpose of the present application personal care products are meant to include all cosmetics, cosmeceuticals and beauty care products, all of which may be prepared in accordance with the present invention. Dermatological products, for the purpose of the present invention, are meant to include all products to treat or ameliorate skin conditions, abnormalities or diseases and contain one or more active ingredients capable of improving said condition, abnormality, disease. These products include any and all products that may be used to treat or ameliorate any phyiopathological conditions of the dermis or epidermis. Depending on the active ingredient which is formulated, the dermatological products of the present invention may be made available as a prescription drug or as an over-the-counter (OTC) product.

Personal care products which may be formulated in accordance with the present invention vary widely and include inter alia a skin care product, a hair care product, a beauty treatment product, a perfume, a bath and body product, a suncare product, a make-up and a toothpaste. These products may be prepared as formulations intended for specific use by individuals belonging to different age categories (babies, teenagers etc.), having different skin types (e.g. maturing, aged, dry, oily, mixed, combined or complexities thereof) or in accordance with the intended functionality of the product (for example products that prevent or reverse dehydration, replenish moisture, modulate pigmentation, prevent or reverse stretch marks, products for treatment or reversal of skin changes associated with aging such as wrinkles, blotches and atrophy or elastotic changes associated with intrinsic aging of the skin, as well as changes caused by external factors for example sunlight radiation, X-ray radiation, air pollution, wind, cold, dampness, dryness, heat, smoke and cigarette smoking)

Examples of skin care products which may be prepared using the emulsion formulations of the present invention include without limitation a skin cream; a facial cream; a cleanser, a toner; a day cream; a night cream; a day lotion; an eye cream; a facial mask (e.g. firming, moisturizing, purifying, deep-cleansing); an anti-aging cream; an anti-wrinkle cream; an anti-puffiness product; a cold weather cream; a foot cream; a facial scrub; an anti-acne product; a hand cream; an insect repellant formulation; or combinations thereof.

Hair care products that may be prepared in accordance with the present invention include for example a shampoo; a conditioner; a re-conditioner; a mousse; a gel; a hair spray; a hair mascara; a hot oil treatment product; a dye; a hair mask; a deep conditioning treatment product; a coloring product; a hair-repair product and permanent wave product or combinations of thereof.

Beauty treatment products include which may be prepared in accordance with the present invention include without limitation, a waxing product, a pedicure product, a manicure product, a facial product, a beauty lift product, a massage product and a aroma-therapy product; and combinations thereof.

Perfumes that may be prepared in accordance with the present invention include without limitation an eau de toilette; an eau de perfume; a perfumed bath, body lotion, shower gel, aftershave etc.; and combinations thereof.

Bath and body products which may be prepared in accordance with the present invention include for example a shower gel; including an exfoliating shower gel; a foaming bath product (e.g. gel, soap or lotion); a milk bath; a body wash; a soap including liquid and bar soap; a cleanser, including a gel cleanser, a liquid cleanser and a cleansing bar; a body lotion; a body spray, mist or gel; an essential lotion; a slimming lotion; bath effervescent tablets; a hand and nail cream; a bath/shower gel; a shower cream; a cellulite smoothing product; a deodorant; a dusting powder; an antiperspirant; a depilatory cream; a shaving product e.g. a shaving cream, a gel, a foams and an after-shave, after-shave moisturizer; and combinations thereof.

Suncare products which may be prepared in accordance with the present invention include a sunscreen; a sunblocker; an after sun lotion milks and gel; a burn lotion; a tanning lotion, spray and milk; a sunless self-tanning cream, spray and lotion; a combined sunscreen-insect repellant formulation and combinations thereof.

Make-up products that may be prepared in accordance with the present invention include a mascara (thickening, lengthening, waterproof); a blush (cream and powder); a lipstick; a foundation cream (stick or liquid); a foundation powder, a concealer; an eye shadow (cream and powder); an eye pencil; an eye liquid line; a bronzing powder; a lip pencil; a lip gloss; a lip conditioner; a make-up remover (e.g. eye make-up remover); a liquid lip color; a brow pencil; a lip balm; a nail polish (base and top coat and nail blush); and a combination thereof.

Dermatological compositions may also be prepared in accordance with the present invention. These dermatological products include products which may be used to treat or reverse skin changes associated with aging such as wrinkles, blotches and atrophy or elastotic changes associated with intrinsic aging of the skin as well as changes caused by external factors for example sunlight radiation; X-ray radiation; air pollution; wind; cold; dampness; dryness; heat; smoke and cigarette smoking; external infectious agents such as fungi and bacteria; and combinations thereof.

Additional skin conditions which may be treated include products to treat infectious and non-infectious skin diseases. Infectious diseases include for example impetigo and leprosy. Non-infectious skin diseases include without limitation autoimmune disorders such as psoriasis, cutaneous systemic lupus, cutaneous rheumatoid arthritis, allergic skin disorders (e.g. eczema), and pemphigoid.

Various manifestations of eczema, psoriasis and acne may also be treated using the emulsions of the present invention. Clinical manifestations of eczema which may be treated include inter alia atopic eczema; allergic contact dermatitis; irritant contact dermatitis; infantile seborrhoeic eczema; adult seborrhoeic eczema; varicose eczema and discoid eczema. The manifestations of psoriasis that may be treated include chronic, plaque-type psoriasis; guttate psoriasis; psoriatic erythoderma; and pustular psoriasis. Acne conditions which may be treated include superficial acne (acne vulgaris), low grade acne, pre-acne and acne lesions including comedones and micro comedones.

Still further examples of dermatological products which may be formulated in accordance with the present invention include without limitation products to treat hyper and hypopigmented skin, age spots, palmar or plantar hyperkeratosis, pruritis ichthyosis, Darier's disease, lichen simplex chronicus, dermatoses, xerosis, athlete's foot, herpes, herpes genitalis, warts, scabies, hemorrhoids, inflammatory dermatosis; xeroderma pigmentosum; skin cancers including basal cell carcinoma, malignant cell carcinoma, squamous cell carcinoma, malignant mellinoma, and AIDS-related Karposi sarcoma; premalignant skin lesions including actinic keratosis.

In order to prepare these personal care and dermatological products a wide variety of ingredients may be included in the oil body containing formulations. Non-limiting examples of ingredients that may be used in the preparation of personal care and dermatological products follow below.

Surfactants

The emulsions of the present invention may comprise surfactants (i.e. a surface active agent) generally in a concentration varying from about 0.01% (w/v) to about 40% (w/v), and more preferably from about 0.05% (w/v) to about 15% (w/v) and most preferably from about 0.1% (w/v) to about 10% (w/v) selected from the group consisting of anionics, cationics, nonionics and amphoterics or mixtures thereof. The surfactants used herein may act in a variety of ways including without limitation as a cleansing agent, detergent, emulsifier, wetting agent, foam booster, foam depressent, conditioner or germicide. A wide variety of surfactants may be used in the formulation of the products herein disclosed. They include the surfactants disclosed in U.S. Pat. No. 5,151,209 to McCall et al.; U.S. Pat. No. 5,151,210 to Steuri et al.; U.S. Pat. No. 5,120,532 to Wells et al.; and U.S. Pat. No. 5,635,469 to Fowler et al. all of which are incorporated herein by reference in their entirety.

Anionic surfactants that may be used in the formulation of the emulsions of the present invention include without limitation branched and unbranched alkyl and acyl hydrocarbon compounds, sodium dodecyl sulfate (SDS); sodium lauryl sulfate (SLS); sodium lauryl ether sulfate (SLES); sarconisate; fatty alcohol sulfates, including sodium, potassium, ammonium or triethanolamine salts of $C_{10}$ to $C_{18}$ saturated or unsaturated forms thereof; ethoxylated fatty alcohol sulfates, including alkyl ether sulfates; alkyl glyceryl ether sulfonate, alpha sulpho fatty acids and esters; fatty acid esters of isethionic acid, including Igepon A; acyl (fatty) N-methyltaurides, including Igepon T; dialkylsulfo succinate esters, including $C_8$, $C_{10}$ and $C_{12}$ forms thereof; Miranot BT also referred to as lauroamphocarboxyglycinate and sodium tridecath sulfate; N-acylated amino acids, such as sodium N-lauroyl sarconisate or gluconate; sodium coconut monoglyceride sulfonate; and fatty acid soaps, including sodium, potassium, DEA or TEA soaps.

Among the cationic surfactants that are useful are monoalkyl trimethyl quartenary salts; dialkyl dimethyl quartenary salts; ethoxylated or propoxylated alkyl quaternary amonium salts, also referred to in the art as ethoquats and propoquats; cetyl benzylmethylalkyl ammonium chloride; quaternized imidazolines, which are generally prepared by reacting a fat or fatty acid with diethylenetriamine followed by quaternization, and non-fat derived cationic polymers such as the cellulosic polymer, Polymer JR (Union Carbide).

Further useful cationic surfactants include lauryl trimethyl ammonium chloride; cetyl pyridinium chloride; and alkyltrimethylammonium bromide. Cationic surfactants are preferably used in the formulation of hair care products and more preferably in the formulation of rinses and conditioners.

Useful nonionic surfactants include polyethoxylated compounds and polypropoxylated products. Polyethoxylated and polypropoxylated compounds may be prepared by reacting fatty alcohols with ethylene oxide or glycol or by reacting fatty alcohols with propylene oxide or glycol. These materials have the general formula $R(X)_nOR'$ wherein R is H or $C_{10}$ to $C_{30}$ alkyl group, X is —$OCH_2CH_2$— (i.e. when derived from ethylene oxide or glycol) or —$OCH_2CHCH_3$— (i.e. when derived from propylene oxide or glycol), n is an integer from about 1 to 100, and R' is H or a $C_{10}$ to $C_{30}$ alkyl group. Polyethoxylated and polypropoxylated products may also be prepared by reacting fatty acids with ethylene oxide or glycol or propylene oxide or glycol respectively. These materials have the general formula $RCO(X)nOH$, wherein R is H or a $C_{10}$ to $C_{30}$ alkyl group, X is —$OCH_2CH_2$— (i.e. when derived from ethylene oxide or glycol) or —$OCH_2CHCH_3$— (i.e. when derived from propylene oxide or glycol) and n is an integer from about 1 to 100. Still other nonionic surfactants are the condensation products of a mixture of fatty acids and fatty alcohols reacting with ethylene glycol or oxide or propylene glycol or oxide. These materials have the general formula $RCO(X)_nR'$ wherein R and R' are H or $C_{10}$ to $C_{30}$ alkyl groups, X is —$OCH_2CH_2$— (i.e. when derived from ethylene oxide or glycol) or —$OCH_2CHCH_3$— (i.e. when derived from propylene oxide or glycol), and n is an integer from about 1 to 100.

Examples of ethoxylated and propoxylated non-ionic surfactants include ethoxylated anhydrohexitol fatty esters, for example Tween 20; mono- and diethanolamides; Steareth-20, also known as Volpo20; polyethylene glycol fatty esters (PEGs), such as PEG-8-stearate, PEG-8 distearate; block co-polymers, which are essentially combinations of hydrophylic polyethoxy chains and lipophilic polypropoxy chains and generically known as Poloaxamers.

Still other useful non-ionic surfactants include fatty esters of polyglycols or polyhydric alcohols, such as mono and diglyceride esters; mono- and di-ethylene glycol esters; diethylene glycol esters; sorbitol esters also referred to as Spans; sucrose esters; glucose esters; sorbitan monooleate, also referred to as Span80; glyceryl monostearate; and sorbitan monolaurate, Span20 or Arlacel 20.

Yet other useful nonionic surfactants include polyethylene oxide condensates of alkyl phenols and polyhydroxy fatty acid amide surfactants which may be prepared as for example disclosed in U.S. Pat. No. 2,965,576 to E. R. Wilson.

Examples of amphoteric surfactants which can be used in the compositions of the present invention include the betaines, which can be prepared by reacting an alkyldimethyl tertiary amine, for example lauryl dimethylamine with chloroacetic acid. Betaines and betaine derivatives include higher alkyl betaine derivatives including coco dimethyl carboxymethyl betaine; sulfopropyl betaine; alkyl amido betaines; and cocoamido propyl betaine. Sulfosultaines which may be used include for example, cocoamidopropyl hydroxy sultaine. Still other amphoteric surfactants include imidazoline derivatives and include the products sold under the trade name "Miranol" described in U.S. Pat. No. 2,528,378 which is incorporated herein by reference in its entirety. Still other amphoterics include phosphates for example, cocamidopropyl PG-dimonium chloride phosphate and alkyldimethyl amine oxides.

Moisturizers

Another ingredient which may be formulated with the washed oil body emulsions of the present invention is a moisturizer. As used herein a "moisturizer" is an ingredient which promotes the retention of water to the surface area of the human body, including hair and skin. The term moisturizer as used herein includes both components which deliver water to the skin, also commonly referred to in the art as "humectant", and components which prevent the loss of water from the skin, also commonly referred to in the art as "occlusive". The moisturizer will generally comprise from about 0.1% (w/v) to about 99% (w/v), more preferably from about 0.5% (w/v) to about 50% (w/v), and most preferably from about 1% (w/v) to about 40% (w/v) of the final composition. Although the ingredients mentioned herein are generally defined as moisturizers they may also possess other properties such as emolliency or other conditioning properties.

Moisturizers that may used in accordance with the present invention include without limitation polyhydroxy alcohols, including butylene glycol, hexylene glycol, propylene glycol, sorbitol and the like; lactic acid and lactate salts, such as sodium or ammonium salts; $C_3$ and $C_6$ diols and triols including hexylene glycol, 1,4 dihydroxyhexane, 1,2,6-hexane triol; aloe vera in any of its forms, for example aloe vera gel; sugars and starches; sugar and starch derivatives, for example alkoxylated glucose; hyaluronic acid; lactamide monoethanolamine; acetamide monoethanolamine; glycolic acid; alpha and beta hydroxy acids (e.g. lactic, glycolic salicylic acid); glycerine; pantheol; urea; vaseline; natural oils; oils and waxes (see: the emollients section herein) and mixtures thereof. Moisturizers are generally recognized in the art of personal care and skin care and in principle any moisturizer may be formulated in the presence of oil bodies.

Emollients

A further ingredient which may be formulated with the oil body compositions of the present invention is an emollient. Emollients typically comprise between from about 0.01% to about 25%, preferably from about 0.05% to about 15% and more preferably from about 0.1% to about 10%. Emollients are used to add or replace lipids and natural oils to the surface area of the human body. The term emollient as used herein is intended to include conventional lipids (for example, oils, waxes, lipids and other water insoluble components) and polar lipids (lipids which have been modified in order to increase water solubility typically through esterfication of a lipid to a hydrophylic moiety for example hydroxy groups, carbonyl groups and the like). Emollients which may be used in the present invention are preferably selected from the group consisting of natural oils and preferably plant-derived and essential oils, esters, silicone oils, polyunsaturated fatty acids (PUFAs), lanoline and its derivatives and petrochemicals.

Natural oils which may be used in accordance with the present invention may be obtained from sesame; soybean; apricot kernel; palm; peanut; safflower; coconut; olive; cocoa butter; palm kernel; shea butter; sunflower; almond; avocado; borage; camauba; hazel nut; castor; cotton seed; evening primrose; orange roughy; rapeseed; rice bran; walnut; wheat germ; peach kernel; babassu; mango seed; black current seed; jojoba; macademia nut; sea buckthorn; sasquana; tsubaki; mallow; meadowfoam seed; coffee; emu; mink; grape seed; thistle; tea tree; pumpkin seed; kukui nut; and mixtures thereof.

Esters which may be used include $C_8$-$C_{30}$ alklyl esters of $C_8$-$C_{30}$ carboxylic acids; $C_1$-$C_6$ diol monoesters and diesters of $C_8$-$C_{30}$ carboxylic acids; $C_{10}$-$C_{20}$ alcohol monosorbitan esters, $C_{10}$-$C_{20}$ alcohol sorbitan di- and tri-esters; $C_{10}$-$C_{20}$ alcohol sucrose mono-, di-, and tri-esters and $C_{10}$-$C_{20}$ fatty alcohol esters of $C_2$-$C_6$ 2-hydroxy acids and mixtures thereof. Examples of these materials include isopropyl palmitate; isopropyl myristate; isopropyl isononate; $C_{12}/C_{14}$ benzoate ester (also known as Finesolve); sorbitan palmitate, sorbitan oleate; sucrose palmitate; sucrose oleate; isostearyl lactate; sorbitan laurate; lauryl pyrrolidone carboxylic acid; panthenyl triacetate; and mixtures thereof.

Further useful emollients include silicone oils, including non-volatile and volatile silicones. Examples of silicone oils that may be used in the compositions of the present invention are dimethicone; cyclomethycone; dimethycone-copolyol; aminofunctional silicones; phenyl modified silicones; alkyl modified silicones; dimethyl and diethyl polysiloxane; mixed $C_{10}$-$C_{30}$ alkyl polysiloxane; and mixtures thereof. Additionally useful silicones are described in U.S. Pat. No. 5,011,681 to Ciotti et al., incorporated by reference herein.

A yet further useful group of emollients which may be formulated in accordance with the present invention in the presence of oil bodies are lanoline and lanoline derivatives for example lanoline esters.

Petrochemicals which may be used as emollients in the compositions of the present invention include mineral oil; petrolatum; isohexdecane; permethyl 101; isododecanol; $C_{11}$-$C_{12}$ Isoparrafin, also known as Isopar H).

Among the waxes which may be included in the compositions of the present invention are animal waxes such as beeswax; plant waxes such as camauba wax, candelilla wax, ouricurry wax, Japan wax or waxes from cork fibers or sugar cane. Mineral waxes, for example paraffin wax, lignite wax, microcrystalline waxes or ozokerites and synthetic waxes may also be included.

It is noted that although the ingredients mentioned herein are generally defined as emollients they may also possess other properties such as moisturization or other conditioning properties (see under: Moisturizers, hereinbefore mentioned).

Fragrances

A further ingredient that may be formulated with the washed oil body compositions in accordance with the present invention is a fragrance. Typically a fragrance comprises between about 0.0001% (v/v) and about 25% (v/v) of the final composition, more preferably between about 0.001% (v/v) and 10% (v/v) and most preferably between 0.01% (v/v) and 5% (v/v) of the final composition. For the purpose of the present application the term "fragrance" is meant to encompass any component reacting with the human olfactory sites and imparting a pleasurable odor, essence or scent. Fragrances that may be used in accordance with the present invention include any synthetic as well as natural fragrance and mixtures thereof. Typically a multiplicity of fragrances are used to achieve the desired effect. Those of skill in the art further recognize the terms "top note" (i.e. fragrances having a high vapor pressure), "middle note" (i.e. fragrance having a medium vapor pressure) and "base note" (i.e. fragrances having a low vapor pressure). Recognizing that categorization within these classes may depend to some extent on the fragrance formulator, the emulsions of the present invention may comprise any top note, middle note and base note fragrance. A further way of classifying fragrances is in accordance with generally recognized scents they produce. Descriptors used by those skilled in the art of fragrances are inter alia "rose", "floral", "green", "citrus", "spicy", "honey", "musk", "herbal", "jasmin", "lilac", lily of the valley", "orange", "peach", "oriental", "watermelon" "chypre" and "lemon", "woody", "fruity" all of which fragrances thus classified may be formulated with the emulsions of the present invention.

Fragrances that may be used in accordance with the present invention include linear and cyclic alkenes (i.e. terpenes); primary, secondary and tertiary alcohols; ethers; esters; ketones; nitrites; and saturated and unsaturated aldehydes; or mixtures thereof.

Examples of synthetic fragrances that may be used in accordance with the present invention include without limitation acetanisole; acetophenone; acetyl cedrene; methyl nonyl acetaldehyde; musk anbrette; heliotropin; citronellol; sandella; methoxycitranellal; hydroxycitranellal; phenyl ethyl acetate; phenylethylisobutarate; gamma methyl ionone; geraniol; anethole; benzaldehyde; benzyl acetate; benzyl salicate; linalool; cinnamic alcohol; phenyl acetaldehyde; amyl cinnamic aldehyde; caphore; p-tertiairy butyl cyclohexyl acetate; citral; cinnamyl acetate; citral diethyl acetal; coumarin; ethylene brasslate; eugenol; 1-menthol; vanillin; and mixtures thereof.

Examples of natural fragrances of use herein include without limitation lavandin; heliotropin; sandlewood oil; oak moss; pathouly; ambergris tincture; ambrette seed absolute; angelic root oil; bergamont oil; benzoin Siam resin; buchu leaf oil; cassia oil; cedarwood oil; cassia oil; castoreum; civet absolute; chamomile oil; geranium oil; lemon oil; lavender oil; Ylang Ylang oil; and mixtures thereof.

A list of generally used fragrance materials can be found in various reference sources, for example, "Perfume and Flavor Chemicals", Vols. I and II; Steffen Arctander Allured Pub. Co. (1994) and "Perfumes: Art, Science and Technology"; Muller, P. M. and Lamparsky, D., Blackie Academic and Professional (1994) both incorporated herein by reference.

Active Ingredients

In accordance with the present invention a wide variety of active ingredients may be formulated with the washed oil bodies of the present invention. The terms "actives", "active agent" and "active ingredient" as used herein refers to a chemical compound capable of enhancing or improving the physical appearance, health, fitness or performance of the surface area of the human body, including the skin, hair, scalp, teeth and nails. The amount of active formulated will depend on the desired effect and the active that is selected. In general, the amount of active varies from about 0.0001% (w/v) to about 50% (w/v). More preferably however the amount of active in the final composition will vary from about 0.01% (w/v) to about 20% (w/v) and most preferably from about 0.1% (w/v) to about 10% (w/v). The actives may be formulated into the washed oil body formulation in any desired manner (e.g. mixed, stirred) under any desired condition (e.g. heated; under pressure) and in any desired form (e.g. a liquid, solid, gel, crystal, suspension). Depending on the chemical nature of the active and the formulation methodology, the active may become incorporated in the final formulation in a variety of ways, for example the active ingredient may remain suspended in solution, or form a suspension in which the oil bodies are dispersed, or the active ingredients may penetrate the phospholid mono layer surrounding the oil body or the triacyl glyceride matrix of the oil body. The active also may be associated with the oil bodies. As used herein the term "associated with the oil bodies" refers to any specific interaction between the active ingredient and the oil bodies including any interaction which involves the formation of a covalent bond between the oil body and the active ingredient as well as any interaction which involves the formation of a non-covalent bond, for example an ionic bond, between the oil body and the active ingredient. The active agent may directly associate with the oil body or indirectly via one or more intermediate molecules. As used herein "crosslinker" or "crosslinking agent" means any single molecule or plurality of inter-linked molecules capable of indirectly associating the active ingredient with the oil body. Oil bodies crosslinked to actives may comprise a plurality of covalent and non-covalent interactions or mixtures thereof. Generally the reaction to cross-link the active ingredient to the oil body will involve the oleosin protein or oil body phospholipids as reactive groups.

Particularly useful crosslinking agents in this regard are those crosslinking agents which are capable of reacting with oleosin proteins. These include homobifunctional cross-linkers (i.e. having two identical reactive groups) including homobifunctional imido esters and homobifunctional N-hydroxysuccinimidyl (NHS) esters; and heterobifunctional crosslinkers (i.e. having two different reactive groups), including crosslinkers comprising an amine reactive group; sulfhydryl reactive N-hydroxysuccinimidyl esters such as maleimides pyridyl disulfides and alpha-haloacetyls; or a carboxyl reactive group. Non-limiting examples of crosslinking agents are inter alia dimethyladipimidate, discuccinidyl glutarate; succinimidyl 4-(N-maleimidomethyl) cyclo hexane-1-carboxylate, bismaleimidohexane; sulfosuccinimidyl (4-iodoacetyl)-aminobenzoate; N-succinimidyl 3-(2-pyridyldithione)-propionate; and 1-ethyl-3(3-dimethylaminopropyl)-carbodiimide; glutaraldehyde; and glyoxal.

Other useful crosslinkers include photoreactive crosslinkers such as arylazide derived compounds, for example p-azidophenyl glyoxal monohydrate; n-hydrosulfo-succinimidyl 4-azidobenzoate; and sulfosuccinimidyl (4-azidophenyldithio) propionate.

Still other components that are particularly useful as crosslinkers for the association of active ingredients to oil bodies are biotin-streptavidin and biotin-avidin crosslinkers (available from Pierce). By linking the active ingredient to streptavidin or avidin and biotinylating the oil bodies, or visa versa, biotinylating the active ingredient and linking avidin or streptavidin to the oil bodies, the active ingredient is crosslinked to the oil bodies via two inter-linked molecules. Still further useful cross-linking compounds which may be used in accordance with the present invention are one or more inter-linking antibodies. Particularly useful in this regard are antibodies with an affinity to oleosins. Combined inter-linked antibody-avidin-biotin or antibody-streptavidin-biotin crosslinkers may also be used in accordance with the present invention. Additional cross-linking strategies for associating compounds to oil bodies are described in PCT Patent Application WO 98/27115 to Moloney et al. which is incorporated by reference herein.

Non-limiting examples of actives which may be formulated in the presence of oil body emulsions are listed below. The actives are categorized in various classes however this classification is not intended to limit the actives in any way to only to those actives belonging to the categories herein mentioned.

Sunscreen Actives

A wide variety of sunscreen actives are useful herein. The exact amount and type of sunscreen that is used depends on the level of photoprotection that is desired. Generally any agent offering protection against ultraviolet radiation by absorbing, scattering or reflecting the ultraviolet radiation may be used herein. The sunscreen agents used herein may offer protection against one or more of the following forms of sunlight radiation UVA, UVB, UVC, visible light and infrared radiation. Generally the sunprotection factor (SPF) in the final formulation varies between 2 and 30, although products with SPFs up to 100 may be formulated. The sunscreen used herein may offer chemical or physical photoprotection.

Sunscreens which may be used in accordance with the present invention include those selected from the group comprising amino benzoic acid and derivatives, such as para-amino benzoic acid (PABA), glyceryl-PABA (Lisadimate), Padimate O, Roxadimate; anthrinalates, including methylanthrynilate; benzophenones, including dioxybenzone, oxybenzone and sulisobenzone, 3-benzophenone (Uvinul M40) 4-N,N-dimethylaminobenzoic acid ester with 2,4-dihydroxybenzophenone; camphor derivatives including 3-(4-methylbenzylidene) camphor, 3-benzylidene camphor; cinnamates including DEA-p-methoxycinnamate, ethyl-hexyl p-methoxy cinnamate, octocrylene, octyl methoxy cinnamate (Parasol MCX); dibenzoyl methanes including butylmethoxydibenzoylmethane (Parsol 1789), salicylates including, homomenthyl salicylate, octyl salicylate, trolamine methyl salicylate; metal oxides including titanium dioxide, zinc oxide and iron oxide; 2-phenylbenzimidazole-5-sulfonic acid; 4,4-methoxy-t-butyldibenzoylmethane; and mixtures thereof.

Further non-limiting examples of sunscreens useful in accordance with the present invention are described in U.S. Pat. No. 5,087,445 to Haffey et al., U.S. Pat. No. 5,073,372 to Turner et al. and U.S. Pat. No. 5,160,731 to Sabatelli et al., all of which are incorporated herein by reference in their entirety.

Anti-Wrinkle and Anti-Aging Actives

The oil body emulsions of the present invention also may be advantageously formulated with anti-wrinkle and anti-aging actives. These agents include without limitation hydroxy acids including $C_2$-$C_{30}$ alpha-hydroxy acids such as glycolic acid, lactic acid, 2-hydroxy butanoic acid, malic acid, citric acid tartaric acid, alpha-hydroxyethanoic acid, hydroxycaprylic acid and the like; beta hydroxy acids including salicylic acid and polyhydroxy acids including gluconolactone (G4); and mixtures of these acids. Further anti-wrinkle agents include retinoic acid, gamma-linolenic acid; fruit acids, sugar cane extract and glycomer in cross-linked alpha nutrium; and mixtures thereof. Skin peel agents for example phenol, phytic acid and acetic acid may also be used in accordance with the present invention. Salicylic acid, lactic acid and glycolic acid are preferred for use herein.

Whitening and Bleaching Actives

Whitening and bleaching agents include hydroquinone and derivatives; kojic acid; lactic acid; ascorbyl acid and derivatives such as magnesium ascorbyl phosphate; arbutin; and licorice root. Hydroquinone and derivatives are preferred for use herein.

Sunless Tanning Actives

Sunless tanning actives include dihydroxyacetone (DHA); glyceryl aldehyde; tyrosine and tyrosine derivatives such as malyltyrosine, tyrosine glucosinate, and ethyl tyrosine; phospho-DOPA, indoles and derivatives; and mixtures thereof.

Antimicrobial Actives

Antimicrobials that may be used in accordance with the present invention include all antibiotics, antimicrobial agents and antimicrobial peptides. Antibiotics that may be used include inter alia dermatologically acceptable salts of tetracylin and tetracyclin derivatives, gentamycin, kanamycin, streptomycin, neomycin, capreomycin, lineomycin, paromomycin, tobramycin, erythromycin, triclosan, octopirox, parachlorometa xylenol nystatin, tolnafiate, miconazole hydrochloride, chlorhexidine gluconate, chlorhexidin hydrochloride, methanamine hippurate, methanamine mandelate, minocycline hydrochloride, b-lactam derivatives such as aminopenicillin and mixtures thereof. Preferred for use herein are chlorhexidin gluconate and tricolosan.

Anti microbial agents that may be used in accordance with the present invention include for example benzoyl peroxide and salicylic acid.

Antimicrobial peptides useful herein are for example magainin, nicin and cecropin.

Anti-Acne Actives

Anti-actives that may be used in accordance with the present invention include without limitation keratolytic agents including lactic acid, pyruvic acid, salicylic acids, urea and N-acetylcysteine; retinoids, and retinoid analogs such as tretinoin, cis and trans retinoic acid, retinol and retinol palmitate, isotretinoin-13-cis-retinoic acid; antibiotics and antimicrobial agents such as tetracycline, erythromycin, minocycline, clindamycin, trimethoprim-sulphamethazole and antimicrobial peptides (nicin, for example); steroids, such as hydrocortisone; gamma-linolenic acid and mixtures thereof. Further anti-acne actives that may be used include without limitation benzoyl peroxide; alpha and beta hydroxy acids; sulfacteamide and sulfur and mixtures thereof. Preferably used herein are salicylic acid, benzoyl peroxide and retinoids.

Anti-Psoriasis Actives

Anti-psoriasis actives preferred for use in the present invention include without limitation salicylic acid; mometasone furoate; steroids including corticosteroids such as cortisone and oluxclobetasol propionate; 5-fluorouracil; epinephrine; anthralin; vitamin D3 analogs, such as calcipotriene; methotrexate; masprocol; trimethaxate gluconate; retinoids; cyclosporin; paclitaxel; 5-amino levulinic acid; bergasol; tin-ethyl etio purpurin; benzoporphyrin derivatives; antibodies, such as ABX-IL8 antibody, CD11a monoclonal antibody and ICM3 monoclonal antibody; enzyme inhibitors, including tryptase inhibitor and phospholipase A-2 inhibitors; angiogenesis blocking agents; T-cell blocking agents and mixtures thereof.

Anti Eczema Actives

Anti-eczema actives useful herein include urea; evening primrose oil; plant extracts; hydrocortisone; an immunomodulator; tar combined with fatty acids obtained from banana; and mixtures thereof.

Topical Anesthetic Actives

Topical anesthetic actives that may be used in accordance with the present invention include tetracaine, lidocaine, editocaine, bupivacaine, pramoxine; and mixtures thereof.

Antiinflammatory Actives

Antiinflammatory actives useful in accordance with the present invention include steroidal actives such as hydrocortisone as well as non-steroidal actives including propionic derivatives; acetic acid derivatives; biphenylcarboxylic acid derivatives; fenamic acid derivatives; and oxicams. Examples of antiinflammatorty actives include without limitation acetominaphen, oxaprozin, pranoprofen, benoxaprofen, bucloxic acid; and mixtures thereof.

Vitamin Actives

Vitamin actives which may be used in accordance with the present invention include vitamin A and derivatives, including retinoic acid, retinyl aldehyde, retin A, retinyl palmitate and beta-carotene; vitamin B (panthenol, provitamin B5, panthenic acid, vitamin B complex factor); vitamin C (ascorbic acid and salts thereof) and derivatives such as ascorbyl palmitate; vitamin E including its individual constituents alpha-, beta-, gamma-, delta-tocopherol and cotrienols and mixtures thereof and vitamin E derivatives including vitamin E palmitate, vitamin E linolate and vitamin E acetate; vitamin K and derivatives; vitamin Q (ubiquinone) and mixtures thereof.

Protein Actives

One particularly preferred class of actives which may be used in accordance with the present invention are proteins and peptides. Proteins may be formulated in the emulsions of the present invention in any desired manner, however one particularly advantageous way in which proteins may be included in emulsions of the subject invention, is through construction of oleosin gene fusions as detailed in PCT Patent Application Publication No. WO 96/21029 and U.S. Pat. No. 5,650,554 to Moloney both of which are incorporated by reference herein. Briefly stated, PCT Patent Application No.

WO 96/21029 and U.S. Pat. No. 5,650,554 disclose a method of producing proteins and peptides as fusion proteins with oleosins. These fusion proteins are created by genetically linking the gene encoding oleosin to a gene encoding a peptide or protein of interest. Expression of the fusion gene, in for example an oilseed plant, results in synthesis of a fusion protein which is then targeted to the oil body.

In principle any desired protein or peptide may be produced using this technology and oil bodies comprising these recombinant proteins may be incorporated in the emulsions of the present invention. Proteins and peptides which may be used in accordance with the present invention include enzymes such as proteases (e.g. bromelain, papain, collagenase, elastase), lipases (e.g. phospholipase C), esterases, glucosidases, exfoliating enzymes; antibodies and antibody derived actives, such monoclonal antibodies, polyclonal antibodies, single chain antibodies and the like; reductases; oxidases; peptide hormones; natural structural skin proteins, such as elastin, collagen, reticulin and the like; growth factors such as platelet derived growth factor (PDGF) and epidermis derived growth factor (EGF); anti-oxidants such as superoxide dismutase, catalase and glutathione; free-radical scavenging proteins; DNA-repair enzymes, for example T4 endonuclease 5 and P53; antimicrobial peptides, such as magainin and cecropin; a milk protein; a silk protein or peptide; and any active fragments, derivatives of these proteins and peptides; and mixtures thereof.

In accordance with the present invention in a particularly preferred embodiment the protein is a redox protein such as a thioredoxin or a thioredoxin reductase.

Miscellaneous Active Ingredients

Further active ingredients that may be formulated in accordance with the present invention include an amino acid and amino acid derivative; an insect repellant; a fungicide; an anti-viral agent; an anti-cancer agent; a plant extract; an anti-hemorrhoid compound; an anti-dandruff compound; a hair-growth stimulating compound; a hair loss stimulating compound; a nucleic acid (DNA, RNA and derivatives) and mixtures thereof.

Miscellaneous Ingredients

A variety of additional ingredients may be formulated into the emulsion formulations of the present invention. These ingredients have been categorized for convenience reasons however this classification is not intended to be limiting to those particular classes or ingredients within those classes Chelating Agents Chelating agents, capable of binding metal ions, such as tartaric acid, EDTA, citric acid, alkali metal citrates, pyrophosphate salts or anionic polymeric polycarboxylates may be also included in the emulsion formulation as desired.

Pigments

Pigments may be also be included in the formulation of the present invention. The pigments that may be used may be white or colored, inorganic or organic and/or paerlescent. These pigments comprise titanium dioxide, zinc oxide, zirconium dioxide, black, yellow, red and brown iron oxides, cerium dioxide, chromium oxide, ferric blue, carbon black, barium, strontium, calcium and aluminum lakes and mica coated with titanium oxide or with bismuth oxide.

Lipids

Lipids that may be used herein include inter alia triacyl glycerides; fatty acids such as gamma-linolenic acid; waxes; cholesterol; sphingolipids; ceramides; phospholipids and mixtures thereof.

Inorganic Salts

Inorganic salts that may be used herein include without limitation aluminum zirconium chloride; aluminum chlorohydroxide; zinc oxide; talc; borax; alum; ammonium acetate. These salts are particularly useful in preparing antiperspirants and deodorants.

Anti-Oxidants

Anti-oxidants that may be incorporated herein include natural anti-oxidants prepared from plant extracts including without limitation extracts that may be obtained from aloe vera; cryocytol; avocado; chamomile; echinacea; ginko biloba; ginseng; green tea; heather; jojoba; lavender; lemon grass; licorice; mallow; oats; peppermint; St. John's wort; willow; wintergreen; wheat wild yam extract; marine extracts; and mixtures thereof. Further anti-oxidants that may be used include vitamins, including vitamin C, vitamin E and vitamin E mimetics; alpha-lipoic acid; coenzyme Q; glutathione; superoxide dismutase; and mixtures thereof.

Pharmaceutical Products

In accordance with the present invention pharmaceutical products comprising oil bodies may be formulated. The pharmaceutical products that may be formulated in accordance with the present invention vary widely and may be used to treat a variety of diseases and conditions and will contain at least one pharmaceutically active ingredient. Pharmaceutically active ingredients and compounds are generally art recognized. The pharmaceutically active ingredient can be any ingredient one wishes to deliver to treat a disease or condition. In preferred embodiments the pharmaceutical product is topically or orally applied.

Oil Bodies Comprising Thioredoxin or Thioredoxin Reductase

In accordance with the present invention, in a preferred embodiments formulations comprising oil bodies and thioredoxin or thioredoxin reductase may be prepared. The thioredoxin or thioredoxin reductase may be formulated with oil bodies using any formulation methodology known to the art, including those hereinbefore mentioned.

Accordingly the present invention provides a method of preparing an emulsion formulation comprising 1) obtaining oil bodies from a cell; 2) washing the oil bodies; and 3) formulating the washed oil bodies with thioredoxin or thioredoxin reductase.

In a preferred embodiment thioredoxin or thioredoxin reductase are produced in a cell. The thioredoxin or thioredoxin reductase are obtained from the cell by association of the thioredoxin or thioredoxin reductase with oil bodies through an oil body targeting protein capable of association with the oil body and the thioredoxin or thioredoxin reductase. The oil bodies associated with the thioredoxin or thioredoxin reductase are then used to prepare an emulsion.

Accordingly the present invention further provides a method for preparing an emulsion formulation comprising oil bodies said method comprising:

(a) producing in a cell a thioredoxin or thioredoxin reductase;

(b) associating said thioredoxin or thioredoxin reductase with oil bodies through an oil body targeting protein capable of associating with said thioredoxin or thioredoxin reductase and said oil bodies;

(c) obtaining said oil bodies associated with said thioredoxin or thioredoxin reductase;

(d) washing the oil bodies to obtain a washed oil body preparation comprising thioredoxin or thioredoxin reductase; and (e) formulating said washed oil bodies associated with thioredoxin or thioredoxin reductase into en emulsion.

In a preferred embodiment the thioredoxin or thioredoxin reductase are produced in the same cell as the cell from which the oil bodies are obtained.

The term "oil body targeting protein" as used herein refers to any protein, protein fragment or peptide capable of association with an oil body. In accordance with the present invention the oil body targeting protein that is used is capable of association with the thioredoxin or thioredoxin reductase. The term "capable association with an oil body targeting protein" as used herein refers to covalent interactions (i.e. protein fusions) as well as non-covalent interactions between the oil body targeting protein and the thioredoxin or thioredoxin reductase. In preferred embodiments of the present invention the oil body targeting protein used is an oil body protein for example a caleosin or oleosin. The oil body targeting protein may be produced recombinantly in any cell including any animal cell, plant cell, algae cell, bacterial cell or fungal cell or may be prepared synthetically. In preferred embodiments the oil body targeting protein is produced in plant cells and more preferably in plant seed cells. In particularly preferred embodiments the oil body targeting protein is produced in cells comprising oil bodies. These embodiments are preferred since a single isolation process may be used to obtain oil bodies comprising the oil body targeting protein.

In accordance with the present invention the oil body targeting protein and the thioredoxin or thioredoxin reductase may be produced in the same cell or in different cells. In preferred embodiments the oil body targeting protein that is used is an oil body protein. For the purpose of the present invention the term "oil body protein" is intended to mean any protein naturally present in cells comprising oil bodies and having the capability of association with oil bodies including any oleosin or a caleosin. In embodiments of the present invention in which an oil body protein is used, the thioredoxin or thioredoxin reductase are preferably covalently fused to the oil body protein and consequently the thioredoxin or thioredoxin reductase and the oil body binding protein are produced in the same cell. Accordingly the present invention provides a method for the preparation of an emulsion formulation comprising:

a) introducing into a cell a chimeric nucleic acid sequence comprising:

1) a first nucleic acid sequence capable of regulating transcription in said cell operatively linked to;

2) a second nucleic acid sequence encoding a recombinant fusion polypeptide comprising (i) a first nucleic acid sequence encoding a sufficient portion of an oil body protein to provide targeting to an oil body linked in reading frame to (ii) a second nucleic acid sequence encoding a thioredoxin or thioredoxin reductase operatively linked to;

3) a third nucleic acid sequence capable of terminating transcription in said cell;

b) growing said cell under conditions to permit expression of said thioredoxin or thioredoxin reductase in a progeny cell comprising oil bodies;

c) isolating said oil bodies comprising said thioredoxin or thioredoxin reductase from said progeny cell;

d) washing said oil bodies to obtain a washed oil body preparation comprising thioredoxin or thioredoxin reductase; and e) formulating said oil bodies comprising said thioredoxin or thioredoxin reductase into an emulsion.

The term "nucleic acid" as used herein refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic acids (RNA) or deoxyribonucleic acids (DNA) and may contain naturally occurring bases including adenine, guanine, cytosine, thymidine and uracil. The sequences also may contain modified bases such as xanthine, hypoxanthine, 2-aminoadenine, 6-methyl, 2-propyl and other alkyl adenines, 5-halo-uracil, 5-halo cytosine, 6-aza uracil, 6-aza cytosine and 6-aza thymine, pseudo uracil, 4-thiouracil, 8-halo adenine, 8-amino adenine, 8-thiol-adenine, 8-thio-alkyl adenines, 8-hydroxyl adenine and other 8-substituted adenines, 8-halo guanines, 8 amino guanine, 8 thiol guanine, 8-thioalkyl guanines, 8 hydroxyl guanine and other 8-substituted guanines, other aza and deaza uracils, thymidines, cytosines, adenines, or guanines, 5-trifluoromethyl uracil and 5-trifluoro cytosine.

The nucleic acid sequence encoding the oil body targeting protein that may be used in accordance with the present invention may be any nucleic acid sequence encoding an oil body targeting protein, protein fragment or peptide capable of association with a thioredoxin or thioredoxin reductase. The nucleic acid sequence encoding the oil body targeting protein may be synthesized or obtained from any biological source.

In one embodiment the oil body targeting protein is an immunoglobulin or an immunoglobulin derived molecule, for example a bispecific single chain antibody. The generation of single chain antibodies and bi-specific single chain antibodies is known to the art (U.S. Pat. Nos. 5,763,733; 5,767,260 and 5,260,203). Nucleic acid sequences encoding single chain antibodies functioning as oil body targeting proteins may be prepared from hybridoma cell lines expressing monoclonal antibodies raised against an oleosin as described by Alting-Mees et al (2000) IBC's Annual International Conference on Antibody Engineering, Poster #1. In order to attain specificity for the thioredoxin or thioredoxin reductase a nucleic acid sequence encoding a second single chain antibody prepared from a monoclonal raised against a thioredoxin or thioredoxin reductase may be prepared and linked to the anti-oleosin single chain antibody. In this embodiment the oil body associates with the thioredoxin or thioredoxin reductase through non-covalent interactions of the oil body targeting protein with the thioredoxin or thioredoxin reductase and the oil body. Alternatively the thioredoxin or thioredoxin reductase may be prepared as a fusion protein with an oil body targeting protein. For example a nucleic acid sequence encoding a single chain antibody raised against an oleosin may be fused to a nucleic acid sequence encoding a thioredoxin or thioredoxin reductase.

Non-immunoglobulin-based oil body targeting proteins capable of association with a thioredoxin or thioredoxin reductase may be discovered and prepared using for example phage display techniques (Pharmacia Biotech Catalogue Number 27-9401-011 Recombinant Phage Antibody System Expression Kit).

Oil body targeting proteins may also be chemically modified. For example oleosins may be modified by changing chemical modification of the lysine residues using chemical agents such as biotinyl-N-hyrdoxysuccinimide ester resulting a process referred to as biotinylation. Conveniently this is accomplished by in vitro biotinylation of the oil bodies. In vivo biotinylation may be accomplished using the biotinylation domain peptide from the biotin carboxy carrier protein of *E. coli* acetyl-CoA carboxylase (Smith et al. (1998) Nucl. Acids. Res. 26: 1414-1420). Avidin or streptavidin may subsequently be used to accomplish association of thioredoxin or thioredoxin reductase with the oil body.

In a preferred embodiment the oil body targeting protein is an oil body protein such as for example an oleosin or a caleosin or a sufficient portion derived thereof capable of targeting to an oil body. Nucleic acid sequences encoding oleosins are known to the art. These include for example the Arabidopsis oleosin (Van Rooijen et al (1991) Plant Mol. Bio. 18:1177-1179); the maize oleosin (Qu and Huang (1990) J. Biol. Chem. Vol. 265 4:2238-2243); rapeseed oleosin (Lee and Huang (1991) Plant Physiol. 96:1395-1397); and the carrot oleosin (Hatzopoulos et al (1990) Plant Cell Vol. 2, 457-467.). Caleosin nucleic acid sequences are also known to the art (Naested et al (2000) Plant Mol Biol. 44(4):463-476; Chen et al (1999) Plant Cell Physiol. 40(10):1079-1086). In preferred embodiments of the invention the thioredoxin or thioredoxin reductase is fused to the oil body protein. This is further described in U.S. Pat. No. 5,650,554, which is incorporated herein by reference in its entirety. In such an embodiment the oil bodies and the thioredoxin or thioredoxin reductase can conveniently be isolated in one step. The thioredoxin or thioredoxin reductase polypeptide may be fused to the N-terminus as well as to the C-terminus of the oil body protein (as described in: van Rooijen and Moloney (1995) Plant Physiol. 109:1353-1361) and fragments of the oil body protein such as for example the central domain of an oleosin molecule, or modified versions of the oil body protein may be used.

New oil body proteins may be discovered for example by preparing oil bodies and identifying proteins in these preparations using for example SDS gel electrophoresis. Polyclonal antibodies may be raised against these proteins and used to screen cDNA libraries in order to identify nucleic acid sequences encoding oil body proteins. The methodologies are familiar to the skilled artisan (Huynh et al. (1985) in DNA Cloning Vol. 1. a Practical Approach ed. DM Glover, IRL Press, pp 49-78). New oil body proteins may further be discovered using known nucleic acid sequences encoding oil body proteins (e.g. the Arabidopsis, rapeseed, carrot and corn nucleic acid sequences) to probe for example cDNA and genomic libraries for the presence of nucleic acid sequences encoding oil body proteins.

In the practice of the present invention any protein which is classified as thioredoxin, such as the thioredoxin component of the NADPH thioredoxin system and the thioredoxin present in the ferredoxin/thioredoxin system also known as TRx and TRm may be used.

In the practice of the invention any protein which is capable of reducing thioredoxin may be used, including the NADPH thioredoxin reductase and the ferredoxin-thioredoxin reductase and any other proteins having the capability of reducing thioredoxin. In preferred embodiments the thioredoxin and thioredoxin reductase are plant derived.

The nucleic acid sequences encoding thioredoxin polypeptides from diverse biological sources including *E. coli* (Hoeoeg et al. (1984) Biosci. Rep.: 4 917-923); *Methanococcus jannaschii* and *Archaeoglobus fulgidus* (PCT Patent Application 00/36126); *Arabidopsis thaliana* (Rivera-Madrid (1995) Proc. Natl. Acad. Sci. 92: 5620-5624); wheat (Gautier et al (1998) Eur. J. Biochem. 252(2): 314-324); tobacco (Marty et al. (1991) Plant Mol. Biol. 17: 143-148); barley (PCT Patent Application 00/58352); rice (Ishiwatari et al. (1995) Planta 195: 456-463); soybean (Shi et al. (1996) Plant Mol. Biol. 32: 653-662); rapeseed (Bower et al. Plant Cell 8: 1641-1650) and calf (Terashima et al. (1999) DNA Seq. 10(3): 203-205) are available and may all be used in accordance with the present invention. Nucleic acid sequences encoding thioredoxin reductase proteins from Arabidopsis (Riveira Madrid et al. (1995) Proc. Natl. Acad. Sci. USA 92: 5620-5624), *E. coli* (Russel et al. (1988) J. Biol. Chem. 263: 9015-9019); barley (PCT Patent Application 00/58352 and wheat (Gautier et al., (1998) Eur. J. Biochem. 252: 314-324) are also known and may be used in accordance with the present invention.

Known nucleic acid sequences encoding thioredoxin and thioredoxin reductase proteins may be used to design and construct nucleic acid sequence based probes in order to uncover and identify previously undiscovered nucleic acid sequences encoding thioredoxin or thioredoxin reductase, for example by screening cDNA or genomic libraries. Thus additional nucleic acid sequences may be discovered and used in accordance with the present invention. In embodiments of the invention in which a thioredoxin and a thioredoxin reductase are used the nucleic acid sequence encoding the thioredoxin and thioredoxin reductase may be obtained from separate sources or may be obtained from the same source. In general however it is preferred that the nucleic acid sequence encoding the thioredoxin polypeptide and the nucleic acid sequence encoding the thioredoxin reductase are obtained from the same or a similar biological source. The nucleic acid sequences encoding the thioredoxin or thioredoxin reductase proteins may be altered to improve expression levels for example by optimizing the nucleic acids sequence in accordance with the preferred codon usage for the particular cell type which is selected for expression of the thioredoxin or thioredoxin reductase, or by altering of motifs known to destabilize mRNAs (see for example: PCT Patent Application 97/02352). Comparison of the codon usage of the thioredoxin or thioredoxin reductase with codon usage of the host will enable the identification of codons that may be changed. For example typically plant evolution has tended towards a preference for CG rich nucleotide sequences while bacterial evolution has resulted in bias towards AT rich nucleotide sequences. By modifying the nucleic acid sequences to incorporate nucleic acid sequences preferred by the host cell expression may be optimized. Construction of synthetic genes by altering codon usage is described in for example PCT patent Application 93/07278. The thioredoxin or thioredoxin reductase may be altered using for example targeted mutagenesis, random mutagenesis (Shiraishi et al. (1998) Arch. Biochem. Biophys. 358: 104-115; Galkin et al. (1997) Protein Eng. 10: 687-690; Carugo et al. (1997) Proteins 28: 10-28; Hurley et al. (1996) Biochemistry 35: 5670-5678) (and/or by the addition of organic solvent (Holmberg et al. (1999) Protein Eng. 12: 851-856). In embodiments of the invention in which a thioredoxin and thioredoxin reductase are used, the thioredoxin and thioredoxin reductase may be selected by developing a two-dimensional matrix and determining which combination of first and second redox protein is most effective in electron transport using for example a colorometric reduction assay (Johnson et al (1984) J. of Bact. Vol. 158 3:1061-1069, Luthman et al (1982) Biochemistry Vol 21 26:6628-2233). Combinations of thioredoxin and thioredoxin reductase may be tested by determining the reduction of wheat storage proteins and milk storage protein beta-lactoglobulin in vitro (Del Val et al. (1999) J. Allerg. Clin. Immunol. 103: 690-697).

Preparation of Expression Vectors Comprising Oil Body Targeting Proteins and Thioredoxin or Thioredoxin Reductase In accordance with the present invention, the thioredoxin or thioredoxin reductase and the oil body targeting protein are conveniently produced in a cell. In order to produce the thioredoxin or thioredoxin reductase and the oil body targeting protein, a nucleic acid sequence encoding the thioredoxin or thioredoxin reductase and/or the oil body targeting protein are incorporated in a recombinant expression vector. Accordingly the present invention includes a recombinant expression vector comprising the chimeric nucleic acid sequence of the present invention and suitable for expression of the oil body targeting polypeptide and the thioredoxin or thioredoxin reductase suitable for the selected cell. The term "suitable for expression in the selected cell" means that the recombinant expression vector contains all nucleic acid sequences required to ensure expression in the selected cell.

Accordingly the recombinant expression vectors further contain regulatory nucleic acid sequences selected on the basis of the cell which is used for expression and ensuring initiation and termination of transcription operatively linked to the nucleic acid sequence encoding the thioredoxin or thioredoxin reductase or the oil body targeting protein. Regulatory nucleic acid sequences include promoters, enhancers, silencing elements, ribosome binding sites, Shine-Dalgarno sequences, introns and other expression elements. "Operatively linked" is intended to mean that the nucleic acid sequences comprising the regulatory regions linked to the nucleic acid sequences encoding the thioredoxin or thioredoxin reductase or the oil body targeting protein allow expression in the cell. A typical nucleic acid construct consists in the 5' to 3' direction of a promoter region capable of directing expression, a coding region comprising a fused redox polypeptide or an oil body targeting protein (or both) and a termination region functional in the selected cell.

The selection of regulatory sequences will depend on the organism and the cell type in which the thioredoxin or thioredoxin reductase or the oil body targeting protein is expressed and may influence the expression levels of the polypeptide. Regulatory sequences are art-recognized and selected to direct expression of the oil body targeting protein and the thioredoxin or thioredoxin reductase in the cell.

Promoters that may be used in bacterial cells include the lac promoter (Blackman et al. (1978) Cell: 13: 65-71), the trp promoter (Masuda et al. (1996) Protein Eng: 9: 101-106) and the T7 promoters (Studier et al. (1986) J. Mol. Biol. 189: 113-130). Promoters functional in plant cells that may be used in accordance with the present invention include constitutive promoters such as the 35S CaMV promoter (Rothstein et al. (1987) Gene: 53: 153-161) the actin promoter (McElroy et al. (1990) Plant Cell 2: 163-171) and the ubiquitin promoter (European Patent Application 0 342 926). Other promoters are specific to certain tissues or organs (for example roots, leaves, flowers or seeds) or cell types (for example, leaf epidermal cells, mesophyll cells or root cortex cells) and or to certain stages of plant development. Timing of expression may be controlled by selecting an inducible promoter, for example the PR-a promoter described in U.S. Pat. No. 5,614, 395). Selection of the promoter therefore depends on the desired location and timing of the accumulation of the polypeptide. In a preferred embodiment the thioredoxin or thioredoxin reductase and the oil body targeting protein are expressed in a seed cell and seed specific promoters are preferred. Seed specific promoters that may be used in accordance with the present invention include for example the phaseolin promoter (Sengupta-Gopalan et al. (1985) Proc. Natl. Acad. Sci. USA: 82: 3320-3324), and the Arabidopsis 18 kDa oleosin promoter (van Rooijen et al. (1992) Plant. Mol. Biol. 18: 1177-1179). New promoters useful in various plant cell types are constantly discovered. Numerous examples of plant promoters may be found in Ohamuro et al. (Biochem of Pl. (1989) 15: 1-82).

Genetic elements capable of enhancing expression of the polypeptide may be included in the expression vectors. In plant cells these include for example the untranslated leader sequences from viruses such as the AMV leader sequence (Jobling and Gehrke (1987) Nature: 325: 622-625) and the intron associated with the maize ubiquitin promoter (See: U.S. Pat. No. 5,504,200).

Transcriptional terminators are generally art recognized and besides serving as a signal for transcription termination serve as a protective element serving to extend the mRNA half-life (Guarneros et al. (1982) Proc. Natl. Acad. Sci. USA: 79: 238-242). In nucleic acid sequences for the expression in plant cells, the transcriptional terminator typically is from about 200 nucleotide to about 1000 nucleotides in length. Terminator sequences that may be used in accordance with the present invention include for example the nopaline synthase termination region (Bevan et al. (1983) Nucl. Acid. Res.: 11: 369-385), the phaseolin terminator (Van der Geest et al. (1994) Plant J.: 6: 413-423), the terminator for the octopine synthase gene of *Agrobacterium tumefaciens* or other similarly functioning elements. Transcriptional terminators can be obtained as described by An (1987) Methods in Enzym. 153: 292). The selection of the transcriptional terminator may have an effect on the rate of transcription.

Accordingly the present invention provides an expression vector comprising:

1) a first nucleic acid sequence capable of regulating transcription in said cell operatively linked to;

2) a second nucleic acid sequence encoding a recombinant fusion polypeptide comprising (i) a first nucleic acid sequence encoding a sufficient portion of an oil body protein to provide targeting to said oil body linked in reading frame to (ii) a second nucleic acid sequence encoding a thioredoxin or thioredoxin reductase operatively linked to;

3) a third nucleic acid sequence capable of terminating transcription in said cell.

The recombinant expression vector further may contain a marker gene. Marker genes that may be used in accordance with the present invention include all genes that allow the distinction of transformed cells from non-transformed cells including all selectable and screenable marker genes. A marker may be a resistance marker such as an antibiotic resistance marker against for example kanamycin, ampicillin, G418, bleomycin hygromycin, chloramphenicol which allows selection of a trait by chemical means or a tolerance marker against for example a chemical agent such as the normally phytotoxic sugar mannose (Negrotto et al. (2000) Plant Cell Rep. 19: 798-803). In plant recombinant expression vectors herbicide resistance markers may conveniently be used for example markers conferring resistance against glyphosate (U.S. Pat. Nos. 4,940,935 and 5,188,642) or phosphinothricin (White et al. (1990) Nucl. Acids Res. 18: 1062; Spencer et al. (1990) Theor. Appl. Genet. 79: 625-631). Resistance markers to a herbicide when linked in close proximity to the redox protein or oil body targeting protein may be used to maintain selection pressure on a population of plant cells or plants for those plants that have not lost the protein of interest. Screenable markers that may be employed to identify transformants through visual observation include beta-glucuronidase (GUS) (see U.S. Pat. Nos. 5,268,463 and 5,599,670) and green fluorescent protein (GFP) (Niedz et al. (1995) Plant Cell Rep.: 14: 403).

The recombinant expression vectors further may contain nucleic acid sequences encoding targeting signals ensuring targeting to a cell compartment or organelle.

Targeting signals that may be used in accordance with the present invention include targeting signals capable of directing the protein to the periplasm, the cytoplasm, the golgi apparatus, the apoplast (see for example Sijmons et al. (1990) Bio/Technology 8: 217-221; Rogers (1985) J. Biol. Chem. 260: 3731-3738), the chloroplast (Comai et al. (1988) J. Biol. Chem. 263: 15104-15109), the mitochondrion, the peroxisome (Unger et al. (1989) Plant Mol. Biol. 13: 411-418), the ER, the vacuole (Shinshi et al. (1990) Plant Mol. Biol. 14: 357-368 and the oil body. By the inclusion of the appropriate targeting sequences it is possible to direct the oil body targeting protein or the redox fusion polypeptide to the desired organelle or cell compartment.

The recombinant expression vectors of the present invention may be prepared in accordance with methodologies well known to those of skill in the art of molecular biology (see for example: Sambrook et al. (1990) Molecular Cloning, $2^{nd}$ ed. Cold Spring Harbor Press). The preparation of these constructs may involve techniques such as restriction digestion, ligation, gel electrophoresis, DNA sequencing and PCR. A wide variety of cloning vectors is available to perform the necessary cloning steps resulting in a recombinant expression vector ensuring expression of the polypeptide. Especially suitable for this purpose are vectors with a replication system that is functional in *Escherichia coli* such as pBR322, the PUC series of vectors, the M13mp series of vectors, pBluescript etc. Typically these vectors contain a marker allowing the selection of transformed cells for example by conferring antibiotic resistance. Nucleic acid sequences may be introduced in these vectors and the vectors may be introduced in *E. coli* grown in an appropriate medium. Vectors may be recovered from cells upon harvesting and lysing the cells.

Recombinant expression vectors suitable for the introduction of nucleic acid sequences in plant cells include *Agrobacterium* and *Rhizobium* based vectors such as the Ti and Ri plasmids. *Agrobacterium* based vectors typically carry at least one T-DNA border sequence and include vectors such pBIN 19 (Bevan (1984) Nucl Acids Res. Vol. 12, 22:8711-8721) and other binary vector systems (for example: U.S. Pat. No. 4,940,838).

Production of Cells Comprising Thioredoxin or Thioredoxin Reductase and/or Oil Body Targeting Proteins In accordance with the present invention the recombinant expression vectors are introduced into the cell that is selected and the selected cells are grown to produce thioredoxin or thioredoxin reductase and/or the oil body targeting protein either directly or in a progeny cell.

Methodologies to introduce recombinant expression vectors into a cell also referred to herein as "transformation" are well known to the art and vary depending on the cell type that is selected. General techniques to transfer the recombinant expression vectors into the cell include electroporation; chemically mediated techniques, for example CaCl2 mediated nucleic acid uptake; particle bombardment (biolistics); the use of naturally infective nucleic acid sequences for example virally derived nucleic acid sequences or when plant cells are used *Agrobacterium* or *Rhizobium* derived nucleic acid sequences; PEG mediated nucleic acid uptake, microinjection, and the use of silicone carbide whiskers (Kaeppler et al. (1990) Plant Cell Rep. 9:415-418) all of which may be used in accordance with the present invention.

Introduction of the recombinant expression vector into the cell may result in integration of its whole or partial uptake into host cell genome including the chromosomal DNA or the plastid genome. Alternatively the recombinant expression vector may not be integrated into the genome and replicate independently of the host cell's genomic DNA. Genomic integration of the nucleic acid sequence is generally preferred as it will allow for stable inheritance of the introduced nucleic acid sequences by subsequent generations of cells and the creation of cell, plant or animal lines. Preferred embodiments of the present invention involve the use of plant cells. Preferred plant cells used in accordance with the present invention include cells obtainable from Brazil nut (*Betholletia excelsa*); castor (*Riccinus communes*); coconut (*Cocus nucifera*); coriander (*Coriandrum sativum*); cotton (*Gossypium* spp.); groundnut (*Arachis hypogaea*); jojoba (*Simmondsia chinensis*); linseed/flax (*Linum usitatissimum*); maize (*Zea mays*); mustard (Brassica spp. and *Sinapis alba*); oil palm (*Elaeis guineeis*); olive (*Olea europaea*); rapeseed (*Brassica* spp.); safflower (*Carthamus tinctorius*); soybean (*Glycine max*); squash (*Cucurbita maxima*); barley (*Hordeum vulgare*); wheat (*Traeticum aestivum*) and sunflower (*Helianthus annuus*). Transformation methodologies for dicotelydenous plant species are well known. Generally *Agrobacterium* mediated transformation is preferred because of its high efficiency as well as the general susceptibility by many, if not all dicotelydenous plant species. *Agrobacterium* transformation generally involves the transfer of a binary vector (e.g. pBIN19) comprising the DNA of interest to an appropriate *Agrobacterium* strain (e.g. CIB542) by for example tri-parental mating with an *E. coli* strain carrying the recombinant binary vector and an *E. coli* strain carrying a helper plasmid capable of mobilization of the binary vector to the target *Agrobacterium* strain, or by DNA transformation of the *Agrobacterium* strain (Hofgen et al. Nucl. Acids. Res. (1988) 16: 9877. Other transformation methodologies that may be used to transform dicotelydenous plant species include biolistics (Sanford (1988) Trends in Biotechn. 6: 299-302); electroporation (Fromm et al. (1985) Proc. Natl. Acad. Sci. USA 82: 5824-5828); PEG mediated DNA uptake (Potrykus et al. (1985) Mol. Gen. Genetics 199: 169-177); microinjection (Reich et al. Bio/Techn. (1986) 4: 1001-1004) and silicone carbide whiskers (Kaeppler et al. (1990) Plant Cell Rep. 9: 415-418). The exact transformation methodologies typically vary somewhat depending on the plant species that is used.

In a particularly preferred embodiment the oil bodies are obtained from safflower and the recombinant proteins are expressed in safflower. Safflower transformation has been described by Baker and Dyer (Plant Cell Rep. (1996) 16: 106-110).

Monocotelydenous plant species may now also be transformed using a variety of methodologies including particle bombardment (Christou et al. (1991) Biotechn. 9: 957-962; Weeks et al. Plant Physiol. (1993) 102: 1077-1084; Gordon-Kamm et al. Plant Cell (1990) 2: 603-618) PEG mediated DNA uptake (EP 0 292 435; 0 392 225) or *Agrobacterium*-mediated transformation (Goto-Fumiyuki et al (1999) Nature-Biotech. 17 (3):282-286).

Plastid transformation is described in U.S. Pat. Nos. 5,451, 513; 5,545,817 and 5,545,818; and PCT Patent Applications 95/16783; 98/11235 and 00/39313) Basic chloroplast transformation involves the introduction of cloned plastid DNA flanking a selectable marker together with the nucleic acid sequence of interest into a suitable target tissue using for example biolistics or protoplast transformation. Selectable markers that may be used include for example the bacterial aadA gene (Svab et al. (1993) Proc. Natl. Acad. Sci. USA 90: 913-917). Plastid promoters that may be used include for example the tobacco clpP gene promoter (PCT Patent Application 97/06250).

Following transformation the cells are grown, typically in a selective medium allowing the identification of transformants. Cells will be harvested using methodologies generally known to the art. Upon harvesting of the cells it may be necessary to disrupt the cell's integrity in order to allow the oil bodies to associate with the thioredoxin or thioredoxin reductase. Any methodology, including any physical, chemical or biological method known to disrupt the cells' integrity may be used. In general the methodology that is used will depend on the cell that is selected and the methodology that is selected preferably results in a minimal loss of enzymatic activity of the thioredoxin or thioredoxin reductase. Methodologies to disrupt the cell's integrity are generally known to those of ordinary skill in the art. Where plants are employed they may be regenerated into mature plants using plant tissue culture techniques generally known to the skilled artisan. Seeds may be harvested from mature transformed plants and used to propagate the plant line. Plants may also be crossed and in this manner it is possible in accordance with the present invention to breed lines that vary in genetic background. It is also possible to cross a plant line comprising a thioredoxin with a plant line comprising a thioredoxin reductase and/or with a plant line comprising an oil body targeting protein.

Uses of an Oil Body Emulsion Comprising Thioredoxin and/or Thioredoxin Reductase The present invention further provides an emulsion comprising washed oil bodies and thioredoxin or thioredoxin reductase. The emulsion comprising thioredoxin and/or thioredoxin reductase may be used for a variety of purposes, including for the preparation of a formulation capable of providing protection against oxidative stress; for the preparation of formulation capable of chemically reducing a target, for the formulation of a food product; for the formulation of a personal care product; and for the formulation of a pharmaceutical product. In accordance with the present invention the emulsion formulations may comprise thioredoxin or thioredoxin reductase or the emulsion formulation may comprise thioredoxin and thioredoxin reductase. In preferred embodiments of the invention the emulsion formulations contains thioredoxin while the thioredoxin reductase is optionally present.

Accordingly the invention also provides a formulation containing oil bodies comprising a thioredoxin and/or thioredoxin reductase capable of treating or protecting a target against oxidative stress. The stress of the target is treated or prevented by contacting the target with the formulation. The target may be any substance susceptible to oxidative stress, including any molecule, molecular complex, cell, tissue or organ.

The invention also provides a formulation containing oil bodies comprising thioredoxin and/or a thioredoxin reductase capable of chemically reducing a target. Contacting the target with the formulation reduces the target. The target may be any substance susceptible to reduction, including any molecule or molecular complex. Particularly susceptible targets in this regard are the disulfide bonds present in proteins.

The oil bodies comprising thioredoxin and/or reductase may be used to prepare formulations used to reduce the allergenicity of food or increase the digestibility of food. Preferably, the method of reducing the food allergenicity is practiced by mixing the thioredoxin and/or thioredoxin reductase comprising oil bodies with food or food ingredients selected from a variety of sources including for example wheat flour, wheat dough, milk, cheese, soya, yogurt and ice cream. The thioredoxin and/or thioredoxin reductase comprising oil bodies may also be used to increase the digestibility of milk as well as other disulfide containing proteins (Jiao, J. et al. (1992) J. Agric. Food Chem 40: 2333-2336). Further food applications include the use of the thioredoxin and/or thioredoxin reductase comprising oil bodies as a food additive to enhance dough strength and bread quality properties (Wong et al., (1993) J. Cereal Chem. 70: 113-114; Kobrehel et al. (1994) Gluten Proteins: Association of Cereal Research; Detmold, Germany).

The present invention also provides a pharmaceutical composition comprising oil bodies comprising a thioredoxin and/or thioredoxin reductase in a pharmaceutically active carrier. Pharmaceutical compositions that may be prepared in accordance with the present invention include compositions for the treatment of reperfusion injury (Aota et al. (1996) J. Cardiov. Pharmacol. (1996) 27: 727-732), cataracts (U.S. Pat. No. 4,771,036), chronic obstructive pulmonary disease (MacNee et al. (1999) Am. J. Respir. Crit. Care Med. 160:S58-S65), diabetes (Hotta et al. J. Exp. Med. 188: 1445-1451), envenomation (PCT Patent Application 99/20122; U.S. Pat. No. 5,792,506), bronchiopulmonary disease (MacNee (2000) Chest 117:3035-3175); malignancies (PCT Patent Application 91/04320) and the alleviation of the allergenic potential of airborne, for example pollen-derived, and contact allergens (PCT Patent Application 00/44781).

The present invention further provides a personal care formulation containing oil bodies comprising thioredoxin and/or thioredoxin. Personal care products comprising thioredoxin and/or thioredoxin reductase are disclosed in for example Japanese Patent Applications JP9012471A2, JP103743A2, and JP1129785A2 Personal care formulations that may be prepared in accordance with the present invention include formulations capable of improving the physical appearance of skin exposed to detrimental environmental stimuli resulting in oxidative stress for example oxidative stress caused by UV-generated free-radicals. The oil bodies comprising thioredoxin/thioredoxin reductase may also be used to prepare hair care products (U.S. Pat. No. 4,935,231).

The following non-limiting examples are illustrative of the present invention. The examples are given solely for the purpose of illustrating the invention and are not to be construed as limitations to the present invention. Variations to these examples are possible without departing from the spirit and the scope of the invention.

EXAMPLES

Example 1

Obtaining a washed oil body preparation from oilseed rape, soybean, sunflower, white mustard, peanut, squash, flax, safflower and maize—laboratory scale. Dry mature seeds obtained from *Brassica napus* cv Westar, soybean, sunflower, white mustard, peanut, squash, flax, safflower and maize were homogenized in five volumes of cold grinding buffer (50 mM Tris-HCl, pH 7.5, 0.4 M sucrose and 0.5 M NaCl) using a polytron operating at high speed. The homogenate was centrifuged at 10×g for 30 minutes in order to remove particulate matter and to separate oil bodies from the aqueous phase containing the bulk of the soluble seed protein. The oil body fraction was skimmed from the surface of the supernatant with a metal spatula and added to one volume of grinding buffer. In order to achieve efficient washing in subsequent steps it was found to be necessary to thoroughly redisperse the oil bodies in the grinding buffer. This was accomplished by gently homogenizing the oil bodies in grinding buffer using a polytron at low speed. Using a syringe, the redispersed oil bodies were carefully layered underneath five volumes of cold 50 mM Tris-HCl pH 7.5 and centrifuged as above. Following centrifugation, the oil bodies were removed and the washing procedure was repeated two times. The final washed oil body preparation was resuspended in one volume of cold Tris-HCl pH 7.5, redispersed with the polytron.

The oil body samples were dissolved in SDS sample buffer and then analyzed by SDS gel electrophoresis. The results are shown in FIG. 1.

The material thus obtained was then ready to be employed in various formulations.

Example 2

Obtaining a washed oil body preparation from oilseed rape, sunflower and maize on a large scale. This example describes the recovery of the oil body fraction from canola, sunflower and maize seed on a large scale. The resulting preparation contains intact oil bodies and is comparable in purity with a preparation obtained using laboratory scale procedures.

Grinding of seeds. A total of 10-15 kgs of dry canola seed (*Brassica napus* cv Westar), sunflower (*Helianthus annuus*) or maize (*Zea mays*) was poured through the hopper of a colloid mill (Colloid Mill, MZ-130 (Fryma); capacity: 500 kg/hr), which was equipped with a MZ-120 crosswise toothed rotor/stator grinding set and top loading hopper. Approximately 50-75 l water was supplied through an externally connected hose prior to milling. Operation of the mill was at a gap setting of 1R, chosen to achieve a particle size less than 100 micron at 18° C. and 30° C. Following grinding of the seeds tap water was added to the seed slurry to a final volume of 90 liters.

Removal of solids. The resulting slurry, was pumped into a decantation centrifuge (Hasco 200 2-phase decantation centrifuge maximum operating speed 6,000 rpm) after bringing the centrifuge up to an operating speed of 3,500 rpm. Transfer from the mill to the decantation centrifuge at a flow rate of 360 L/hr was achieved using a 1 inch M2 Wilden air operated double diaphragm pump. In 15-minutes approximately 15 kg of seed was decanted.

Oil body separation. Separation of the oil body fraction was achieved using a Sharples Tubular Bowl Centrifuge model AS-16 (Alpha Laval) equipped with a three phase separating bowl and removable ring dam series; capacity: 150 L/hr; ringdam: 30 mm. Operating speed was at 15,000 rpm (13,200×g). A Watson-Marlow (Model 704) peristaltic pump was used to pump the decanted liquid phase (DL) into the tubular bowl centrifuge after bringing the centrifuge up to operating speed. This results in separation of the decanted liquid phase into a heavy phase (HP) comprising water and soluble seed proteins and a light phase (LP) comprising oil bodies. The oil body fraction which was obtained after one pass through the centrifuge is referred to as an unwashed oil body preparation. The oil body fraction was then passed through the centrifuge three more times. Between each pass through the centrifuge, concentrated oil bodies were mixed with approximately five volumes of fresh water. The entire procedure was carried out at room temperature. The preparations obtained following the second separation are all referred to as the washed oil body preparation. Following three washes much of the contaminating soluble protein was removed and the oil body protein profiles obtained upon SDS gel electrophoresis were similar in appearance to those obtained using laboratory scale procedures.

The large scale oil body preparation may be pasteurized. Pasteurization is achieved by initially thickening the washed oil bodies with centrifugation to a water content of 30 to 60%, preferable between 35 and 50% weight and most preferable between 37 and 40% weight. The thickened oil body solution can then be pasteurized in a constant temperature water bath at approximately 65° C. for 20 minutes. The pasteurization temperature could range between 50 and 90° C. and the time for pasteurization could range between 15 seconds to 35 minutes. If the oil bodies are used in a cosmetic formulation, then before pasteurization, 0.1% Glydant Plus, 0.1% BHA and 0.1% BHT may be added as a preservative and antioxidants respectively.

Example 3

Removal of seed proteins by washing the oil body phase. This example describes the recovery of a washed oil body fraction from canola, maize and sunflower seed. Using different washing conditions, it is shown that the washes result in the removal of significant amounts of seed proteins from the oil body preparation. These proteins include proteins which might be allergenic.

A total of 10-15 kgs of dry canola seed (*Brassica napus* cv Westar), maize (*Zea mays*) or sunflower (*Helianthus annuus*) was poured through the hopper of a colloid mill (Colloid Mill, MZ-130 (Fryma)), which was equipped with a MZ-120 crosswise toothed rotor/stator grinding set and top loading hopper. Approximately 50-75 l water was supplied through an externally connected hose prior to milling. Operation of the mill was at a gap setting of 1R, chosen to achieve a particle size less than 100 micron at 18° C. and 30° C. Following grinding of the seeds, tap water was added to the seed slurry to a final volume of 60-90 liters and a sample of the seed slurry was obtained for SDS gel electrophoresis. The slurry was then pumped into a decantation centrifuge (Hasco 200 2-phase decantation centrifuge maximum operating speed 6,000 rpm) after bringing the centrifuge up to an operating speed of 3,500 rpm. Transfer from the mill to the decantation centrifuge was achieved using a 1 inch M2 Wilden air operated double diaphragm pump. In 15-20 minutes approximately 15 kg of seed was decanted. A sample from the decanted liquid phase was obtained for SDS gel electrophoresis. Separation of the oil body fraction was achieved using a Sharples Tubular Bowl Centrifuge model AS-16 (Alpha Laval) equipped with a three phase separating bowl and removable ring dam series; capacity: 150 L/hr; ringdam: 29 mm. Operating speed was at 15,000 rpm (13,200×g). A Watson-Marlowe (Model 704) peristaltic pump was used to pump the decanted liquid phase into the tubular bowl centrifuge after bringing the centrifuge up to operating speed. The unwashed oil body phase was obtained and mixed with approximately 5 volumes of water. This procedure was repeated a total of three more times. The oil body phase which was obtained following the first spin, is referred to as an unwashed oil body preparation. All other preparations are washed oil body preparations. Samples for analysis by SDS gel electrophoresis were obtained following the first and fourth separations.

Upon completion of the fourth wash a 0.9 ml sample of the oil body preparation was homogenized in 0.1 ml 1 M $Na_2CO_3$ and left at room temperature for 30' with agitation. The washed oil body fraction was then recovered following centrifugation, washed once with water and prepared for SDS gel electrophoresis.

Figure 2:
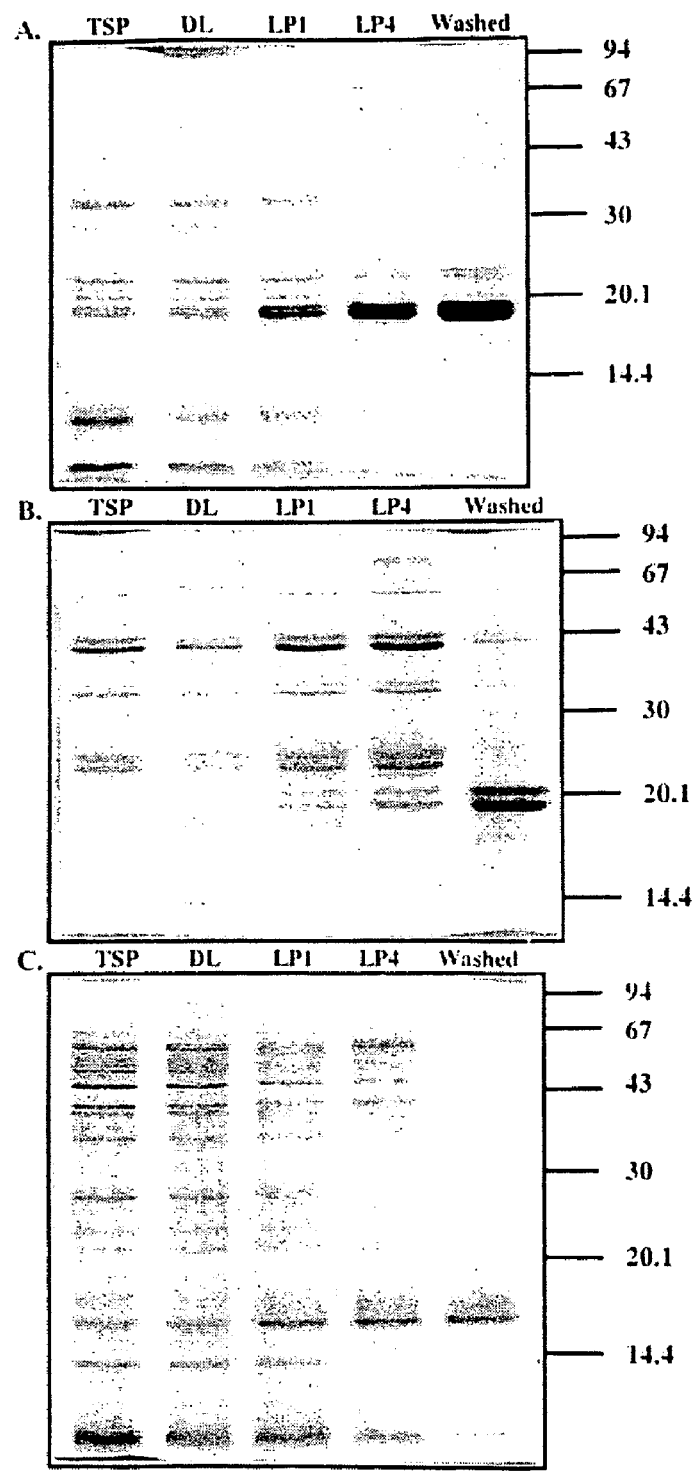
FIG. 2A-C are Coomassie blue stained gels showing the protein profiles of various seed fractions obtained from *Brassica napus* (Canola) (A), sunflower (B), and maize (C). The gels show the following fractions (1) total seed protein (TSP), (2) decanted liquid phase (DL), (3) unwashed oil bodies (LP1), (4) three washes with water (LP4), (5) four washes with water and one wash with 100 mM $Na_2CO_3$ (Washed).

All of the samples were dissolved in SDS sample buffer and the samples were analyzed by SDS gel electrophoresis. The results are shown in FIG. 2.

Example 4

The effect of washing the oil body phase on water retention characteristics. A washed oil body preparation and an unwashed oil body phase were prepared from rapeseed as in example 2. To determine the difference in water retention capacity between the unwashed oil body phase and the washed oil body preparation, 30 mls of oil body preparations were thoroughly mixed using a vortex. The preparations were then incubated for 2 hours in a water bath at 40, 60 or 80° C. and the samples were centrifuged at 1,500×g for 20 minutes (undiluted samples). Another set of samples was prepared by mixing 15 g of washed or unwashed oil body preparation with 15 ml of water. The samples were mixed on a vortex and then incubated at 40, 60 or 80° C. for 2 hours and the amount of water present in the samples was determined following centrifugation at 1,500×g for 20 minutes (diluted samples). Loss of mass attributable to evaporation was measured at 80° C. and 60° C.

At 80° C., the undiluted preparations comprising oil bodies lost significant amounts of water through evaporation. The preparation of unwashed oil bodies lost 26% of their mass, while the washed preparation lost 16%. Upon centrifugation the unwashed preparation released approximately 2.5 ml of aqueous phase, while the washed oil bodies remained in the same phase. Both diluted preparations absorbed water. The volume of oil bodies increased in both cases to 18.5±1 ml.

At 60° C., the undiluted preparations lost approximately 10% of water through evaporation. Following centrifugation, the washed preparation released about 0.5 ml of aqueous phase, while the washed oil body preparation stayed in the same phase. Both diluted preparations absorbed water. At 60° C., the volume of oil bodies increased in both cases to 18±1 ml.

At 40° C., the undiluted samples both released approximately 2 ml of aqueous phase. When the diluted samples were compared, the unwashed preparation absorbed about 3 ml of water, as was the case at 60 or 80° C. However the washed preparation absorbed 8 ml of water at 40° C.

These experiments demonstrate that in a washed oil body preparation heated to 60° C. or 80° C., water remains more tightly associated with the oil body preparation than in an unwashed preparation. When cooled down the washed oil body preparation appeared to be more stable than the unwashed emulsion. When heated to 40° C., the washed oil body preparation was able to absorb a larger volume of exogenously added water without resulting in phase separation offering greater flexibility in preparing oil body based formulations.

Example 5

The effect of washing oil bodies on oil absorption characteristics. A washed oil body preparation and an unwashed oil body phase were prepared from rapeseed as in example 2. To determine the difference in oil absorption capacity between the unwashed oil body phase and the washed oil body preparation, 2 gr of the oil body preparations was dispersed into 12 ml of refined, bleached, deodorized canola oil in a 50 ml tube.

The contents were stirred for 30 seconds every 5 minutes for 30 min. The tubes were then centrifuged at 4,400 rpm for 25 min. The free oil was decanted and the percentage of absorbed oil was determined by weight difference. Three preparations of washed oil bodies were tested and three preparations of unwashed oil bodies were tested.

The oil absorption capacity of unwashed oil bodies was found to vary significantly between the three batches and varied from 18.7% to 28%. Washed oil bodies had reproducible oil absorption of 32±1%. Thus the washed oil body preparation was found to be superior since (1) a larger amount of oil was found to be absorbed and (2) the absorption occurred in a more reproducible manner.

Example 6

Preparation of stabilized oil body emulsions comprising washed safflower oil bodies for use of formulation in a personal care product (Base Formulations A, B, C). A washed oil body preparation was prepared from safflower seeds as described in example 2. The oil bodies were transferred into a mixing pot and 0.7% keltrol was added. The mixture was then vigorously stirred at room temperature. Subsequently 2.0% glycerin was added. The mixture was then heated to 45-50° C. and 0.1% butylated hydroxyanisole (BHA) and 0.1% butylated hydroxytoluene BHT were added. Finally 0.15% Glydant Plus was added. The procedure for Base B and C was slightly different as the temperature was subsequently increased to 60° C. and 2.5% Arlacel 165 was added and mixed until a preparation of homogeneous appearance was obtained. The mixture was then rapidly cooled to 30° C. under moderate stirring.

| Base A Hydrated safflower oil bodies (0.1% 96.95% Glydant Plus, 0.1% BHT, 0.1% BHA) | |
|---|---|
| Glydant Plus | 0.15% |
| BHT | 0.1% |
| BHA | 0.1% |
| Keltrol | 0.7% |
| Glycerine | 2.0% |
| Base B Hydrated safflower oil bodies (0.1% Glydant 95.45% Plus, 0.1% BHT, 0.1% BHA) | |
| Glydant Plus | 0.15% |
| BHT | 0.1% |
| BHA | 0.1% |
| Keltrol | 0.7% |
| Glycerine | 2.0% |
| Arlacel | 2.5% |
| Base C Hydrated safflower oil bodies (0.1% Glydant 94.75% Plus, 0.1% BHT, 0.1% BHA) | |
| Glydant Plus | 0.25% |
| BHT | 0.1% |
| BHA | 0.1% |
| Keltrol | 0.3% |
| Glycerine | 2.0% |
| Arlacel | 2.5% |

The formulations thus prepared were found to be stable with respect to color, odor, viscosity, oxidation, pH and microbial levels for a period of at least 3 months at 45° C. The stability at 45° C. can be extraolated into a stability of approximately 2 years at room temperature. The chemical analysis of the hydrated safflower oil body preparation revealed that the sample contained 50.82% water and 49.18% dry weight. The dry weight (DW) component consisted of 3.76% protein, 93.56% oil and 2.68% other.

Example 7

Preparation of a cosmetically elegant product from base B. Base B was used to formulate a cosmetically elegant product as follows. The water soluble ingredients Keltrol, panthenol and allantoin were dissolved using moderate agitation at room temperature. Once these ingredients were dissolved, glycerin was added while mixing was continued. The water phase was then heated to a final temperature of 75° C. to 77° C. The oil phase was prepared in a separate mixing pot with moderate agitation and subsequently heated to 75° C. to 77° C. The oil phase soluble ingredients that were used were Dimethicone 350, Cetyl Alcohol, Arlacel 165, Finsolv TN, Sesame Oil, Vitamin E Acetate, and Phenonip. The oil phase and water phase were mixed under vigorous agitation for 15 minutes. The resulting emulsion was then gradually cooled to 40° C. and agitation was gradually diminished. At approximately 40° C., Base Formulation B was slowly added to the emulsion. The mixture was then allowed to cool to room temperature.

| | |
|---|---|
| Keltrol | 0.5% |
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Sesame Oil | 1.0% |
| Vitamin E Acetate | 0.05% |
| Phenonip | 1.0% |
| Base Formulation B | 10.0% |
| Water | 77.8% |

Example 8

Preparation of a cosmetically elegant product from Base C. Base C was further formulated and a cosmetically elegant product for topical application was prepared as follows. The water phase soluble ingredients keltrol, panthenol and allantoin were dissolved using moderate agitation at room temperature. When all ingredients were dissolved glycerin was added while mixing was continued. The water phase was then heated to a final temperature of 75° C. to 77° C. The oil phase was prepared in a separate mixing pot using moderate agitation and heated up to 75° C. to 77° C. The oil phase ingredients that were used were Dimethicone 350, Cetyl Alcohol, Arlacel 165, Finsolv TN, Isohexadecane, Vitamin E Acetate, and Phenonip. The two phases were mixed using vigorous agitation with for 15 minutes. The mixture was then gradually cooled to 40° C. The agitation was gradually decreased as the temperature decreased. At approximately 40° C. Base Formulation C was added slowly to the emulsion. The final formulation was then allowed to cool to room temperature.

| | |
|---|---|
| Keltrol | 0.5% |
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Isohexadecane | 2.0% |
| Vitamin E Acetate | 0.05% |
| Phenonip | 1.0% |
| Base Formulation C | 20.0% |
| Water | 66.8% |

Example 9

Preparation of a cosmetically elegant product from Base B. Base B was further was used for formulation in a cosmetically elegant formulation for topical application using the following procedure. The water soluble ingredients keltrol, panthenol and allantoin were dissolved at room temperature under moderate stirring conditions. Glycerin was then added with continued mixing and the water phase was heated to a final temperature of 75° C. to 77° C. The oil phase was prepared in a separate mixing pot with moderate agitation and then subsequently heated up to 75° C. to 77° C. The oil phase ingredients included, SEE 839, Cetyl Alcohol, Arlacel 165, Finsolv TN, Vitamin E Acetate, and Phenonip. The oil phase was then added to the water phase and mixed under vigorous agitation conditions for 15 minutes. The mixture was then gradually cooled to 40° C. At approximately 40° C. Base Formulation B was slowly added to the emulsion. The final formulation was allowed to cool off to room temperature.

| | |
|---|---|
| Keltrol | 0.5% |
| Panthenol | 0.1% |
| Allantoin | 0.05% |
| Glycerin | 2.0% |
| SEE 839 | 1.0% |
| Arlacel 165 | 2.5% |
| Cetyl Alcohol | 2.0% |
| Finsolv TN | 2.0% |
| Vitamin E Acetate | 0.05% |
| Phenonip | 1.0% |
| Base Formulation B | 40.0% |
| Water | 48.8% |

Example 10

Preparation of a sunscreen with a sun protection factor of 8. Bases B was used to prepare a cosmetically elegant sunscreen. The water soluble ingredients keltrol, panthenol and allantoin were dissolved under moderate agitation at room temperature. The glycerin was then added with continued mixing. The water phase was heated to a final temperature of 75° C. to 77° C. The oil phase was prepared in a separate mixing pot under moderate agitation and heated to 75° C. to 77° C. The oil phase ingredients included: Dimethicone, Cetyl Alcohol, Arlacel 165, Finsolv TN, Sesame Oil, Vitamin E Acetate, Parsol MCX and Phenonip. Emulsification involved mixing of the oil phase and the water phase. The two phases were mixed under vigorous agitation conditions for 15 minutes. The mixture was then gradually cooled to 40° C. At approximately 40° C. Base Formulation B was added slowly. The mixture is allowed to cool to room temperature.

| | |
|---|---|
| Keltrol | 0.5% |
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Sesame Oil | 1.0% |
| Vitamin E Acetate | 0.05% |
| Phenonip | 1.0% |
| Base Formulation B | 10.0% |
| Water | 70.3% |
| Parsol MCX | 7.5% |

Example 11

Preparation of a sunscreen. The water soluble ingredients Kaolin and Veegum Ultra were dissolved under moderate agitation at room temperature. The glycerin was then added. The water phase was heated to a final temperature of 75° C. to 77° C. and methylparaben is added. The oil phase was prepared in a separate mixing pot using moderate agitation and heated to 75° C. to 77° C. The oil phase ingredients that were used were Dimethicone 250, Cetyl Alcohol, Arlacel 165, Propylparaben, Safflower Oil, Trivalin SF, Palemol OL and Parsol MCX. The oil an water phases were subsequently mixed under vigorous agitation for 15 minutes. The mixture was then gradually cooled to 40° C., while gradually decreasing agitation. At 40° C., Germall 115 was added and when the temperature reached about 37° C. to 40° C. the safflower oil body preparation was added slowly. The mixture was allowed to cool to room temperature and the colorant (red 33 solution) was added. The final pH was 6.0 and viscosity was 25,000 cps.

| | |
|---|---|
| Purified Water | 47.15% |
| Kaolin USP | 2.50% |
| Veegum Ultra (Mg, Al Sillicate) | 5.00% |
| Glycerin | 2.00% |
| Methylparaben | 0.30% |
| Dimethicone 350 | 0.50% |
| Cetyl Alcohol | 2.00% |
| Arlacel 165 (Glyceryl Stearate & PEG-100 Stearate) | 2.50% |
| Propylparaben | 0.15% |
| Safflower Oil | 2.00% |
| Trivalin SF (Ethyoxydiglycol) | 2.00% |
| Palemol OL (Oleyl Lactate) | 1.00% |
| Parsol MCX (Octyl Methoxycinnamate) | 7.50% |
| Germall 115 (Imidazolidinyl Urea) | 0.30% |
| Hydrated Safflower Oil Body (0.1% Glydant Plus, 0.1% BHT, 0.1% BHA) | 25.00% |
| Red #33 1% | 0.10% |

Example 12

Preparation of a skin care cream containing a stable vitamin A derivative, retinyl palmitate. The water soluble ingredient Keltrol, Panthenol and Allantoin were dissolved under moderate agitation at room temperature. The glycerin was then added while mixing was continued. The water phase was heated to a temperature of 75° C. to 77° C. The oil phase was prepared in a separate mixing pot under moderate agitation and subsequently heated to 75° C. to 77° C. The oil phase ingredients used were Dimethicone 350, Cetyl Alcohol, Arlacel 165, Finsolv TN, Permethyl 101A, Phenonip and Retinyl Palmitate. The two phases were mixed under vigorous agitation for 15 minutes. The mixture was then gradually cooled to 40° C. The agitation was decreased as the temperature decreased. At 40° C. the Base Formulation C was slowly added.

| | |
|---|---|
| Keltrol | 0.5% |
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Permethyl 101A | 2.0% |
| Phenonip | 1.0% |
| Base Formulation C | 50.0% |
| Water | 35.85% |
| Retinyl Palmitate | 1.0% |

Example 13

Preparation of a day cream. The water soluble ingredients Kaolin and the Mg, Al Silicate were dissolved at room temperature. The glycerin is then added while mixing continued. The water phase was heated to a final temperature of 75° C. to 77° C. The oil phase was prepared in a separate mixing pot using moderate agitation and then subsequently heated up to 75° C. to 77° C. The oil phase ingredients that were used were Dimethicone 350, Cetyl Alcohol, Arlacel 165, Trivalin SF, and Palemol OL. The two phases were then mixed using vigorous agitation for 15 minutes. The mixture was then cooled gradually cooled to 40° C. At 40° C. Germaben II was added and when the temperature reached about 37° C. to 40° C. the safflower oil bodies were slowly added. The mixture was then allowed to cool to room temperature. The final pH was adjusted to 6.00 with a final viscosity of 25,060 cps.

| | |
|---|---|
| Purified water | 32.20% |
| Kaolin | 2.50% |
| Veegum Ultra (Mg, Al Silicate) | 5.00% |
| Glycerin | 2.00% |
| Dimethicone 350 | 0.50% |
| Cetyl Alcohol | 2.00% |
| Arlacel 165 (Glyceryl Sterate & PEG-100 Stearate) | 2.50% |
| Trivalin SF (Ethoxydiglycol) | 2.00% |
| Palemol OL (Oleyl Lactate) | 1.00% |
| Germaben II (Diazolidinyl Urea) | 0.30% |
| Hydrated Safflower Oil Body (0.1% Glydant Plus, 0.1% BHT, 0.1% BHA) | 50.00% |

Example 14

Preparation of a night cream. The water soluble ingredients Kaolin, Mg and Al Silicate were dissolved using moderate agitation at room temperature. Glycerin was added while mixing continued. The water phase was heated to a temperature of 75° C. to 77° C. The oil phase was prepared in a separate mixing pot using moderate agitation and heated up to 75° C. to 77° C. The oil phase ingredients used were Dimethicone 350, Cetyl Alcohol, Arlacel 165, Trivalin SF, and Palemol OL. The two phases were mixed under vigorous agitation for 15 minutes. The mixture was then cooled gradually to 60° C. The agitation was gradually decreased as the temperature decreased. At 60° C. glycolic acid was added, at 50° C. a 25% solution of sodium hydroxide was added, at 40° C. the Germall 115 was added and when the temperature reached about 37 to 40° C. the safflower oil bodies were added slowly. The final pH was adjusted to 3.64 with a final viscosity of 35,000 cps.

| | |
|---|---|
| Purified water | 24.20% |
| Kaolin | 2.50% |
| Veegum Ultra (Mg, Al Silicate) | 5.00% |
| Glycerin | 2.00% |
| Dimethicone 350 | 0.50% |
| Cetyl Alcohol | 2.00% |
| Arlacel 165 (Glyceryl Sterate & PEG-100 Stearate) | 2.50% |
| Trivalin SF (Ethoxydiglycol) | 2.00% |
| Palemol OL (Oleyl Lactate) | 1.00% |
| Glycolic Acid | 8.00% |
| Sodium Hydroxide (25% solution) qs pH | 3.3-3.8 |
| Germaben H (Diazolidinyl Urea) | 0.30% |
| Hydrated Safflower Oil Body (0.1% Glydant Plus, 0.1% BHT, 0.1% BHA) | 50.00% |

Example 15

Preparation of a facial mask. The water soluble ingredients Kaolin, Mg, Al Silicate were dissolved using moderate agitation at room temperature. Glycerin was then added under continued mixing. The water phase was heated to a temperature of 75° C. to 77° C. and methylparaben, Green Clay and Bentonite NF BC were added. The oil phase was prepared in a separate mixing pot under moderate agitation and then subsequently heated up to 75° C. to 77° C. The oil phase ingredients used were Dimethicone 350, Trivent OC-G, Arlacel 165, Polyparabin and Safflower Oil. The two phases were mixed under vigorous agitation for 15 minutes. The mixture was then cooled slowly to 40° C. At 40° C. Germall 115 and phytic acid were added. When the temperature reached about 37° C. to 40° C. the safflower oil bodies were added slowly.

| | |
|---|---|
| Distilled Water | 44.25% |
| Kaolin | 2.50% |
| Glycerin | 2.00% |
| Methylparaben | 0.30% |
| Green Clay (Montmorillonate) | 2.00% |
| Bentonite NF BC | 10.00% |
| Dimethicone 350 | 0.50% |
| Trivent OC-G (Tricaprylin) | 2.00% |
| Glyceryl Stearate & PEG-100 Stearate | 2.00% |
| Propylparabin | 0.15% |
| Safflower oil | 1.00% |
| Ethoxydiglycol | 3.00% |
| Germall 115 (Imidazolidinyl Urea) | 0.30% |
| Hydrated Safflower oil body (0.1% Glydant Plus, 0.1% BHT, 0.1% BHA) | 25.00% |
| Phytic Acid | 5.00% |

Example 16

Comparison of Washed Oil Bodies and Lipid Vesicles in the Preparation of Cosmetic Formulations. Washed Oil bodies were prepared as described in example 2, 20 pasteurized and 0.1% BHT, 0.1% BHA and 0.1% Glydant plus added. Lipid vesicles were prepared in accordance with the specification of U.S. Pat. No. 5,683,740 except that they were prepared from safflower seed, pasteurized and 0.1% BHT, 0.1% BHA and 0.1% Glydant Plus was added.

The oil bodies and lipid vesicles were compared with respect to emulsion stability, color changes, odor changes, viscosity, microbial growth and cosmetic desirability parameters. To evaluate stability, the samples were tested at 45° C., 4° C. and room temperature (3 months at 45° C. is equivalent to approximately 2 year shelf life at room temperature). To evaluate emulsion stability, 150 g of each sample was maintained at 45° C., 75 g of each sample was maintained at room temperature or at 4° C. Emulsion stability was evaluated for emulsion separation, oil droplet separation and coalescence. The 4° C. sample was used as the reference for comparison. Color changes were evaluated by visual inspection. Color was evaluated on the accelerated oven sample (45° C.) and the room temperature sample and compared to the 4° C. as a reference. Odor was tested as with the color with the 4° C. sample used as a reference point. In order to maintain consistency, the odor was judged by two individuals who both agreed on the evaluation. Viscosity of each sample was measured at room temperature using a RVT Model viscometer with Spindle E at 10 rpm. Microbial growth was measured on 10 g of each sample. The sample was diluted and 1 ml of the sample is added to 49° C. Tryptic Soy Agar, swirled and allowed to cool. The plates were incubated at 35° C. for 48 hours and a colony count was taken. Finally, cosmetic attributes were evaluated by 3 individuals, 2 individuals who were familiar with oil bodies/lipid vesicles and 1 person who was not. Cosmetic attributes include skin penetration, residue left on the skin after the sample was rubbed in, dryness (lack of moisture) and oiliness.

Table 1 summarizes the results for the oil bodies. The pH for the oil body sample was constant at 6.50 throughout the test at room temperature and at 45° C. The oil body preparation, when applied to the skin, distributed evenly on the skin, was fast penetrating and left almost no residue on the skin surface. The oil body preparation was also stable with respect to color, odor, viscosity and emulsion stability.

Table 2 summarizes the results for the lipid vesicles. The pH for the lipid vesicle sample is difficult to measure because of the total separation but was approximately 6.8. The lipid vesicle preparation, when applied to the skin, was very oily and left a film residue on the skin. The lipid vesicle preparation was stable with respect to microbial growth but was not stable with respect to color, odor and emulsion stability.

The above results demonstrate that the oil washed oil body preparation is clearly superior to lipid vesicles with respect to both physical parameters (color, odor, stability) and cosmetic parameters (penetration, residual residue, and oiliness). These parameters are critical to the preparation of personal care products.

Example 17

Preparation of a mayonnaise-like emulsion comprising a washed oil body preparation. A washed oil body preparation was prepared from rapeseed as in example 2 and a mayonnaise-like emulsion was produced by mixing the following components using a domestic electric blender.

| | |
|---|---|
| Sunflower oil | 78 gr |
| Egg yolk | 8 gr |
| Vinegar | 9 gr |
| Salt | 0.5 gr |
| Washed oil bodies | 5 gr |

A product with a mayonnaise-like texture was obtained. The mayonnaise-like product was stable for at least 1 day at 4° C.

Example 18

Preparation of a cholesterol-free mayonnaise-like emulsion. A washed oil body preparation was prepared from rapeseed as in Example 2 and a mayonnaise-like emulsion was produced by mixing the following ingredients:

| | |
|---|---|
| Sunflower oil | 200 gr |
| Washed oil bodies | 100 gr |
| Vinegar | 30 ml |

A product with a mayonnaise-like texture was obtained. Since the mayonnaise is prepared without egg yolk, an ingredient commonly employed in commercially obtainable mayonnaises, the product prepared using washed oil bodies is free of cholesterol. The mayonnaise was found to be as stable as a commercial mayonnaise when stability was assessed using centrifugation.

Example 19

Preparation of a vinaigrette-like emulsion comprising a washed oil body preparation. A washed oil body preparation was prepared from rapeseed as in example 2 and a vinaigrette-like emulsion was produced by manual mixing of the following components.

| | |
|---|---|
| Sunflower oil | 17.5 gr |
| Mustard | 0.4 gr |
| Vinegar | 0.5 gr |
| Washed oil bodies | 7.7 gr |

A product with a vinaigrette-like texture was obtained. The vinaigrette-like product was stable for at least several days at 4° C.

Example 20

Preparation of a spreadable mustard-like product. A washed oil body preparation was obtained from rapeseed as outlined in example 2. The following ingredients were mixed to obtain a mustard-like product.

| | |
|---|---|
| Mustard | 70 gr |
| Washed oil bodies | 30 gr |

The resulting emulsion formulation is a mustard-like product which may easily be spread and has creamier, less gritty taste characteristics than mustard.

Example 21

Preparation of a bechamel-like sauce. A washed oil body preparation was obtained from rapeseed as outlined in example 2. The washed oil body preparation was heated at moderate heat and an equal part of flour was added and mixed with the heated washed oil body preparation. While stirring manually, milk was gradually added to this mixture.

| | |
|---|---|
| Flour | 50 gr |
| Washed oil bodies | 50 gr |
| Milk | 100 ml-1 l. |

A bechamel-like sauce was obtained. The consistency of the sauce may be as desired depending on the amount of milk which is added. Additional flavorants also may be added as required. The absence of hydrogenated fatty acids in this product gives it an advantage over a sauce prepared from common domestic margarine.

Example 22

Isolation of Thioredoxin and NADPH Thioredoxin Reductase Genes

An Arabidopsis silique cDNA library CD4-12 was obtained from the Arabidopsis Biological Resource Centre (ABRC, http://aims.cps.msu.edu) Arabidopsis stock center and used as a template for the isolation of the thioredoxin h (Trxh) and thioredoxin reductase genes from Arabidopsis. For the isolation of the Trxh gene the following primers were synthesized:

GVR833: 5' TA<u>CCATGG</u>CTTCGGAAGAAGGA 3' (SEQ.ID.NO.21)

The sequence identical to the 5' end of the Trxh gene as published in Rivera-Madrid et al, (1993) Plant Physiol 102: 327-328, is indicated in bold. Underlined is an NcoI restriction site to facilitate cloning.

GVR834: 5' GA<u>AAGCTT</u>AAGCCAAGTGTTTG3' (SEQ.ID.NO.22)

The sequence complementary to the 3' end of the Trxh gene as published in Rivera-Madrid et al, (1993) Plant Physiol 102: 327-328, is indicated in bold. Underlined is an HindIII restriction site to facilitate cloning.

A Polymerase Chain Reaction (PCR) was carried out using GVR833 and GVR834 as primers and the cDNA library CD4-12 as a template. The resulted PCR fragment was isolated, cloned into pBluescript and sequenced. The isolated sequence encoding Trxh was identical to the published Trxh gene sequence (Rivera-Madrid et al, (1993) Plant Physiol 102: 327-328). The pBluescript vector containing the Trxh gene is called pSBS2500

For the isolation of the thioredoxin reductase gene the following primers were synthesized:

GVR836:5' GGCCAGCACACTACCATGAATGGTCTC-GAAACTCAC3'(SEQ.ID.NO.23). The sequence identical to the 5' end of the thioredoxin reductase gene as published (Jacquot et al, J Mol Biol. (1994) 235 (4): 1357-63.), is indicated in bold).

GVR837: 5' TTAAGCTTCAATCACTCTTACCTTGCTG' (SEQ.ID.NO.24)

A Polymerase Chain Reaction (PCR) was carried out using GVR836 and GVR837 as primers and the cDNA library CD4-12 as a template. The resulted PCR fragment was isolated, cloned into pBluescript and sequenced. The pBluescript vector containing the thioredoxin reductase gene is called pSBS2502.

A total of three clones were sequenced, the sequence of each of the three clones were identical to each other. However, as depicted in FIG. 3 this sequence indicated several nucleotide differences compared to the published thioredoxin reductase gene sequence published (Jacquot et al, J Mol Biol. (1994) 235 (4):1357-63.). The complete coding sequence and its deduced aminoacid sequence is shown in FIG. 4. As a result of the nucleotide differences between the published sequence and the sequence isolated in this report, several aminoacid changes are also predicted. A comparison of the deduced aminoacid sequence of the published NADPH thioredoxin reductase sequence (ATTHIREDB, Jacquot et al, J Mol Biol. (1994) 235 (4):1357-63.) with the sequence isolated in this report (TR) is shown in FIG. 5.

Example 23

Construction of Plant Expression Vectors

Expression vectors were constructed to allow for the seed specific over-expression of thioredoxin and NADPH thioredoxin reductase in seeds. Vectors were constructed to allow for over-expression in its natural subcellalar location and for accumulation on oil bodies.

Construction of plant transformation vector pSBS2520. The Arabidopsis thioredoxin h gene as described in example 22 was placed under the regulatory control of the phaseolin promoter and the phaseolin terminator derived from the common bean *Phaseolus vulgaris* (Slightom et al (1983) Proc. Natl Acad Sc USA 80: 1897-1901; Sengupta-Gopalan et al., (1985) PNAS USA 82: 3320-3324)). A gene splicing by overlap extension technique (Horton et al (1989) 15: 61-68) was used to fuse the phaseolin promoter to the Trxh gene. Standard molecular biology laboratory techniques (see eg: Sambrook et al. (1990) Molecular Cloning, $2^{nd}$ ed. Cold Spring Harbor Press) were used to furnish the phaseolin promoter and terminator with PstI and HindIII/KpnI sites respectively (see FIG. 6). Standard molecular biology laboratory techniques were also used to place the phaseolin terminator downstream from the Trxh gene. The PstI-phaseolin promoter-Trxh-phaseolin terminator-KpnI insert sequence was cloned into the PstI-KpnI sites of pSBS3000 (pSBS3000 is a derivative from the *Agrobacterium* binary plasmid pPZP221 (Hajdukiewicz et al., 1994, Plant Molec. Biol. 25: 989-994). In pSBS3000, the CaMV35S promoter-gentamycin resistance gene-CAMV 35S terminator of pPZP221 was replaced with parsley ubiquitin promoter-phosphinothricin acetyl transferase gene-parsley ubiquitin termination sequence to confer resistance to the herbicide glufosinate ammonium.) The resulting plasmid is called pSBS2520. The sequence of the phaseolin promoter-Arabidopsis Trxh-phaseolin terminator sequence is shown in FIG. 6.

Construction of plant transformation vector pSBS2510. The 3' coding sequence of an Arabidopsis oleosin gene (Van Rooijen et al (1992) Plant Mol. Biol. 18: 1177-1179). was altered to contain an NcoI site. The NcoI-HindIII fragment from vector pSBS2500 (Example 22) containing the Trxh was ligated to the coding sequence of this Arabidopsis oleosin utilizing this NcoI restriction site. A gene splicing by overlap extension technique (Horton et al (1989) 15: 61-68) was used to fuse the phaseolin promoter (Slightom et al (1983) Proc. Natl Acad Sc USA 80: 1897-1901; Sengupta-Gopalan et al., (1985) PNAS USA 82: 3320-3324) containing a synthetic PstI site (see construction of pSBS2520)) to the coding sequence of the Arabidopsis oleosin. Standard molecular biology laboratory techniques (see eg: Sambrook et al. (1990) Molecular Cloning, $2^{nd}$ ed. Cold Spring Harbor Press) were again used to clone the HindIII KpnI fragment containing the phaseolin terminator (see construction of pSBS2520) dowstream of the Trxh gene. The PstI-phaseolin promoter-oleosin-Trxh-phaseolin terminator-KpnI insert sequence was cloned into the PstI-KpnI sites of pSBS3000. The resulting plasmid is called pSBS2510. The sequence of the phaseolin promoter-oleosin Trxh-phaseolin terminator sequence is shown in FIG. 7.

Construction of plant transformation vector pSBS2521. This vector contains the same genetic elements as the insert of pSBS2510 except the Trxh gene is fused to the 5' end of the oleosin gene. The 3' oleosin coding sequence including its native stopcodon (Van Rooijen et al (1992) Plant Mol. Biol. 18: 1177-1179) was furnished with a HindIII cloning site. Again a gene splicing by overlap extension technique (Horton et al (1989) 15: 61-68) was used to fuse the phaseolin promoter to the Trxh gene and to fuse the Trxh gene to the oleosin sequence. Standard molecular biology laboratory techniques (see eg: Sambrook et al. (1990) Molecular Cloning, $2^{nd}$ ed. Cold Spring Harbor Press) were again used to clone the HindIII KpnI fragment containing the phaseolin terminator (see construction of pSBS2520) dowstream of the oleosin gene. The PstI-phaseolin promoter-Trxh oleosin-phaseolin terminator-KpnI insert sequence was cloned into the PstI-KpnI sites of pSBS3000. The resulting plasmid is called pSBS2521. The sequence of the phaseolin promoter-Trxh oleosin-phaseolin terminator sequence is shown in FIG. 8.

Construction of plant transformation vector pSBS2527. The Arabidopsis NADPH thioredoxin reductase gene as described in example 22 was placed under the regulatory control of the phaseolin promoter and the phaseolin terminator derived from the common bean *Phaseolus vulgaris* (Slightom et al (1983) Proc. Natl Acad Sc USA 80: 1897-1901; Sengupta-Gopalan et al., (1985) PNAS USA 82: 3320-3324). A gene splicing by overlap extension technique (Horton et al (1989) 15: 61-68) was used to fuse the phaseolin promoter to the thioredoxin reductase gene. Standard molecular biology laboratory techniques (see eg: Sambrook et al. (1990) Molecular Cloning, $2^{nd}$ ed. Cold Spring Harbor Press) were used to furnish the phaseolin promoter and terminator with PstI and HindIII/KpnI sites respectively (see FIG. 6). Standard molecular biology laboratory techniques were also used to place the phaseolin terminator dowstream from the thioredoxin reductase gene. The PstI-phaseolin promoter-thioredoxin reductase-phaseolin terminator-KpnI insert sequence was cloned into the PstI-KpnI sites of pSBS3000 The resulting plasmid is called pSBS2527. The sequence of the phaseolin promoter-Arabidopsis thioredoxin reductase-phaseolin terminator sequence is shown in FIG. 9.

Construction of plant transformation vector pSBS2531. A gene splicing by overlap extension technique (Horton et al (1989) 15: 61-68) was used to fuse the phaseolin promoter (Slightom et al (1983) Proc. Natl Acad Sc USA 80: 1897-1901; Sengupta-Gopalan et al., (1985) PNAS USA 82: 3320-3324) to the coding sequence of the Arabidopsis oleosin. The same gene splicing technique was used to fuse the oleosin gene to the thioredoxin reductase coding sequence. Standard molecular biology laboratory techniques (see eg: Sambrook et al. (1990) Molecular Cloning, $2^{nd}$ ed. Cold Spring Harbor Press) were again used to clone the HindIII KpnI fragment containing the phaseolin dowstream of the thioredoxin reductase gene. The PstI-phaseolin promoter-oleosin-thioredoxin reductase-phaseolin terminator-KpnI insert sequence was cloned into the PstI-KpnI sites of pSBS3000. The resulting plasmid is called pSBS2531. The sequence of the phaseolin promoter-oleosin thioredoxin reductase-phaseolin terminator sequence is shown in FIG. 10.

Construction of plant transformation vector pSBS2529 This vector contains the same genetic elements as the insert of pSBS2531 except the thioredoxin reductase gene is fused to the 5' end of the oleosin gene. The 3' oleosin coding sequence including its native stopcodon (Van Rooijen et al. (1992) Plant Mol. Biol. 18: 1177-1179) was furnished with a HindIII cloning site. Again a gene splicing by overlap extension technique (Horton et al (1989) 15: 61-68) was used to fuse the phaseolin promoter to the thioredoxin reductase gene and to fuse the thioredoxin reductase gene to the oleosin sequence. Standard molecular biology laboratory techniques (see eg: Sambrook et al. (1990) Molecular Cloning, $2^{nd}$ ed. Cold Spring Harbor Press) were again used to clone the HindIII KpnI fragment containing the phaseolin terminator (see construction of pSBS2520) dowstream of the oleosin gene. The PstI-phaseolin promoter-thioredoxin reductase oleosin-phaseolin terminator-KpnI insert sequence was cloned into the PstI-KpnI sites of pSBS3000. The resulting plasmid is called pSBS2529. The sequence of the phaseolin promoter-thioredoxin reductase oleosin-phaseolin terminator sequence is shown in FIG. 11.

Plasmids pSBS2510, pSBS2520, pSBS2521, pSBS2527, pSBS2529 and pSBS2531 and were electroporated into *Agrobacterium* strain EHA101. These *Agrobacterium* strains were used to transform Arabidopsis. Arabidopsis transformation was done essentially as described in "Arabidopsis Protocols; Methods in molecular biology Vol 82. Edited by Martinez-Zapater J M and Salinas J. ISBN 0-89603-391-0 pg 259-266 (1998) except the putative transgenic plants were selected on agarose plates containing 80 µM L-phosphinothricine, after they were transplanted to soil and allowed to set seed.

Example 24

Polyacrylamide Gelelectrophoresis and Immunoblotting of Transgenic Seed Extracts Source of Arabidopsis thioredoxin, thioredoxin reductase and oleosin antibodies. The Arabidopsis thioredoxin and thioredoxin reductase genes were cloned in frame in bacterial expression vector pRSETB (Invtrogen) to allow for the overexpression of Arabidopsis thioredoxin and thioredoxin reductase proteins. These proteins were purified using standard protocols (see eg Invitrogen protocol) and used to raise antibodies in rabbits using standard biochemical techniques (See eg Current Protocols in Molecular Biology, John Wiley & Sons, N.Y. (1989). The Arabidopsis oleosin gene was cloned in frame in bacterial expression vector pRSETB (Invitrogen) to allow for the overexpression Arabidopsis oleosin protein. This protein was purified using standard protocols (see eg Invitrogen protocol) and used to prepare mouse monoclonal antibodies using standard biochemical techniques (See eg Current Protocols in Molecular Biology, John Wiley & Sons, N.Y. (1989).

Preparation of total Arabidopsis seed extracts for PAGE. Arabidopsis seeds were ground in approximately 20 volumes of 2% SDS, 50 mM Tris-Cl, this extract was boiled, spun and the supernatant was prepared for polyacrylamide gelelectrophoresis (PAGE) using standard protocols.

Preparation of Arabidopsis oil body protein extracts. Arabidopsis seeds were ground in approximately 20 volumes of water and spun in a microfuge. The oil bodies were recovered and washed sequentially with approximately 20 volumes of water, a high stringency wash buffer, containing 8M urea and 100 mM sodiumcarbonate and water. After this last wash the oil bodies are prepared for poly acrylamide gelelectrophoresis (PAGE) using standard protocols.

Figure 12:
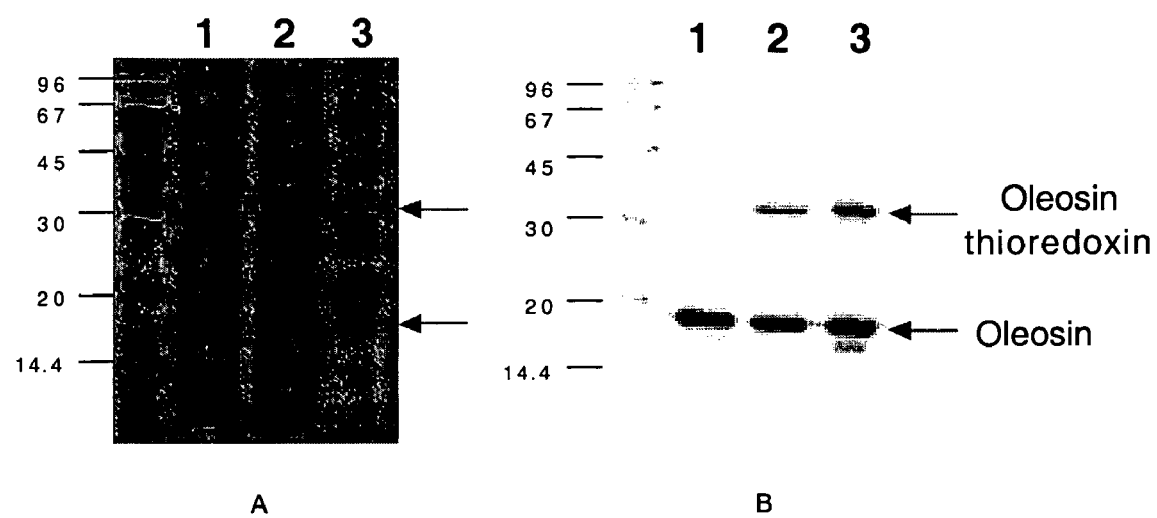

Analysis of seed and oil body extracts from plants transformed with pSBS2510 Total seed and oil body protein extracts from plants transformed with pSBS2510 were loaded onto polyacrylamide gels and either stained with coomassie brilliant blue or electroblotted onto PVDF membranes. The membranes were challenged with a polyclonal antibody raised against Arabidopsis thioredoxin, or a monoclonal antibody raised against the Arabidopsis 18.5 kDa oleosin and visualized using alkaline phosphatase. Expression of the oleosin-thioredoxin results in an additional band of 31.2 kDa. The results are shown in FIG. 12. The thioredoxin antibodies are immunologically reactive with a band of the right predicted molecular weight (31.2 kDa), the oleosin antibodies are also immunologically reactive with a band of the right predicted molecular weight for the fusion protein (31.2 kDa) in addition to a band corresponding to the native Arabidopsis oleosin (18.5 kDa). This indicates that oleosin-thioredoxin is expressed in Arabidopsis seeds and is correctly targeted to oil bodies.

Figure 13:
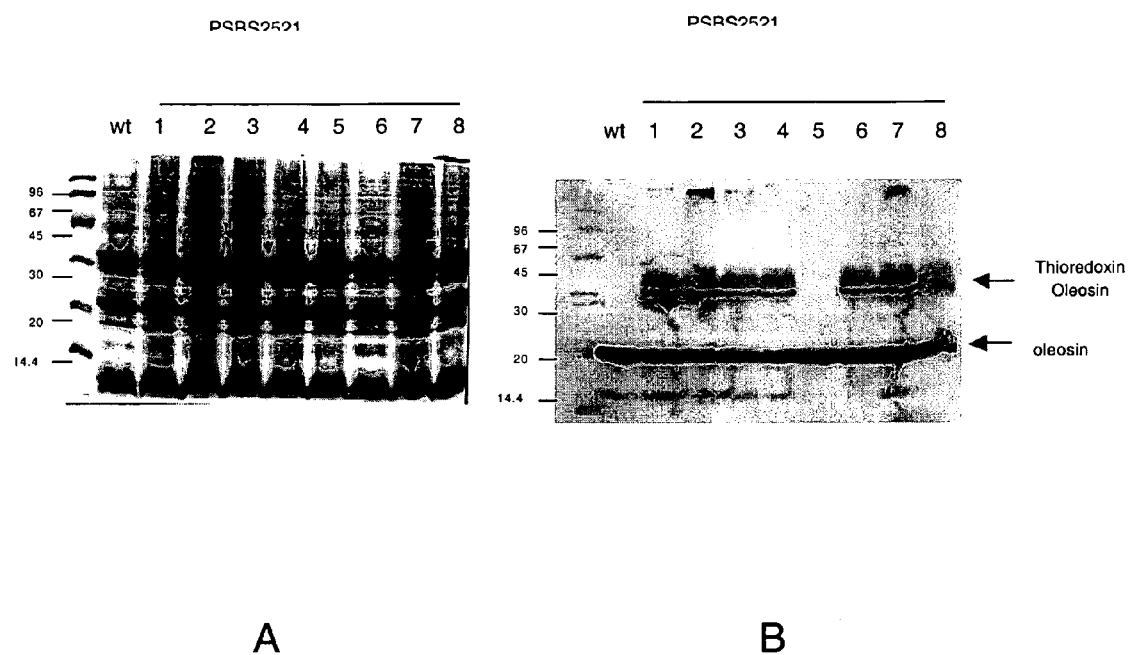

Analysis of seed and oil body extracts from plants transformed with pSBS2521 Total seed and oil body protein extracts from plants transformed with pSBS25121 were loaded onto polyacrylamide gels and either stained with coomassie brilliant blue or electroblotted onto PVDF membranes. The membranes were challenged with a polyclonal antibody raised against Arabidopsis thioredoxin, or a monoclonal antibody raised against the Arabidopsis 18.5 kDa oleosin and visualized using alkaline phosphatase. Expression of the thioredoxin-oleosin results in an additional band of 31.2 kDa. The results are shown in FIG. 13. The thioredoxin antibodies are immunologically reactive with a band of the right predicted molecular weight (31.2 kDa), the oleosin antibodies are also immunologically reactive with a band of the right predicted molecular weight for the fusion protein (31.2 kDa) in addition to a band corresponding to the native Arabidopsis oleosin (18.5 kDa). This indicates that thioredoxin-oleosin is expressed in Arabidopsis seeds and is correctly targeted to oil bodies.

Figure 14:
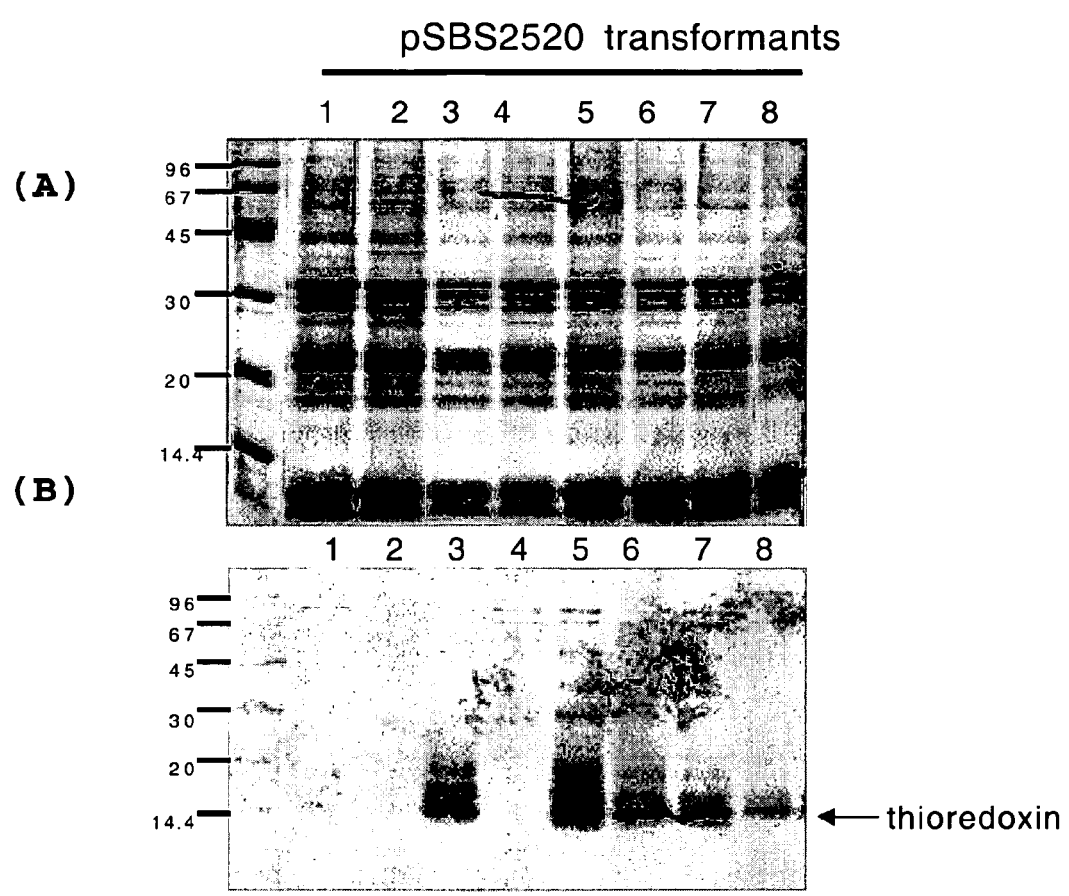

Analysis of seed extracts from plants transformed with pSBS2520 Total seed extracts from plants transformed with pSBS2520 were loaded onto polyacrylamide gels and either stained with coomassie brilliant blue or electroblotted onto PVDF membranes. The membranes were challenged with a polyclonal antibody raised against Arabidosis thioredoxin and visualized using alkaline phosphatase. The thioredoxin antibodies are immunologically reactive with a band of approximately the right predicted molecular weight (12 kDa). Untransformed seeds do not show a detectable thioredoxin band (results not shown). The results of this analysis are shown in FIG. 14.

Analysis of seed and oil body extracts from plants transformed with pSBS2529 Total seed and oil body protein extracts from plants transformed with pSBS2529 were loaded onto polyacrylamide gels and electroblotted onto PVDF membranes. The membranes were challenged with a polyclonal antibody raised against Arabidopsis thioredoxin reductase, or a monoclonal antibody raised against the Arabidopsis 18.5 kDa oleosin and visualized using alkaline phosphatase.

Figure 15:
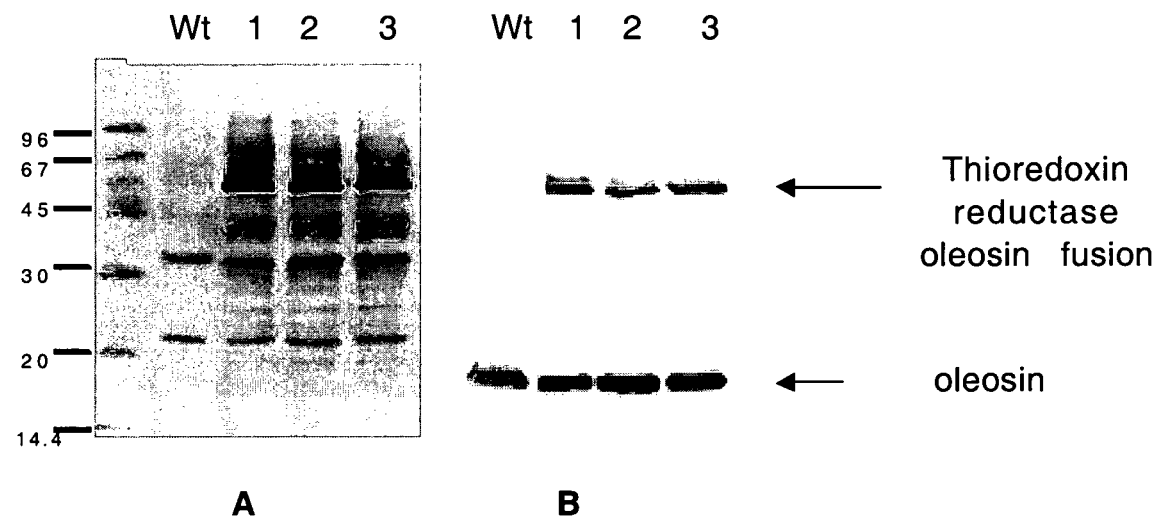

Expression of the thioredoxin reductase-oleosin results in an additional band of 53.8 kDa. The results are shown in FIG. 15. The thioredoxin reductase antibodies are immunologically reactive with a band of the right predicted molecular weight for the fusion protein (53.8 kDa), the oleosin antibodies are also immunologically reactive with a band of the right predicted molecular weight (53.8 kDa) in addition to a band corresponding to the native Arabidopsis oleosin (18.5 kDa). This indicates that thioredoxin reductase-oleosin is expressed in Arabidopsis seeds.

Analysis of seed extracts from plants transformed with pSBS2527 Total seed extracts from plants transformed with pSBS2527 were loaded onto polyacrylamide gels and electroblotted onto PVDF membranes. The membranes were challenged with a polyclonal antibody raised against Arabidopsis thioredoxin reductase and visualized using alkaline phosphatase. The thioredoxin reductase antibodies are immunologically reactive with a band of approximately the right predicted molecular weight for the (35.3 kDa). Untransformed seeds do not show a detectable thioredoxin band. The results of this analysis are shown in FIG. 16.

Figure 17:
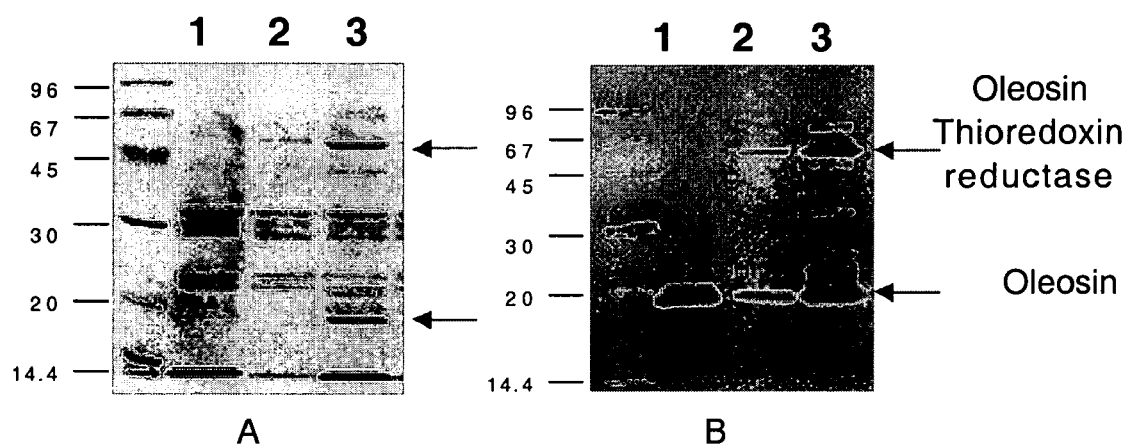

Analysis of seed extracts from plants transformed with pSBS2531. FIG. 17 shows a protein gel and immunoblot of the expression of oleosin-DMSR in Arabidopsis T2 seeds and correct targeting to Arabidopsis oil bodies. The expected molecular weight based on the deduced amino acid sequence is calculated to be 53,817 Da. In the oil body extract of the putative transgenic oleosin-thioredoxin reductase sample an extra band of approximately 54 kDa can be seen (Panel A). This band is confirmed to be oleosin-thioredoxin reductase by immunoblotting (Panel B). From the polyacrylamide gel it can be seen that the expression of the oleosin-Thioredoxin reductase is about double compared to the expression of the major 18.5 kDa Arabidopsis oleosin. This represents approximately 2-4% of total seed protein.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Time (days) | Color | Odor | Stability | Viscosity (cps) | Microbial Growth |
|---|---|---|---|---|---|
| Room Temperature | | | | | |
| 0 | Pale yellow | Very Mild | No separation | 3500 +/− 100 | 500 |
| 14 | Pale yellow | No change | No separation | 3500 +/− 100 | 300 |
| 25 | Pale yellow | No change | No separation | 3500 +/− 100 | <10 |
| 45° C. | | | | | |
| 0 | Pale yellow | Very Mild | No separation | 3500 +/− 100 | 500 |
| 14 | Pale yellow | Mild | No separation | 4000 +/− 100 | <20 |
| 25 | Mildly yellow | Mild | No separation | 4000 +/− 100 | <10 |
| 4° C. | | | | | |
| 0 | Pale yellow | Very Mild | No separation | 3500 +/− 100 | 500 |
| 14 | Pale yellow | Very Mild | No separation | 3500 +/− 100 | 250 |
| 25 | Pale yellow | Very Mild | No separation | 3500 +/− 100 | <10 |

TABLE 2

| Time (days) | Color | Odor | Stability | Viscosity (cps) | Microbial Growth |
|---|---|---|---|---|---|
| Room Temperature | | | | | |
| 0 | Dark yellow | Very Mild | Separation | Approx. 4000 | <20 |
| 14 | Dark yellow | Very Mild | Total Separation | Sluggish | <20 |
| 25 | Darker yellow | Very Mild | Total Separation | Sluggish | <10 |
| 45° C. | | | | | |
| 0 | Dark yellow | Neutral | No separation | 3500 +/− 100 | <20 |
| 14 | Brown | Amine Odor | No separation | 4000 +/− 100 | <10 |
| 25 | Dark brown | Fishy | No separation | 4000 +/− 100 | <10 |
| 4° C. | | | | | |
| 0 | Dark yellow | Neutral | Separation | Approx. 4000 | <20 |
| 14 | Dark yellow | Neutral | No separation | 3500 +/− 100 | <10 |
| 25 | Dark yellow | Neutral | No separation | 3500 +/− 100 | <10 |

SEQUENCE LISTING

<160> NUMBER OF SEQ ID NOS: 24

<210> SEQ ID NO 1
<211> LENGTH: 1002
<212> TYPE: DNA
<213> ORGANISM: Unknown Organism
<220> FEATURE:
<221> NAME/KEY: CDS
<222> LOCATION: (1)..(999)
<223> OTHER INFORMATION: Description of Unknown Organism: Published
      NADPH thioredoxin reductase

<400> SEQUENCE: 1

```
atg aat ggt ctc gaa act cac aac aca agg ctc tgt atc gta gga agt      48
Met Asn Gly Leu Glu Thr His Asn Thr Arg Leu Cys Ile Val Gly Ser
1               5                   10                  15 ggc cca gcg gca cac acg gcg gcg att tac gca gct agg gct gaa ctt      96
Gly Pro Ala Ala His Thr Ala Ala Ile Tyr Ala Ala Arg Ala Glu Leu
            20                  25                  30 aaa cct ctt ctc ttc gaa gga tgg atg gct aac gac atc gct ccc ggt     144
Lys Pro Leu Leu Phe Glu Gly Trp Met Ala Asn Asp Ile Ala Pro Gly
        35                  40                  45 ggt caa cta aca acc acc acc gac gtc gag aat ttc ccc gga ttt cca     192
Gly Gln Leu Thr Thr Thr Thr Asp Val Glu Asn Phe Pro Gly Phe Pro
    50                  55                  60 gaa ggt att ctc gga gta gag ctc act gac aaa ttc cgt aaa caa tcg     240
Glu Gly Ile Leu Gly Val Glu Leu Thr Asp Lys Phe Arg Lys Gln Ser
65                  70                  75                  80 gag cga ttc ggt act acg ata ttt aca gag acg gtg acg aaa gtc gat     288
Glu Arg Phe Gly Thr Thr Ile Phe Thr Glu Thr Val Thr Lys Val Asp
                85                  90                  95 ttc tct tcg aaa ccg ttt aag cta ttc aca gat tca aaa gcc att ctc     336
Phe Ser Ser Lys Pro Phe Lys Leu Phe Thr Asp Ser Lys Ala Ile Leu
            100                 105                 110 gct gac gct gtg att ctc gct act gga gct gtg gct aag cgg ctt agc     384
Ala Asp Ala Val Ile Leu Ala Thr Gly Ala Val Ala Lys Arg Leu Ser
        115                 120                 125 ttc gtt gga tct ggt gaa ggt tct gga ggt ttc tgg aac cgt gga atc     432
Phe Val Gly Ser Gly Glu Gly Ser Gly Gly Phe Trp Asn Arg Gly Ile
    130                 135                 140 tcc gct tgt gct gtt tgc gac gga gct gct ccg ata ttc cgt aac aaa     480
Ser Ala Cys Ala Val Cys Asp Gly Ala Ala Pro Ile Phe Arg Asn Lys
145                 150                 155                 160 cct ctt gcg gtg atc ggt gga ggc gat tca gca atg gaa gaa gca aac     528
Pro Leu Ala Val Ile Gly Gly Gly Asp Ser Ala Met Glu Glu Ala Asn
                165                 170                 175 ttt ctt aca aaa tat gga tct aaa gtg tat ata atc cat agg aga gat     576
Phe Leu Thr Lys Tyr Gly Ser Lys Val Tyr Ile Ile His Arg Arg Asp
            180                 185                 190 gct ttt aga gcg tct aag att atg cag cag cga gct ttg tct aat cct     624
Ala Phe Arg Ala Ser Lys Ile Met Gln Gln Arg Ala Leu Ser Asn Pro
        195                 200                 205 aag att gat gtg att tgg aac tcg tct gtt gtg gaa gct tat gga gat     672
Lys Ile Asp Val Ile Trp Asn Ser Ser Val Val Glu Ala Tyr Gly Asp
    210                 215                 220 gga gaa aga gat gtg ctt gga gga ttg aaa gtg aag aat gtg gtt acc     720
Gly Glu Arg Asp Val Leu Gly Gly Leu Lys Val Lys Asn Val Val Thr
225                 230                 235                 240 gga gat gtt tct gat tta aaa gtt tct gga ttg ttc ttt gct att ggt     768
Gly Asp Val Ser Asp Leu Lys Val Ser Gly Leu Phe Phe Ala Ile Gly
```

```
cat gag cca gct acc aag ttt ttg gat ggt ggt gtt gag tta gat tcg      816
His Glu Pro Ala Thr Lys Phe Leu Asp Gly Gly Val Glu Leu Asp Ser
            260                 265                 270 gat ggt tat gtt gtc acg aag cct ggt act aca cag act agc gtt ccc      864
Asp Gly Tyr Val Val Thr Lys Pro Gly Thr Thr Gln Thr Ser Val Pro
        275                 280                 285 gga gtt ttc gct gcg ggt gat gtt cag gat aag aag tat agg caa gcc      912
Gly Val Phe Ala Ala Gly Asp Val Gln Asp Lys Lys Tyr Arg Gln Ala
    290                 295                 300 atc act gct gca gga act ggg tgc atg gca gct ttg gat gca gag cat      960
Ile Thr Ala Ala Gly Thr Gly Cys Met Ala Ala Leu Asp Ala Glu His
305                 310                 315                 320 tac tta caa gag att gga tct cag caa ggt aag agt gat tga             1002
Tyr Leu Gln Glu Ile Gly Ser Gln Gln Gly Lys Ser Asp
                325                 330

<210> SEQ ID NO 2
<211> LENGTH: 1002
<212> TYPE: DNA
<213> ORGANISM: Arabidopsis sp.
<220> FEATURE:
<221> NAME/KEY: CDS
<222> LOCATION: (1)..(999)

<400> SEQUENCE: 2 atg aat ggt ctc gaa act cac aac aca agg ctc tgt atc gta gga agt       48
Met Asn Gly Leu Glu Thr His Asn Thr Arg Leu Cys Ile Val Gly Ser
1               5                  10                  15 ggc cca gcg gca cac acg gcg gcg att tac gca gct agg gct gaa ctt       96
Gly Pro Ala Ala His Thr Ala Ala Ile Tyr Ala Ala Arg Ala Glu Leu
            20                  25                  30 aaa cct ctt ctc ttc gaa gga tgg atg gct aac gac atc gct ccc ggt      144
Lys Pro Leu Leu Phe Glu Gly Trp Met Ala Asn Asp Ile Ala Pro Gly
        35                  40                  45 ggt caa cta aca acc acc acc gac gtc gag aat ttc ccc gga ttt cca      192
Gly Gln Leu Thr Thr Thr Thr Asp Val Glu Asn Phe Pro Gly Phe Pro
    50                  55                  60 gaa ggt att ctc gga gta gag ctc act gac aaa ttc cgt aaa caa tcg      240
Glu Gly Ile Leu Gly Val Glu Leu Thr Asp Lys Phe Arg Lys Gln Ser
65                  70                  75                  80 gag cga ttc ggt act acg ata ttt aca gag acg gtg acg aaa gtc gat      288
Glu Arg Phe Gly Thr Thr Ile Phe Thr Glu Thr Val Thr Lys Val Asp
                85                  90                  95 ttc tct tcg aaa ccg ttt aag cta ttc aca gat tca aaa gcc att ctc      336
Phe Ser Ser Lys Pro Phe Lys Leu Phe Thr Asp Ser Lys Ala Ile Leu
            100                 105                 110 gct gac gct gtg att ctc gct act gga gct gtg gct aag cgg ctt agc      384
Ala Asp Ala Val Ile Leu Ala Thr Gly Ala Val Ala Lys Arg Leu Ser
        115                 120                 125 ttc gtt gga tct ggt gaa ggt tct gga ggt ttc tgg aac cgt gga atc      432
Phe Val Gly Ser Gly Glu Gly Ser Gly Gly Phe Trp Asn Arg Gly Ile
    130                 135                 140 tcc gct tgt gct gtt tgc gac gga gct gct ccg ata ttc cgt aac aaa      480
Ser Ala Cys Ala Val Cys Asp Gly Ala Ala Pro Ile Phe Arg Asn Lys
145                 150                 155                 160 cct ctt gcg gtg atc ggt gga ggc gat tca gca atg gaa gaa gca aac      528
Pro Leu Ala Val Ile Gly Gly Gly Asp Ser Ala Met Glu Glu Ala Asn
                165                 170                 175 ttt ctt aca aaa tat gga tct aaa gtg tat ata atc cat agg aga gat      576
Phe Leu Thr Lys Tyr Gly Ser Lys Val Tyr Ile Ile His Arg Arg Asp
```

```
                 180                 185                 190
gct ttt aga gcg tct aag att atg cag cag cga gct ttg tct aat cct      624
Ala Phe Arg Ala Ser Lys Ile Met Gln Gln Arg Ala Leu Ser Asn Pro
        195                 200                 205 aag att gat gtg att tgg aac tcg tct gtt gtg gaa gct tat gga gat      672
Lys Ile Asp Val Ile Trp Asn Ser Ser Val Val Glu Ala Tyr Gly Asp
    210                 215                 220 gga gaa aga gat gtg ctt gga gga ttg aaa gtg aag aat gtg gtt acc      720
Gly Glu Arg Asp Val Leu Gly Gly Leu Lys Val Lys Asn Val Val Thr
225                 230                 235                 240 gga gat gtt tct gat tta aaa gtt tct gga ttg ttc ttt gct att ggt      768
Gly Asp Val Ser Asp Leu Lys Val Ser Gly Leu Phe Phe Ala Ile Gly
                245                 250                 255 cat gag cca gct acc aag ttt ttg gat ggt ggt gtt gag tta gat tcg      816
His Glu Pro Ala Thr Lys Phe Leu Asp Gly Gly Val Glu Leu Asp Ser
            260                 265                 270 gat ggt tat gtt gtc acg aag cct ggt act aca cag act agc gtt ccc      864
Asp Gly Tyr Val Val Thr Lys Pro Gly Thr Thr Gln Thr Ser Val Pro
        275                 280                 285 gga gtt ttc gct gcg ggt gat gtt cag gat aag aag tat agg caa gcc      912
Gly Val Phe Ala Ala Gly Asp Val Gln Asp Lys Lys Tyr Arg Gln Ala
    290                 295                 300 atc act gct gca gga act ggg tgc atg gca gct ttg gat gca gag cat      960
Ile Thr Ala Ala Gly Thr Gly Cys Met Ala Ala Leu Asp Ala Glu His
305                 310                 315                 320 tac tta caa gag att gga tct cag caa ggt aag agt gat tga             1002
Tyr Leu Gln Glu Ile Gly Ser Gln Gln Gly Lys Ser Asp
                325                 330

<210> SEQ ID NO 3
<211> LENGTH: 333
<212> TYPE: PRT
<213> ORGANISM: Arabidopsis sp.

<400> SEQUENCE: 3

Met Asn Gly Leu Glu Thr His Asn Thr Arg Leu Cys Ile Val Gly Ser
 1               5                  10                  15

Gly Pro Ala Ala His Thr Ala Ala Ile Tyr Ala Ala Arg Ala Glu Leu
                20                  25                  30

Lys Pro Leu Leu Phe Glu Gly Trp Met Ala Asn Asp Ile Ala Pro Gly
            35                  40                  45

Gly Gln Leu Thr Thr Thr Thr Asp Val Glu Asn Phe Pro Gly Phe Pro
        50                  55                  60

Glu Gly Ile Leu Gly Val Glu Leu Thr Asp Lys Phe Arg Lys Gln Ser
 65                  70                  75                  80

Glu Arg Phe Gly Thr Thr Ile Phe Thr Glu Thr Val Thr Lys Val Asp
                85                  90                  95

Phe Ser Ser Lys Pro Phe Lys Leu Phe Thr Asp Ser Lys Ala Ile Leu
            100                 105                 110

Ala Asp Ala Val Ile Leu Ala Thr Gly Ala Val Ala Lys Arg Leu Ser
        115                 120                 125

Phe Val Gly Ser Gly Glu Gly Ser Gly Gly Phe Trp Asn Arg Gly Ile
    130                 135                 140

Ser Ala Cys Ala Val Cys Asp Gly Ala Ala Pro Ile Phe Arg Asn Lys
145                 150                 155                 160

Pro Leu Ala Val Ile Gly Gly Gly Asp Ser Ala Met Glu Glu Ala Asn
                165                 170                 175
```

```
Phe Leu Thr Lys Tyr Gly Ser Lys Val Tyr Ile Ile His Arg Arg Asp
            180                 185                 190

Ala Phe Arg Ala Ser Lys Ile Met Gln Gln Arg Ala Leu Ser Asn Pro
        195                 200                 205

Lys Ile Asp Val Ile Trp Asn Ser Ser Val Val Glu Ala Tyr Gly Asp
    210                 215                 220

Gly Glu Arg Asp Val Leu Gly Leu Lys Val Lys Asn Val Val Thr
225                 230                 235                 240

Gly Asp Val Ser Asp Leu Lys Val Ser Gly Leu Phe Ala Ile Gly
                245                 250                 255

His Glu Pro Ala Thr Lys Phe Leu Asp Gly Val Glu Leu Asp Ser
            260                 265                 270

Asp Gly Tyr Val Val Thr Lys Pro Gly Thr Thr Gln Thr Ser Val Pro
        275                 280                 285

Gly Val Phe Ala Ala Gly Asp Val Gln Asp Lys Lys Tyr Arg Gln Ala
    290                 295                 300

Ile Thr Ala Ala Gly Thr Gly Cys Met Ala Ala Leu Asp Ala Glu His
305                 310                 315                 320

Tyr Leu Gln Glu Ile Gly Ser Gln Gln Gly Lys Ser Asp
                325                 330

<210> SEQ ID NO 4
<211> LENGTH: 333
<212> TYPE: PRT
<213> ORGANISM: Unknown Organism
<220> FEATURE:
<223> OTHER INFORMATION: Description of Unknown Organism: Published
      NADPH thioredoxin reductase

<400> SEQUENCE: 4

Met Asn Gly Leu Glu Thr His Asn Thr Arg Leu Cys Ile Val Gly Ser
1               5                   10                  15

Gly Pro Ala Ala His Thr Ala Ala Ile Tyr Ala Ala Arg Ala Glu Leu
            20                  25                  30

Lys Pro Leu Leu Phe Glu Gly Trp Met Ala Asn Asp Ile Ala Pro Gly
        35                  40                  45

Gly Gln Leu Thr Thr Thr Thr Asp Val Glu Asn Phe Pro Gly Phe Pro
    50                  55                  60

Glu Gly Ile Leu Gly Val Glu Leu Thr Asp Lys Phe Arg Lys Gln Ser
65                  70                  75                  80

Glu Arg Phe Gly Thr Thr Ile Phe Thr Glu Thr Val Thr Lys Val Asp
                85                  90                  95

Phe Ser Ser Lys Pro Phe Lys Leu Phe Thr Asp Ser Lys Ala Ile Leu
            100                 105                 110

Ala Asp Ala Val Ile Leu Ala Thr Gly Ala Val Ala Lys Arg Leu Ser
        115                 120                 125

Phe Val Gly Ser Gly Glu Gly Ser Gly Gly Phe Trp Asn Arg Gly Ile
    130                 135                 140

Ser Ala Cys Ala Val Cys Asp Gly Ala Ala Pro Ile Phe Arg Asn Lys
145                 150                 155                 160

Pro Leu Ala Val Ile Gly Gly Gly Asp Ser Ala Met Glu Glu Ala Asn
                165                 170                 175

Phe Leu Thr Lys Tyr Gly Ser Lys Val Tyr Ile Ile His Arg Arg Asp
            180                 185                 190

Ala Phe Arg Ala Ser Lys Ile Met Gln Gln Arg Ala Leu Ser Asn Pro
        195                 200                 205
```

```
Lys Ile Asp Val Ile Trp Asn Ser Ser Val Val Glu Ala Tyr Gly Asp
    210                 215                 220

Gly Glu Arg Asp Val Leu Gly Gly Leu Lys Val Lys Asn Val Val Thr
225                 230                 235                 240

Gly Asp Val Ser Asp Leu Lys Val Ser Gly Leu Phe Phe Ala Ile Gly
                245                 250                 255

His Glu Pro Ala Thr Lys Phe Leu Asp Gly Gly Val Glu Leu Asp Ser
            260                 265                 270

Asp Gly Tyr Val Val Thr Lys Pro Gly Thr Thr Gln Thr Ser Val Pro
        275                 280                 285

Gly Val Phe Ala Ala Gly Asp Val Gln Asp Lys Lys Tyr Arg Gln Ala
    290                 295                 300

Ile Thr Ala Ala Gly Thr Gly Cys Met Ala Ala Leu Asp Ala Glu His
305                 310                 315                 320

Tyr Leu Gln Glu Ile Gly Ser Gln Gln Gly Lys Ser Asp
                325                 330
```

<210> SEQ ID NO 5
<211> LENGTH: 3129
<212> TYPE: DNA
<213> ORGANISM: Arabidopsis thaliana
<220> FEATURE:
<221> NAME/KEY: CDS
<222> LOCATION: (1555)..(1896)

<400> SEQUENCE: 5

```
ctgcaggaat tcattgtact cccagtatca ttatagtgaa agttttggct ctctcgccgg      60
tggttttta cctctattta aaggggtttt ccacctaaaa attctggtat cattctcact     120
ttacttgtta ctttaatttc tcataatctt tggttgaaat tatcacgctt ccgcacacga     180
tatccctaca aatttattat ttgttaaaca ttttcaaacc gcataaaatt ttatgaagtc     240
ccgtctatct ttaatgtagt ctaacatttt catattgaaa tatataattt acttaatttt     300
agcgttggta gaaagcataa tgatttattc ttattcttct tcatataaat gtttaatata     360
caatataaac aaattcttta ccttaagaag gatttcccat tttatatttt aaaaatatat     420
ttatcaaata tttttcaacc acgtaaatct cataataata agttgtttca aaagtaataa     480
aatttaactc cataatttt ttattcgact gatcttaaag caacacccag tgacacaact     540
agccattttt ttctttgaat aaaaaaatcc aattatcatt gtatttttt tatacaatga     600
aaatttcacc aaacaatcat ttgtggtatt tctgaagcaa gtcatgttat gcaaaattct     660
ataattccca tttgacacta cggaagtaac tgaagatctg cttttacatg cgagacacat     720
cttctaaagt aattttaata atagttacta tattcaagat ttcatatatc aaatactcaa     780
tattacttct aaaaaattaa ttagatataa ttaaaatatt actttttaa ttttaagttt     840
aattgttgaa tttgtgacta ttgatttatt attctactat gttaaattg ttttatagat     900
agtttaaagt aaatataagt aatgtagtag agtgttagag tgttacccta aaccataaac     960
tataagattt atggtggact aattttcata tatttcttat tgcttttacc ttttcttggt    1020
atgtaagtcc gtaactggaa ttactgtggg ttgccatggc actctgtggt cttttggttc    1080
atgcatggat gcttgcgcaa gaaaagaca agaacaaag aaaaaagaca aaacagagag    1140
acaaaacgca atcacacaac caactcaaat tagtcactgg ctgatcaaga tcgccgcgtc    1200
catgtatgtc taaatgccat gcaaagcaac acgtgcttaa catgcacttt aaatggctca    1260
cccatctcaa cccacacaca aacacattgc cttttttcttc atcatcacca caaccacctg    1320
```

-continued

```
tatatattca ttctcttccg ccacctcaat ttcttcactt caacacacgt caacctgcat    1380
atgcgtgtca tcccatgccc aaatctccat gcatgttcca accaccttct ctcttatata    1440 ataccctataa atacctctaa tatcactcac ttctttcatc atccatccat ccagagtact   1500
actactctac tactataata ccccaaccca actcatattc aatactactc tact atg     1557
                                                            Met
                                                            1 gct tcg gaa gaa gga caa gtg atc gcc tgc cac acc gtt gag aca tgg     1605
Ala Ser Glu Glu Gly Gln Val Ile Ala Cys His Thr Val Glu Thr Trp
      5                  10                  15 aac gag cag ctt cag aag gct aat gaa tcc aaa act ctt gtg gtg gtt     1653
Asn Glu Gln Leu Gln Lys Ala Asn Glu Ser Lys Thr Leu Val Val Val
 20                  25                  30 gat ttc acg gct tct tgg tgt gga cca tgt cgt ttc atc gct cca ttc     1701
Asp Phe Thr Ala Ser Trp Cys Gly Pro Cys Arg Phe Ile Ala Pro Phe
 35                  40                  45 ttt gct gat ttg gct aag aaa ctt cct aac gtg ctt ttc ctc aag gtt     1749
Phe Ala Asp Leu Ala Lys Lys Leu Pro Asn Val Leu Phe Leu Lys Val
 50                  55                  60                   65 gat act gat gaa ttg aag tcg gtg gca agt gat tgg gcg ata cag gcg     1797
Asp Thr Asp Glu Leu Lys Ser Val Ala Ser Asp Trp Ala Ile Gln Ala
             70                  75                  80 atg cca acc ttc atg ttt ttg aag gaa ggg aag att ttg gac aaa gtt     1845
Met Pro Thr Phe Met Phe Leu Lys Glu Gly Lys Ile Leu Asp Lys Val
                 85                  90                  95 gtt gga gcc aag aaa gat gag ctt cag tct acc att gcc aaa cac ttg     1893
Val Gly Ala Lys Lys Asp Glu Leu Gln Ser Thr Ile Ala Lys His Leu
                100                 105                 110 gct taagcttaat aagtatgaac taaaatgcat gtaggtgtaa gagctcatgg          1946
Ala agagcatgga atattgtatc cgaccatgta acagtataat aactgagctc catctcactt   2006
cttctatgaa taaacaaagg atgttatgat atattaacac tctatctatg cacccttattg  2066 ttctatgata aatttcctct tattattata aatcatctga atcgtgacgg cttatggaat   2126
gcttcaaata gtacaaaaac aaatgtgtac tataagactt tctaaacaat tctaacttta   2186
gcattgtgaa cgagacataa gtgttaagaa gacataacaa ttataatgga agaagtttgt   2246
ctccatttat atattatata ttacccactt atgtattata ttaggatgtt aaggagacat   2306
aacaattata aagagagaag tttgtatcca tttatatatt atatactacc catttatata   2366
ttatacttat ccactttttt aatgtcttta taaggtttga tccatgatat ttctaatatt   2426
ttagttgata tgtatatgaa agggtactat ttgaactctc ttactctgta taaaggttgg   2486
atcatcctta aagtgggtct attaattttt attgcttctt acagataaaa aaaaaattat    2546
gagttggttt gataaaatat tgaaggattt aaaataataa taaataataa ataacatata   2606
atatatgtat ataaatttat tataatataa catttatcta taaaaagta aatattgtca    2666 taaatctata caatcgttta gccttgctgg acgactctca attatttaaa cgagagtaaa   2726
catatttgac ttttttggtta tttaacaaat tattatttaa cactatatga aatttttttt   2786
ttttatcggc aaggaaataa aattaaatta ggagggacaa tggtgtgtcc caatccttat   2846
acaaccaact tccacaggaa ggtcaggtcg gggacaacaa aaaacaggc aagggaaatt    2906 ttttaatttg ggttgtcttg tttgctgcat aatttatgca gtaaaacact acacataacc   2966
cttttagcag tagagcaatg gttgaccgtg tgcttagctt cttttatttt attttttttat  3026 cagcaaagaa taaataaaat aaaatgagac acttcaggga tgtttcaacc cttatacaaa   3086
```

```
accccaaaaa caagtttcct agcaccctac caactaaggt acc                      3129

<210> SEQ ID NO 6
<211> LENGTH: 114
<212> TYPE: PRT
<213> ORGANISM: Arabidopsis thaliana

<400> SEQUENCE: 6

Met Ala Ser Glu Glu Gly Gln Val Ile Ala Cys His Thr Val Glu Thr
 1               5                  10                  15

Trp Asn Glu Gln Leu Gln Lys Ala Asn Glu Ser Lys Thr Leu Val Val
                20                  25                  30

Val Asp Phe Thr Ala Ser Trp Cys Gly Pro Cys Arg Phe Ile Ala Pro
            35                  40                  45

Phe Phe Ala Asp Leu Ala Lys Lys Leu Pro Asn Val Leu Phe Leu Lys
        50                  55                  60

Val Asp Thr Asp Glu Leu Lys Ser Val Ala Ser Asp Trp Ala Ile Gln
 65                  70                  75                  80

Ala Met Pro Thr Phe Met Phe Leu Lys Glu Gly Lys Ile Leu Asp Lys
                85                  90                  95

Val Val Gly Ala Lys Lys Asp Glu Leu Gln Ser Thr Ile Ala Lys His
            100                 105                 110

Leu Ala

<210> SEQ ID NO 7
<211> LENGTH: 3888
<212> TYPE: DNA
<213> ORGANISM: Unknown Organism
<220> FEATURE:
<221> NAME/KEY: CDS
<222> LOCATION: (1555)..(1908)
<221> NAME/KEY: CDS
<222> LOCATION: (2149)..(2655)
<223> OTHER INFORMATION: Description of Unknown Organism: Phaseolin
      promoter-oleosin Trxh-phaseolin terminator

<400> SEQUENCE: 7
ctgcaggaat tcattgtact cccagtatca ttatagtgaa agttttggct ctctcgccgg      60
tggtttttta cctctatttta aagggggtttt ccacctaaaa attctggtat cattctcact    120
ttacttgtta ctttaatttc tcataatctt tggttgaaat tatcacgctt ccgcacacga    180
tatccctaca aatttattat ttgttaaaca ttttcaaacc gcataaaatt ttatgaagtc    240
ccgtctatct ttaatgtagt ctaacatttt catattgaaa tatataattt acttaatttt    300
agcgttggta gaaagcataa tgattttattc ttattcttct tcatataaat gtttaatata    360
caatataaac aaattcttta ccttaagaag gatttcccat tttatatttt aaaaatatat    420
ttatcaaata tttttcaacc acgtaaatct cataataata agttgtttca aaagtaataa    480
aatttaactc cataatttttt ttattcgact gatcttaaag caacacccag tgacacaact    540
agccattttt ttctttgaat aaaaaaatcc aattatcatt gtatttttttt tatacaatga    600 aaatttcacc aaacaatcat tgtggtatt tctgaagcaa gtcatgttat gcaaaattct    660
ataattccca tttgacacta cggaagtaac tgaagatctg cttttacatg cgagacacat    720
cttctaaagt aatttttaata atagttacta tattcaagat ttcatatatc aaatactcaa    780
tattacttct aaaaaattaa ttagatataa ttaaaatatt acttttttaa ttttaagttt    840
aattgttgaa tttgtgacta ttgatttatt attctactat gtttaaattg ttttatagat    900
```

```
agtttaaagt aaatataagt aatgtagtag agtgttagag tgttacccta aaccataaac    960
tataagattt atggtggact aattttcata tatttcttat tgcttttacc ttttcttggt   1020
atgtaagtcc gtaactggaa ttactgtggg ttgccatggc actctgtggt cttttggttc   1080
atgcatggat gcttgcgcaa gaaaaagaca agaacaaag aaaaaagaca aaacagagag    1140
acaaaacgca atcacacaac caactcaaat tagtcactgg ctgatcaaga tcgccgcgtc   1200
catgtatgtc taaatgccat gcaaagcaac acgtgcttaa catgcacttt aaatggctca   1260
cccatctcaa cccacacaca aacacattgc cttttcttc atcatcacca caaccacctg    1320
tatatattca ttctcttccg ccacctcaat ttcttcactt caacacacgt caacctgcat   1380
atgcgtgtca tcccatgccc aaatctccat gcatgttcca accaccttct ctcttatata   1440
ataccctataa atacctctaa tatcactcac ttctttcatc atccatccat ccagagtact  1500
actactctac tactataata ccccaaccca actcatattc aatactactc tact atg     1557
                                                                Met
                                                                 1 gcg gat aca gct aga gga acc cat cac gat atc atc ggc aga gac cag     1605
Ala Asp Thr Ala Arg Gly Thr His His Asp Ile Ile Gly Arg Asp Gln
              5                  10                  15 tac ccg atg atg ggc cga gac cga gac cag tac cag atg tcc gga cga     1653
Tyr Pro Met Met Gly Arg Asp Arg Asp Gln Tyr Gln Met Ser Gly Arg
         20                  25                  30 gga tct gac tac tcc aag tct agg cag att gct aaa gct gca act gct     1701
Gly Ser Asp Tyr Ser Lys Ser Arg Gln Ile Ala Lys Ala Ala Thr Ala
     35                  40                  45 gtc aca gct ggt ggt tcc ctc ctt gtt ctc tcc agc ctt acc ctt gtt     1749
Val Thr Ala Gly Gly Ser Leu Leu Val Leu Ser Ser Leu Thr Leu Val
 50                  55                  60                  65 gga act gtc ata gct ttg act gtt gca aca cct ctg ctc gtt atc ttc     1797
Gly Thr Val Ile Ala Leu Thr Val Ala Thr Pro Leu Leu Val Ile Phe
                 70                  75                  80 agc cca atc ctt gtc ccg gct ctc atc aca gtt gca ctc ctc atc acc     1845
Ser Pro Ile Leu Val Pro Ala Leu Ile Thr Val Ala Leu Leu Ile Thr
             85                  90                  95 ggt ttt ctt tcc tct gga ggg ttt ggc att gcc gct ata acc gtt ttc     1893
Gly Phe Leu Ser Ser Gly Gly Phe Gly Ile Ala Ala Ile Thr Val Phe
        100                 105                 110 tct tgg att tac aag taagcacaca tttatcatct tacttcataa ttttgtgcaa     1948
Ser Trp Ile Tyr Lys
        115 tatgtgcatg catgtgttga gccagtagct ttggatcaat ttttttggtc gaataacaaa   2008
tgtaacaata agaaattgca aattctaggg aacatttggt taactaaata cgaaatttga   2068
cctagctagc ttgaatgtgt ctgtgtatat catctatata ggtaaaatgc ttggtatgat   2128
acctattgat tgtgaatagg tac gca acg gga gag cac cca cag gga tca gac  2181
                      Tyr Ala Thr Gly Glu His Pro Gln Gly Ser Asp
                              120                 125 aag ttg gac agt gca agg atg aag ttg gga agc aaa gct cag gat ctg     2229
Lys Leu Asp Ser Ala Arg Met Lys Leu Gly Ser Lys Ala Gln Asp Leu
130                 135                 140                 145 aaa gac aga gct cag tac tac gga cag caa cat act ggt ggg gaa cat     2277
Lys Asp Arg Ala Gln Tyr Tyr Gly Gln Gln His Thr Gly Gly Glu His
                150                 155                 160 gac cgt gac cgt act cgt ggt ggc cag cac act acc atg gct tcg gaa     2325
Asp Arg Asp Arg Thr Arg Gly Gly Gln His Thr Thr Met Ala Ser Glu
            165                 170                 175 gaa gga caa gtg atc gcc tgc cac acc gtt gag aca tgg aac gag cag     2373
```

```
                                        -continued
Glu Gly Gln Val Ile Ala Cys His Thr Val Glu Thr Trp Asn Glu Gln
        180                 185                 190 ctt cag aag gct aat gaa tcc aaa act ctt gtg gtg gtt gat ttc acg      2421
Leu Gln Lys Ala Asn Glu Ser Lys Thr Leu Val Val Val Asp Phe Thr
    195                 200                 205 gct tct tgg tgt gga cca tgt cgt ttc atc gct cca ttc ttt gct gat      2469
Ala Ser Trp Cys Gly Pro Cys Arg Phe Ile Ala Pro Phe Phe Ala Asp
210                 215                 220                 225 ttg gct aag aaa ctt cct aac gtg ctt ttc ctc aag gtt gat act gat      2517
Leu Ala Lys Lys Leu Pro Asn Val Leu Phe Leu Lys Val Asp Thr Asp
                230                 235                 240 gaa ttg aag tcg gtg gca agt gat tgg gcg ata cag gcg atg cca acc      2565
Glu Leu Lys Ser Val Ala Ser Asp Trp Ala Ile Gln Ala Met Pro Thr
            245                 250                 255 ttc atg ttt ttg aag gaa ggg aag att ttg gac aaa gtt gtt gga gcc      2613
Phe Met Phe Leu Lys Glu Gly Lys Ile Leu Asp Lys Val Val Gly Ala
        260                 265                 270 aag aaa gat gag ctt cag tct acc att gcc aaa cac ttg gct              2655
Lys Lys Asp Glu Leu Gln Ser Thr Ile Ala Lys His Leu Ala
    275                 280                 285 taagcttaat aagtatgaac taaaatgcat gtaggtgtaa gagctcatgg agagcatgga    2715
atattgtatc cgaccatgta acagtataat aactgagctc catctcactt cttctatgaa    2775
taaacaaagg atgttatgat atattaacac tctatctatg caccttattg ttctatgata    2835
aatttcctct tattattata aatcatctga atcgtgacgg cttatggaat gcttcaaata    2895
gtacaaaaac aaatgtgtac tataagactt tctaaacaat tctaacttta gcattgtgaa    2955
cgagacataa gtgttaagaa gacataacaa ttataatgga agaagtttgt ctccatttat    3015
atattatata ttacccactt atgtattata ttaggatgtt aaggagacat aacaattata    3075
aagagagaag tttgtatcca tttatatatt atatactacc catttatata ttatacttat    3135
ccacttattt aatgtcttta taaggtttga tccatgatat ttctaatatt ttagttgata    3195
tgtatatgaa agggtactat ttgaactctc ttactctgta taaaggttgg atcatcctta    3255
aagtgggtct atttaattt attgcttcct acagataaaa aaaaaattat gagttggttt     3315
gataaaatat tgaaggattt aaaataataa taaataataa ataacatata atatatgtat    3375
ataaatttat tataatataa catttatcta taaaaaagta aatattgtca taaatctata    3435
caatcgttta gccttgctgg acgactctca attatttaaa cgagagtaaa catatttgac    3495
ttttggtta tttaacaaat tattatttaa cactatatga aatttttttt ttttatcggc     3555
aaggaaataa aattaaatta ggagggacaa tggtgtgtcc caatccttat acaaccaact    3615
tccacaggaa ggtcaggtcg gggacaacaa aaaacaggc aagggaaatt ttttaatttg     3675
ggttgtcttg tttgctgcat aatttatgca gtaaaacact acacataacc cttttagcag    3735
tagagcaatg gttgaccgtg tgcttagctt ctttttatttt atttttttat cagcaaagaa    3795
taaataaaat aaaatgagac acttcaggga tgtttcaacc cttatacaaa accccaaaaa    3855
caagtttcct agcaccctac caactaaggt acc                                  3888

<210> SEQ ID NO 8
<211> LENGTH: 118
<212> TYPE: PRT
<213> ORGANISM: Unknown Organism
<220> FEATURE:
<223> OTHER INFORMATION: Description of Unknown Organism: Phaseolin
      promoter-oleosin Trxh-phaseolin terminator

<400> SEQUENCE: 8
```

```
Met Ala Asp Thr Ala Arg Gly Thr His His Asp Ile Ile Gly Arg Asp
  1               5                  10                  15

Gln Tyr Pro Met Met Gly Arg Asp Arg Asp Gln Tyr Gln Met Ser Gly
             20                  25                  30

Arg Gly Ser Asp Tyr Ser Lys Ser Arg Gln Ile Ala Lys Ala Ala Thr
         35                  40                  45

Ala Val Thr Ala Gly Gly Ser Leu Leu Val Leu Ser Ser Leu Thr Leu
 50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                 85                  90                  95

Thr Gly Phe Leu Ser Ser Gly Gly Phe Gly Ile Ala Ala Ile Thr Val
            100                 105                 110

Phe Ser Trp Ile Tyr Lys
            115
```

<210> SEQ ID NO 9
<211> LENGTH: 169
<212> TYPE: PRT
<213> ORGANISM: Unknown Organism
<220> FEATURE:
<223> OTHER INFORMATION: Description of Unknown Organism: Phaseolin
      promoter-oleosin Trxh-phaseolin terminator

<400> SEQUENCE: 9

```
Tyr Ala Thr Gly Glu His Pro Gln Gly Ser Asp Lys Leu Asp Ser Ala
  1               5                  10                  15

Arg Met Lys Leu Gly Ser Lys Ala Gln Asp Leu Lys Asp Arg Ala Gln
             20                  25                  30

Tyr Tyr Gly Gln Gln His Thr Gly Gly Glu His Asp Arg Asp Arg Thr
         35                  40                  45

Arg Gly Gly Gln His Thr Thr Met Ala Ser Glu Glu Gly Gln Val Ile
 50                  55                  60

Ala Cys His Thr Val Glu Thr Trp Asn Glu Gln Leu Gln Lys Ala Asn
65                  70                  75                  80

Glu Ser Lys Thr Leu Val Val Val Asp Phe Thr Ala Ser Trp Cys Gly
                 85                  90                  95

Pro Cys Arg Phe Ile Ala Pro Phe Phe Ala Asp Leu Ala Lys Lys Leu
            100                 105                 110

Pro Asn Val Leu Phe Leu Lys Val Asp Thr Asp Glu Leu Lys Ser Val
        115                 120                 125

Ala Ser Asp Trp Ala Ile Gln Ala Met Pro Thr Phe Met Phe Leu Lys
    130                 135                 140

Glu Gly Lys Ile Leu Asp Lys Val Val Gly Ala Lys Lys Asp Glu Leu
145                 150                 155                 160

Gln Ser Thr Ile Ala Lys His Leu Ala
                165
```

<210> SEQ ID NO 10
<211> LENGTH: 3888
<212> TYPE: DNA
<213> ORGANISM: Unknown Organism
<220> FEATURE:
<221> NAME/KEY: CDS
<222> LOCATION: (1555)..(2250)
<221> NAME/KEY: CDS
<222> LOCATION: (2491)..(2655)

<223> OTHER INFORMATION: Description of Unknown Organism: Phaseolin
      promoter-Trxh oleosin-phaseolin terminator

<400> SEQUENCE: 10

| | | | | |
|---|---|---|---|---|
| ctgcaggaat tcattgtact cccagtatca ttatagtgaa agttttggct ctctcgccgg | | | | 60 |
| tggttttta cctctattta aaggggtttt ccacctaaaa attctggtat cattctcact | | | | 120 |
| ttacttgtta ctttaatttc tcataatctt tggttgaaat tatcacgctt ccgcacacga | | | | 180 |
| tatccctaca aatttattat ttgttaaaca ttttcaaacc gcataaaatt ttatgaagtc | | | | 240 |
| ccgtctatct ttaatgtagt ctaacatttt catattgaaa tatataattt acttaatttt | | | | 300 |
| agcgttggta gaaagcataa tgatttattc ttattcttct tcatataaat gtttaatata | | | | 360 |
| caatataaac aaattcttta ccttaagaag gatttcccat tttatatttt aaaaatatat | | | | 420 |
| ttatcaaata ttttcaacc acgtaaatct cataataata agttgtttca aaagtaataa | | | | 480 |
| aatttaactc cataattttt ttattcgact gatcttaaag caacacccag tgacacaact | | | | 540 |
| agccattttt ttctttgaat aaaaaaatcc aattatcatt gtatttttt tatacaatga | | | | 600 |
| aaatttcacc aaacaatcat ttgtggtatt tctgaagcaa gtcatgttat gcaaaattct | | | | 660 |
| ataattccca tttgacacta cggaagtaac tgaagatctg cttttacatg cgagacacat | | | | 720 |
| cttctaaagt aattttaata atagttacta tattcaagat ttcatatatc aaatactcaa | | | | 780 |
| tattacttct aaaaaattaa ttagatataa ttaaaatatt acttttttaa ttttaagttt | | | | 840 |
| aattgttgaa tttgtgacta ttgatttatt attctactat gttaaattg ttttatagat | | | | 900 |
| agtttaaagt aaatataagt aatgtagtag agtgttagag tgttacccta aaccataaac | | | | 960 |
| tataagattt atggtggact aattttcata tatttcttat tgcttttacc ttttcttggt | | | | 1020 |
| atgtaagtcc gtaactggaa ttactgtggg ttgccatggc actctgtggt cttttggttc | | | | 1080 |
| atgcatggat gcttgcgcaa gaaaagaca aagaacaaag aaaaagaca aacagagag | | | | 1140 |
| acaaaacgca atcacacaac caactcaaat tagtcactgg ctgatcaaga tcgccgcgtc | | | | 1200 |
| catgtatgtc taaatgccat gcaaagcaac acgtgcttaa catgcacttt aaatggctca | | | | 1260 |
| cccatctcaa cccacacaca aacacattgc ctttttcttc atcatcacca caaccacctg | | | | 1320 |
| tatatattca ttctcttccg ccacctcaat ttcttcactt caacacacgt caacctgcat | | | | 1380 |
| atgcgtgtca tcccatgccc aaatctccat gcatgttcca accaccttct ctcttatata | | | | 1440 |
| atacctataa atacctctaa tatcactcac ttctttcatc atccatccat ccagagtact | | | | 1500 |
| actactctac tactataata ccccaaccca actcatattc aatactactc tact atg | | | | 1557 |
| | | | | Met 1 |
| gct tcg gaa gaa gga caa gtg atc gcc tgc cac acc gtt gag aca tgg | | | | 1605 |
| Ala Ser Glu Glu Gly Gln Val Ile Ala Cys His Thr Val Glu Thr Trp | | | | |
|     5                     10                  15 | | | | |
| aac gag cag ctt cag aag gct aat gaa tcc aaa act ctt gtg gtg gtt | | | | 1653 |
| Asn Glu Gln Leu Gln Lys Ala Asn Glu Ser Lys Thr Leu Val Val Val | | | | |
|          20                  25                  30 | | | | |
| gat ttc acg gct tct tgg tgt gga cca tgt cgt ttc atc gct cca ttc | | | | 1701 |
| Asp Phe Thr Ala Ser Trp Cys Gly Pro Cys Arg Phe Ile Ala Pro Phe | | | | |
|      35                  40                  45 | | | | |
| ttt gct gat ttg gct aag aaa ctt cct aac gtg ctt ttc ctc aag gtt | | | | 1749 |
| Phe Ala Asp Leu Ala Lys Lys Leu Pro Asn Val Leu Phe Leu Lys Val | | | | |
| 50                  55                  60                  65 | | | | |
| gat act gat gaa ttg aag tcg gtg gca agt gat tgg gcg ata cag gcg | | | | 1797 |
| Asp Thr Asp Glu Leu Lys Ser Val Ala Ser Asp Trp Ala Ile Gln Ala | | | | |
|              70                  75                  80 | | | | |

-continued

| | |
|---|---|
| atg cca acc ttc atg ttt ttg aag gaa ggg aag att ttg gac aaa gtt<br>Met Pro Thr Phe Met Phe Leu Lys Glu Gly Lys Ile Leu Asp Lys Val<br>               85                 90               95 | 1845 |
| gtt gga gcc aag aaa gat gag ctt cag tct acc att gcc aaa cac ttg<br>Val Gly Ala Lys Lys Asp Glu Leu Gln Ser Thr Ile Ala Lys His Leu<br>        100                105               110 | 1893 |
| gct atg gcg gat aca gct aga gga acc cat cac gat atc atc ggc aga<br>Ala Met Ala Asp Thr Ala Arg Gly Thr His His Asp Ile Ile Gly Arg<br>115                120               125 | 1941 |
| gac cag tac ccg atg atg ggc cga gac cga gac cag tac cag atg tcc<br>Asp Gln Tyr Pro Met Met Gly Arg Asp Arg Asp Gln Tyr Gln Met Ser<br>130                135             140               145 | 1989 |
| gga cga gga tct gac tac tcc aag tct agg cag att gct aaa gct gca<br>Gly Arg Gly Ser Asp Tyr Ser Lys Ser Arg Gln Ile Ala Lys Ala Ala<br>                150               155               160 | 2037 |
| act gct gtc aca gct ggt ggt tcc ctc ctt gtt ctc tcc agc ctt acc<br>Thr Ala Val Thr Ala Gly Gly Ser Leu Leu Val Leu Ser Ser Leu Thr<br>        165                170               175 | 2085 |
| ctt gtt gga act gtc ata gct ttg act gtt gca aca cct ctg ctc gtt<br>Leu Val Gly Thr Val Ile Ala Leu Thr Val Ala Thr Pro Leu Leu Val<br>                180               185               190 | 2133 |
| atc ttc agc cca atc ctt gtc ccg gct ctc atc aca gtt gca ctc ctc<br>Ile Phe Ser Pro Ile Leu Val Pro Ala Leu Ile Thr Val Ala Leu Leu<br>        195                200               205 | 2181 |
| atc acc ggt ttt ctt tcc tct gga ggg ttt ggc att gcc gct ata acc<br>Ile Thr Gly Phe Leu Ser Ser Gly Gly Phe Gly Ile Ala Ala Ile Thr<br>210                215               220               225 | 2229 |
| gtt ttc tct tgg att tac aag taagcacaca tttatcatct tacttcataa<br>Val Phe Ser Trp Ile Tyr Lys<br>                230 | 2280 |
| ttttgtgcaa tatgtgcatg catgtgttga gccagtagct ttggatcaat ttttttggtc | 2340 |
| gaataacaaa tgtaacaata agaaattgca aattctaggg aacatttggt taactaaata | 2400 |
| cgaaatttga cctagctagc ttgaatgtgt ctgtgtatat catctatata ggtaaaatgc | 2460 |
| ttggtatgat acctattgat tgtgaatagg tac gca acg gga gag cac cca cag<br>                                                       Tyr Ala Thr Gly Glu His Pro Gln<br>                                                                   235                             240 | 2514 |
| gga tca gac aag ttg gac agt gca agg atg aag ttg gga agc aaa gct<br>Gly Ser Asp Lys Leu Asp Ser Ala Arg Met Lys Leu Gly Ser Lys Ala<br>                245               250                 255 | 2562 |
| cag gat ctg aaa gac aga gct cag tac tac gga cag caa cat act ggt<br>Gln Asp Leu Lys Asp Arg Ala Gln Tyr Tyr Gly Gln Gln His Thr Gly<br>        260                265               270 | 2610 |
| ggg gaa cat gac cgt gac cgt act cgt ggt ggc cag cac act act<br>Gly Glu His Asp Arg Asp Arg Thr Arg Gly Gly Gln His Thr Thr<br>275                280               285 | 2655 |
| taagcttaat aagtatgaac taaaatgcat gtaggtgtaa gagctcatgg agagcatgga | 2715 |
| atattgtatc cgaccatgta acagtataat aactgagctc catctcactt cttctatgaa | 2775 |
| taaacaaagg atgttatgat atattaacac tctatctatg caccttattg ttctatgata | 2835 |
| aatttcctct tattattata aatcatctga atcgtgacgg cttatggaat gcttcaaata | 2895 |
| gtacaaaaac aaatgtgtac tataagactt tctaaacaat tctaactttta gcattgtgaa | 2955 |
| cgagacataa gtgttaagaa gacataacaa ttataatgga agaagtttgt ctccatttat | 3015 |
| atattatata ttacccactt atgtattata ttaggatgtt aaggagacat aacaattata | 3075 |
| aagagagaag tttgtatcca tttatatatt atatactacc catttatata ttatacttat | 3135 |
| ccacttattt aatgtctttta taaggtttga tccatgatat ttctaatatt ttagttgata | 3195 |

-continued

```
tgtatatgaa agggtactat ttgaactctc ttactctgta taaaggttgg atcatcctta    3255
aagtgggtct atttaatttt attgcttctt acagataaaa aaaaaattat gagttggttt    3315
gataaaatat tgaaggattt aaaataataa taaataataa ataacatata atatatgtat    3375
ataaatttat tataatataa catttatcta taaaaaagta aatattgtca taaatctata    3435
caatcgttta gccttgctgg acgactctca attatttaaa cgagagtaaa catatttgac    3495
tttttggtta tttaacaaat tattatttaa cactatatga aatttttttt ttttatcggc    3555
aaggaaataa aattaaatta ggagggacaa tggtgtgtcc caatccttat acaaccaact    3615
tccacaggaa ggtcaggtcg gggacaacaa aaaaacaggc aagggaaatt ttttaatttg    3675
ggttgtcttg tttgctgcat aatttatgca gtaaaacact acacataacc cttttagcag    3735
tagagcaatg gttgaccgtg tgcttagctt cttttatttt atttttttat cagcaaagaa    3795
taaataaaat aaaatgagac acttcaggga tgtttcaacc cttatacaaa accccaaaaa    3855
caagtttcct agcaccctac caactaaggt acc                                 3888
```

<210> SEQ ID NO 11
<211> LENGTH: 232
<212> TYPE: PRT
<213> ORGANISM: Unknown Organism
<220> FEATURE:
<223> OTHER INFORMATION: Description of Unknown Organism: Phaseolin promoter-Trxh oleosin-phaseolin terminator

<400> SEQUENCE: 11

```
Met Ala Ser Glu Glu Gly Gln Val Ile Ala Cys His Thr Val Glu Thr
  1               5                  10                  15

Trp Asn Glu Gln Leu Gln Lys Ala Asn Glu Ser Lys Thr Leu Val Val
             20                  25                  30

Val Asp Phe Thr Ala Ser Trp Cys Gly Pro Cys Arg Phe Ile Ala Pro
         35                  40                  45

Phe Phe Ala Asp Leu Ala Lys Lys Leu Pro Asn Val Leu Phe Leu Lys
     50                  55                  60

Val Asp Thr Asp Glu Leu Lys Ser Val Ala Ser Asp Trp Ala Ile Gln
 65                  70                  75                  80

Ala Met Pro Thr Phe Met Phe Leu Lys Glu Gly Lys Ile Leu Asp Lys
                 85                  90                  95

Val Val Gly Ala Lys Lys Asp Glu Leu Gln Ser Thr Ile Ala Lys His
            100                 105                 110

Leu Ala Met Ala Asp Thr Ala Arg Gly Thr His His Asp Ile Ile Gly
        115                 120                 125

Arg Asp Gln Tyr Pro Met Met Gly Arg Asp Arg Asp Gln Tyr Gln Met
    130                 135                 140

Ser Gly Arg Gly Ser Asp Tyr Ser Lys Ser Arg Gln Ile Ala Lys Ala
145                 150                 155                 160

Ala Thr Ala Val Thr Ala Gly Gly Ser Leu Leu Val Leu Ser Ser Leu
                165                 170                 175

Thr Leu Val Gly Thr Val Ile Ala Leu Thr Val Ala Thr Pro Leu Leu
            180                 185                 190

Val Ile Phe Ser Pro Ile Leu Val Pro Ala Leu Ile Thr Val Ala Leu
        195                 200                 205

Leu Ile Thr Gly Phe Leu Ser Ser Gly Gly Phe Gly Ile Ala Ala Ile
    210                 215                 220

Thr Val Phe Ser Trp Ile Tyr Lys
225                 230
```

<210> SEQ ID NO 12
<211> LENGTH: 55
<212> TYPE: PRT
<213> ORGANISM: Unknown Organism
<220> FEATURE:
<223> OTHER INFORMATION: Description of Unknown Organism: Phaseolin
      promoter-Trxh oleosin-phaseolin terminator

<400> SEQUENCE: 12

Tyr Ala Thr Gly Glu His Pro Gln Gly Ser Asp Lys Leu Asp Ser Ala
 1               5                  10                  15

Arg Met Lys Leu Gly Ser Lys Ala Gln Asp Leu Lys Asp Arg Ala Gln
            20                  25                  30

Tyr Tyr Gly Gln Gln His Thr Gly Gly Glu His Asp Arg Asp Arg Thr
        35                  40                  45

Arg Gly Gly Gln His Thr Thr
    50                  55

<210> SEQ ID NO 13
<211> LENGTH: 3787
<212> TYPE: DNA
<213> ORGANISM: Unknown Organism
<220> FEATURE:
<221> NAME/KEY: CDS
<222> LOCATION: (1555)..(2553)
<223> OTHER INFORMATION: Description of Unknown Organism: Phaseolin
      promoter-thioredoxin reductase-phaseolin
      terminator

<400> SEQUENCE: 13

```
ctgcaggaat tcattgtact cccagtatca ttatagtgaa agttttggct ctctcgccgg      60 tggttttta cctctattta aaggggtttt ccacctaaaa attctggtat cattctcact     120
ttacttgtta cttaattttc tcataatctt tggttgaaat tatcacgctt ccgcacacga     180
tatccctaca aatttattat ttgttaaaca ttttcaaacc gcataaaatt ttatgaagtc     240
ccgtctatct ttaatgtagt ctaacatttt catattgaaa tatataattt acttaatttt     300
agcgttggta gaaagcataa tgatttattc ttattcttct tcatataaat gtttaatata     360
caatataaac aaattcttta ccttaagaag gatttcccat tttatatttt aaaaatatat     420
ttatcaaata tttttcaacc acgtaaatct cataataata agttgtttca aaagtaataa     480
aatttaactc cataattttt ttattcgact gatcttaaag caacacccag tgacacaact     540
agccattttt ttctttgaat aaaaaaatcc aattatcatt gtatttttt tatacaatga     600 aaatttcacc aaacaatcat ttgtggtatt tctgaagcaa gtcatgttat gcaaaattct     660
ataattccca tttgacacta cggaagtaac tgaagatctg cttttacatg cgagacacat     720
cttctaaagt aattttaata atagttacta tattcaagat ttcatatatc aaatactcaa     780
tattacttct aaaaaattaa ttagatataa ttaaaatatt acttttttaa ttttaagttt     840
aattgttgaa tttgtgacta ttgatttatt attctactat gtttaaattg ttttatagat     900
agtttaaagt aaatataagt aatgtagtag agtgttagag tgttacccta aaccataaac     960
tataagattt atggtggact aattttcata tatttcttat tgcttttacc ttttcttggt    1020
atgtaagtcc gtaactggaa ttactgtggg ttgccatggc actctgtggt cttttggttc    1080
atgcatggat gcttgcgcaa gaaaagaca agaacaaag aaaaaagaca aaacagagag    1140
acaaaacgca atcacacaac caactcaaat tagtcactgg ctgatcaaga tcgccgcgtc    1200
```

-continued

```
catgtatgtc taaatgccat gcaaagcaac acgtgcttaa catgcacttt aaatggctca    1260
cccatctcaa cccacacaca aacacattgc cttttttcttc atcatcacca caaccacctg   1320
tatatattca ttctcttccg ccacctcaat ttcttcactt caacacacgt caacctgcat    1380
atgcgtgtca tcccatgccc aaatctccat gcatgttcca accaccttct ctcttatata   1440
atacctataa atacctctaa tatcactcac ttctttcatc atccatccat ccagagtact   1500
actactctac tactataata ccccaaccca actcatattc aatactactc tact atg    1557
                                                              Met
                                                              1
```

```
aat ggt ctc gaa act cac aac aca agg ctc tgt atc gta gga agt ggc     1605
Asn Gly Leu Glu Thr His Asn Thr Arg Leu Cys Ile Val Gly Ser Gly
         5                  10                  15 cca gcg gca cac acg gcg gcg att tac gca gct agg gct gaa ctt aaa     1653
Pro Ala Ala His Thr Ala Ala Ile Tyr Ala Ala Arg Ala Glu Leu Lys
     20                  25                  30 cct ctt ctc ttc gaa gga tgg atg gct aac gac atc gct ccc ggt ggt     1701
Pro Leu Leu Phe Glu Gly Trp Met Ala Asn Asp Ile Ala Pro Gly Gly
 35                  40                  45 caa cta aca acc acc acc gac gtc gag aat ttc ccc gga ttt cca gaa     1749
Gln Leu Thr Thr Thr Thr Asp Val Glu Asn Phe Pro Gly Phe Pro Glu
 50                  55                  60                  65 ggt att ctc gga gta gag ctc act gac aaa ttc cgt aaa caa tcg gag     1797
Gly Ile Leu Gly Val Glu Leu Thr Asp Lys Phe Arg Lys Gln Ser Glu
             70                  75                  80 cga ttc ggt act acg ata ttt aca gag acg gtg acg aaa gtc gat ttc     1845
Arg Phe Gly Thr Thr Ile Phe Thr Glu Thr Val Thr Lys Val Asp Phe
             85                  90                  95 tct tcg aaa ccg ttt aag cta ttc aca gat tca aaa gcc att ctc gct     1893
Ser Ser Lys Pro Phe Lys Leu Phe Thr Asp Ser Lys Ala Ile Leu Ala
            100                 105                 110 gac gct gtg att ctc gct act gga gct gtg gct aag cgg ctt agc ttc     1941
Asp Ala Val Ile Leu Ala Thr Gly Ala Val Ala Lys Arg Leu Ser Phe
        115                 120                 125 gtt gga tct ggt gaa ggt tct gga ggt ttc tgg aac cgt gga atc tcc     1989
Val Gly Ser Gly Glu Gly Ser Gly Gly Phe Trp Asn Arg Gly Ile Ser
130                 135                 140                 145 gct tgt gct gtt tgc gac gga gct gct ccg ata ttc cgt aac aaa cct     2037
Ala Cys Ala Val Cys Asp Gly Ala Ala Pro Ile Phe Arg Asn Lys Pro
                150                 155                 160 ctt gcg gtg atc ggt gga ggc gat tca gca atg gaa gaa gca aac ttt     2085
Leu Ala Val Ile Gly Gly Gly Asp Ser Ala Met Glu Glu Ala Asn Phe
            165                 170                 175 ctt aca aaa tat gga tct aaa gtg tat ata atc cat agg aga gat gct     2133
Leu Thr Lys Tyr Gly Ser Lys Val Tyr Ile Ile His Arg Arg Asp Ala
        180                 185                 190 ttt aga gcg tct aag att atg cag cag cga gct ttg tct aat cct aag     2181
Phe Arg Ala Ser Lys Ile Met Gln Gln Arg Ala Leu Ser Asn Pro Lys
    195                 200                 205 att gat gtg att tgg aac tcg tct gtt gtg gaa gct tat gga gat gga     2229
Ile Asp Val Ile Trp Asn Ser Ser Val Val Glu Ala Tyr Gly Asp Gly
210                 215                 220                 225 gaa aga gat gtg ctt gga gga ttg aaa gtg aag aat gtg gtt acc gga     2277
Glu Arg Asp Val Leu Gly Gly Leu Lys Val Lys Asn Val Val Thr Gly
                230                 235                 240 gat gtt tct gat tta aaa gtt tct gga ttg ttc ttt gct att ggt cat     2325
Asp Val Ser Asp Leu Lys Val Ser Gly Leu Phe Phe Ala Ile Gly His
            245                 250                 255 gag cca gct acc aag ttt ttg gat ggt ggt gtt gag tta gat tcg gat     2373
```

-continued

```
Glu Pro Ala Thr Lys Phe Leu Asp Gly Gly Val Glu Leu Asp Ser Asp
        260                 265                 270 ggt tat gtt gtc acg aag cct ggt act aca cag act agc gtt ccc gga     2421
Gly Tyr Val Val Thr Lys Pro Gly Thr Thr Gln Thr Ser Val Pro Gly
275                 280                 285 gtt ttc gct gcg ggt gat gtt cag gat aag aag tat agg caa gcc atc     2469
Val Phe Ala Ala Gly Asp Val Gln Asp Lys Lys Tyr Arg Gln Ala Ile
290                 295                 300                 305 act gct gca gga act ggg tgc atg gca gct ttg gat gca gag cat tac     2517
Thr Ala Ala Gly Thr Gly Cys Met Ala Ala Leu Asp Ala Glu His Tyr
                310                 315                 320 tta caa gag att gga tct cag caa ggt aag agt gat tgaagcttaa          2563
Leu Gln Glu Ile Gly Ser Gln Gln Gly Lys Ser Asp
            325                 330 taagtatgaa ctaaaatgca tgtaggtgta agagctcatg gagagcatgg aatattgtat   2623
ccgaccatgt aacagtataa taactgagct ccatctcact tcttctatga ataaacaaag   2683
gatgttatga tatattaaca ctctatctat gcaccttatt gttctatgat aaatttcctc   2743
ttattattat aaatcatctg aatcgtgacg gcttatggaa tgcttcaaat agtacaaaaa   2803
caaatgtgta ctataagact ttctaaacaa ttctaacttt agcattgtga acgagacata   2863
agtgttaaga agacataaca attataatgg aagaagtttg tctccattta tatattatat   2923
attacccact tatgtattat attaggatgt taaggagaca taacaattat aaagagagaa   2983
gtttgtatcc atttatatat tatatactac ccatttatat attatactta tccacttatt   3043
taatgtcttt ataaggtttg atccatgata tttctaatat tttagttgat atgtatatga   3103
aagggtacta tttgaactct cttactctgt ataaggttg gatcatcctt aaagtgggtc    3163
tatttaattt tattgcttct tacagataaa aaaaaaatta tgagttggtt tgataaaata   3223
ttgaaggatt taaataataa ataaataata ataacatat aatatatgta taaatttta    3283
ttataatata acatttatct ataaaaaagt aaatattgtc ataaatctat acaatcgttt   3343
agccttgctg gacgactctc aattatttaa acgagagtaa acatatttga cttttggtt    3403
atttaacaaa ttattattta acactatatg aaatttttt tttttatcgg caaggaaata   3463
aaattaaatt aggagggaca atggtgtgtc ccaatcctta tacaaccaac ttccacagga   3523
aggtcaggtc ggggacaaca aaaaaacagg caagggaaat ttttttaattt gggttgtctt  3583
gtttgctgca taatttatgc agtaaaacac tacacataac ccttttagca gtagagcaat   3643
ggttgaccgt gtgcttagct tcttttattt tattttttta tcagcaaaga ataaataaaa   3703
taaaatgaga cacttcaggg atgtttcaac ccttatacaa aaccccaaaa acaagtttcc   3763
tagcacccta ccaactaagg tacc                                          3787
```

<210> SEQ ID NO 14
<211> LENGTH: 333
<212> TYPE: PRT
<213> ORGANISM: Unknown Organism
<220> FEATURE:
<223> OTHER INFORMATION: Description of Unknown Organism: Phaseolin
     promoter-thioredoxin reductase-phaseolin
     terminator

<400> SEQUENCE: 14

```
Met Asn Gly Leu Glu Thr His Asn Thr Arg Leu Cys Ile Val Gly Ser
 1               5                  10                  15

Gly Pro Ala Ala His Thr Ala Ala Ile Tyr Ala Ala Arg Ala Glu Leu
            20                  25                  30
```

Lys Pro Leu Leu Phe Glu Gly Trp Met Ala Asn Asp Ile Ala Pro Gly
            35                  40                  45

Gly Gln Leu Thr Thr Thr Asp Val Glu Asn Phe Pro Gly Phe Pro
        50                  55                  60

Glu Gly Ile Leu Gly Val Glu Leu Thr Asp Lys Phe Arg Lys Gln Ser
 65                  70                  75                  80

Glu Arg Phe Gly Thr Thr Ile Phe Thr Glu Thr Val Thr Lys Val Asp
                85                  90                  95

Phe Ser Ser Lys Pro Phe Lys Leu Phe Thr Asp Ser Lys Ala Ile Leu
            100                 105                 110

Ala Asp Ala Val Ile Leu Ala Thr Gly Ala Val Ala Lys Arg Leu Ser
        115                 120                 125

Phe Val Gly Ser Gly Glu Gly Ser Gly Gly Phe Trp Asn Arg Gly Ile
130                 135                 140

Ser Ala Cys Ala Val Cys Asp Gly Ala Ala Pro Ile Phe Arg Asn Lys
145                 150                 155                 160

Pro Leu Ala Val Ile Gly Gly Gly Asp Ser Ala Met Glu Glu Ala Asn
                165                 170                 175

Phe Leu Thr Lys Tyr Gly Ser Lys Val Tyr Ile Ile His Arg Arg Asp
            180                 185                 190

Ala Phe Arg Ala Ser Lys Ile Met Gln Gln Arg Ala Leu Ser Asn Pro
        195                 200                 205

Lys Ile Asp Val Ile Trp Asn Ser Ser Val Val Glu Ala Tyr Gly Asp
    210                 215                 220

Gly Glu Arg Asp Val Leu Gly Gly Leu Lys Val Lys Asn Val Val Thr
225                 230                 235                 240

Gly Asp Val Ser Asp Leu Lys Val Ser Gly Leu Phe Phe Ala Ile Gly
                245                 250                 255

His Glu Pro Ala Thr Lys Phe Leu Asp Gly Gly Val Glu Leu Asp Ser
            260                 265                 270

Asp Gly Tyr Val Val Thr Lys Pro Gly Thr Thr Gln Thr Ser Val Pro
        275                 280                 285

Gly Val Phe Ala Ala Gly Asp Val Gln Asp Lys Lys Tyr Arg Gln Ala
290                 295                 300

Ile Thr Ala Ala Gly Thr Gly Cys Met Ala Ala Leu Asp Ala Glu His
305                 310                 315                 320

Tyr Leu Gln Glu Ile Gly Ser Gln Gln Gly Lys Ser Asp
                325                 330

<210> SEQ ID NO 15
<211> LENGTH: 4546
<212> TYPE: DNA
<213> ORGANISM: Unknown Organism
<220> FEATURE:
<221> NAME/KEY: CDS
<222> LOCATION: (1555)..(1908)
<221> NAME/KEY: CDS
<222> LOCATION: (2149)..(3312)
<223> OTHER INFORMATION: Description of Unknown Organism: Phaseolin
      promoter-oleosin thioredoxin reductase-phaseolin
      terminator

<400> SEQUENCE: 15
ctgcaggaat tcattgtact cccagtatca ttatagtgaa agttttggct ctctcgccgg      60 tggttttta cctctattta aagggttttt ccacctaaaa attctggtat cattctcact     120
ttacttgtta ctttaatttc tcataatctt tggttgaaat tatcacgctt ccgcacacga    180

```
tatccctaca aattattat ttgttaaaca ttttcaaacc gcataaaatt ttatgaagtc      240
ccgtctatct ttaatgtagt ctaacatttt catattgaaa tatataattt acttaatttt      300
agcgttggta gaaagcataa tgatttattc ttattcttct tcatataaat gtttaatata      360
caatataaac aaattcttta ccttaagaag gatttcccat tttatatttt aaaaatatat      420
ttatcaaata tttttcaacc acgtaaatct cataataata agttgtttca aaagtaataa      480
aatttaactc cataattttt ttattcgact gatcttaaag caacacccag tgacacaact      540 agccatttt ttctttgaat aaaaaaatcc aattatcatt gtatttttt tatacaatga      600 aaatttcacc aaacaatcat ttgtggtatt tctgaagcaa gtcatgttat gcaaaattct      660
ataattccca tttgacacta cggaagtaac tgaagatctg cttttacatg cgagacacat      720
cttctaaagt aattttaata atagttacta tattcaagat ttcatatatc aaatactcaa      780
tattacttct aaaaaattaa ttagatataa ttaaaatatt acttttttaa ttttaagttt      840
aattgttgaa tttgtgacta ttgatttatt attctactat gttaaattg ttttatagat      900 agtttaaagt aaatataagt aatgtagtag agtgttagag tgttacccta aaccataaac      960
tataagattt atggtggact aattttcata tattcttat tgcttttacc ttttcttggt     1020
atgtaagtcc gtaactggaa ttactgtggg ttgccatggc actctgtggt cttttggttc     1080
atgcatggat gcttgcgcaa gaaaaagaca agaacaaag aaaaaagaca aaacagagag     1140
acaaaacgca atcacacaac caactcaaat tagtcactgg ctgatcaaga tcgccgcgtc     1200
catgtatgtc taaatgccat gcaaagcaac acgtgcttaa catgcacttt aaatggctca     1260
cccatctcaa cccacacaca aacacattgc cttttcttc atcatcacca caaccacctg     1320
tatatattca ttctcttccg ccacctcaat ttcttcactt caacacacgt caacctgcat     1380
atgcgtgtca tcccatgccc aaatctccat gcatgttcca accaccttct ctcttatata     1440
ataccctata aatacctctaa tatcactcac ttctttcatc atccatccat ccagagtact     1500
actactctac tactataata ccccaaccca actcatattc aatactactc tact atg      1557
                                                                Met
                                                                 1 gcg gat aca gct aga gga acc cat cac gat atc atc ggc aga gac cag      1605
Ala Asp Thr Ala Arg Gly Thr His His Asp Ile Ile Gly Arg Asp Gln
          5                   10                  15 tac ccg atg atg ggc cga gac cga gac cag tac cag atg tcc gga cga      1653
Tyr Pro Met Met Gly Arg Asp Arg Asp Gln Tyr Gln Met Ser Gly Arg
     20                  25                  30 gga tct gac tac tcc aag tct agg cag att gct aaa gct gca act gct      1701
Gly Ser Asp Tyr Ser Lys Ser Arg Gln Ile Ala Lys Ala Ala Thr Ala
 35                  40                  45 gtc aca gct ggt ggt tcc ctc ctt gtt ctc tcc agc ctt acc ctt gtt      1749
Val Thr Ala Gly Gly Ser Leu Leu Val Leu Ser Ser Leu Thr Leu Val
 50                  55                  60                  65 gga act gtc ata gct ttg act gtt gca aca cct ctg ctc gtt atc ttc      1797
Gly Thr Val Ile Ala Leu Thr Val Ala Thr Pro Leu Leu Val Ile Phe
              70                  75                  80 agc cca atc ctt gtc ccg gct ctc atc aca gtt gca ctc ctc atc acc      1845
Ser Pro Ile Leu Val Pro Ala Leu Ile Thr Val Ala Leu Leu Ile Thr
          85                  90                  95 ggt ttt ctt tcc tct gga ggg ttt ggc att gcc gct ata acc gtt ttc      1893
Gly Phe Leu Ser Ser Gly Gly Phe Gly Ile Ala Ala Ile Thr Val Phe
     100                 105                 110 tct tgg att tac aag taagcacaca tttatcatct tacttcataa ttttgtgcaa     1948
Ser Trp Ile Tyr Lys
     115
```

-continued

```
tatgtgcatg catgtgttga gccagtagct ttggatcaat ttttttggtc gaataacaaa    2008
tgtaacaata agaaattgca aattctaggg aacatttggt taactaaata cgaaatttga    2068
cctagctagc ttgaatgtgt ctgtgtatat catctatata ggtaaaatgc ttggtatgat    2128
acctattgat tgtgaatagg tac gca acg gga gag cac cca cag gga tca gac    2181
                      Tyr Ala Thr Gly Glu His Pro Gln Gly Ser Asp
                          120                 125 aag ttg gac agt gca agg atg aag ttg gga agc aaa gct cag gat ctg      2229
Lys Leu Asp Ser Ala Arg Met Lys Leu Gly Ser Lys Ala Gln Asp Leu
130                 135                 140                 145 aaa gac aga gct cag tac tac gga cag caa cat act ggt ggg gaa cat      2277
Lys Asp Arg Ala Gln Tyr Tyr Gly Gln Gln His Thr Gly Gly Glu His
            150                 155                 160 gac cgt gac cgt act cgt ggt ggc cag cac act acc atg aat ggt ctc      2325
Asp Arg Asp Arg Thr Arg Gly Gly Gln His Thr Thr Met Asn Gly Leu
        165                 170                 175 gaa act cac aac aca agg ctc tgt atc gta gga agt ggc cca gcg gca      2373
Glu Thr His Asn Thr Arg Leu Cys Ile Val Gly Ser Gly Pro Ala Ala
    180                 185                 190 cac acg gcg gcg att tac gca gct agg gct gaa ctt aaa cct ctt ctc      2421
His Thr Ala Ala Ile Tyr Ala Ala Arg Ala Glu Leu Lys Pro Leu Leu
195                 200                 205 ttc gaa gga tgg atg gct aac gac atc gct ccc ggt ggt caa cta aca      2469
Phe Glu Gly Trp Met Ala Asn Asp Ile Ala Pro Gly Gly Gln Leu Thr
210                 215                 220                 225 acc acc acc gac gtc gag aat ttc ccc gga ttt cca gaa ggt att ctc      2517
Thr Thr Thr Asp Val Glu Asn Phe Pro Gly Phe Pro Glu Gly Ile Leu
                230                 235                 240 gga gta gag ctc act gac aaa ttc cgt aaa caa tcg gag cga ttc ggt      2565
Gly Val Glu Leu Thr Asp Lys Phe Arg Lys Gln Ser Glu Arg Phe Gly
            245                 250                 255 act acg ata ttt aca gag acg gtg acg aaa gtc gat ttc tct tcg aaa      2613
Thr Thr Ile Phe Thr Glu Thr Val Thr Lys Val Asp Phe Ser Ser Lys
        260                 265                 270 ccg ttt aag cta ttc aca gat tca aaa gcc att ctc gct gac gct gtg      2661
Pro Phe Lys Leu Phe Thr Asp Ser Lys Ala Ile Leu Ala Asp Ala Val
    275                 280                 285 att ctc gct act gga gct gtg gct aag cgg ctt agc ttc gtt gga tct      2709
Ile Leu Ala Thr Gly Ala Val Ala Lys Arg Leu Ser Phe Val Gly Ser
290                 295                 300                 305 ggt gaa ggt tct gga ggt ttc tgg aac cgt gga atc tcc gct tgt gct      2757
Gly Glu Gly Ser Gly Gly Phe Trp Asn Arg Gly Ile Ser Ala Cys Ala
                310                 315                 320 gtt tgc gac gga gct gct ccg ata ttc cgt aac aaa cct ctt gcg gtg      2805
Val Cys Asp Gly Ala Ala Pro Ile Phe Arg Asn Lys Pro Leu Ala Val
            325                 330                 335 atc ggt gga ggc gat tca gca atg gaa gaa gca aac ttt ctt aca aaa      2853
Ile Gly Gly Gly Asp Ser Ala Met Glu Glu Ala Asn Phe Leu Thr Lys
        340                 345                 350 tat gga tct aaa gtg tat ata atc cat agg aga gat gct ttt aga gcg      2901
Tyr Gly Ser Lys Val Tyr Ile Ile His Arg Arg Asp Ala Phe Arg Ala
    355                 360                 365 tct aag att atg cag cag cga gct ttg tct aat cct aag att gat gtg      2949
Ser Lys Ile Met Gln Gln Arg Ala Leu Ser Asn Pro Lys Ile Asp Val
370                 375                 380                 385 att tgg aac tcg tct gtt gtg gaa gct tat gga gat gga gaa aga gat      2997
Ile Trp Asn Ser Ser Val Val Glu Ala Tyr Gly Asp Gly Glu Arg Asp
                390                 395                 400
```

```
gtg ctt gga gga ttg aaa gtg aag aat gtg gtt acc gga gat gtt tct      3045
Val Leu Gly Gly Leu Lys Val Lys Asn Val Val Thr Gly Asp Val Ser
            405                 410                 415 gat tta aaa gtt tct gga ttg ttc ttt gct att ggt cat gag cca gct      3093
Asp Leu Lys Val Ser Gly Leu Phe Phe Ala Ile Gly His Glu Pro Ala
        420                 425                 430 acc aag ttt ttg gat ggt ggt gtt gag tta gat tcg gat ggt tat gtt      3141
Thr Lys Phe Leu Asp Gly Gly Val Glu Leu Asp Ser Asp Gly Tyr Val
    435                 440                 445 gtc acg aag cct ggt act aca cag act agc gtt ccc gga gtt ttc gct      3189
Val Thr Lys Pro Gly Thr Thr Gln Thr Ser Val Pro Gly Val Phe Ala
450                 455                 460                 465 gcg ggt gat gtt cag gat aag aag tat agg caa gcc atc act gct gca      3237
Ala Gly Asp Val Gln Asp Lys Lys Tyr Arg Gln Ala Ile Thr Ala Ala
                470                 475                 480 gga act ggg tgc atg gca gct ttg gat gca gag cat tac tta caa gag      3285
Gly Thr Gly Cys Met Ala Ala Leu Asp Ala Glu His Tyr Leu Gln Glu
            485                 490                 495 att gga tct cag caa ggt aag agt gat tgaagcttaa taagtatgaa            3332
Ile Gly Ser Gln Gln Gly Lys Ser Asp
            500                 505 ctaaaatgca tgtaggtgta agagctcatg gagagcatgg aatattgtat ccgaccatgt    3392
aacagtataa taactgagct ccatctcact tcttctatga ataaacaaag gatgttatga    3452
tatattaaca ctctatctat gcaccttatt gttctatgat aaatttcctc ttattattat    3512
aaatcatctg aatcgtgacg gcttatggaa tgcttcaaat agtacaaaaa caaatgtgta    3572
ctataagact ttctaaacaa ttctaacttt agcattgtga acgagacata agtgttaaga    3632
agacataaca attataatgg aagaagtttg tctccattta tatattatat attacccact    3692
tatgtattat attaggatgt taaggagaca taacaattat aaagagagaa gtttgtatcc    3752
atttatatat tatatactac ccatttatat attatactta tccacttatt taatgtcttt    3812
ataaggtttg atccatgata tttctaatat tttagttgat atgtatatga aagggtacta    3872
tttgaactct cttactctgt ataaaggttg gatcatcctt aaagtgggtc tatttaattt    3932
tattgcttct tacagataaa aaaaaaatta tgagttggtt tgataaaata ttgaaggatt    3992
taaaataata ataaataata aataacatat aatatatgta tataaattta ttataatata    4052
acatttatct ataaaaaagt aaatattgtc ataaatctat acaatcgttt agccttgctg    4112
gacgactctc aattatttaa acgagagtaa acatatttga cttttggtt atttaacaaa     4172 ttattattta acactatatg aaattttttt tttttatcgg caaggaaata aaattaaatt    4232
aggagggaca atggtgtgtc ccaatcctta tacaaccaac ttccacagga aggtcaggtc    4292
ggggacaaca aaaaaacagg caagggaaat tttttaattt gggttgtctt gtttgctgca    4352
taatttatgc agtaaaacac tacacataac ccttttagca gtagagcaat ggttgaccgt    4412
gtgcttagct tcttttattt tatttttta tcagcaaaga ataaataaaa taaaatgaga     4472
cacttcaggg atgtttcaac ccttatacaa aaccccaaaa acaagtttcc tagcacccta    4532
ccaactaagg tacc                                                      4546

<210> SEQ ID NO 16
<211> LENGTH: 118
<212> TYPE: PRT
<213> ORGANISM: Unknown Organism
<220> FEATURE:
<223> OTHER INFORMATION: Description of Unknown Organism: Phaseolin
      promoter-oleosin thioredoxin reductase-phaseolin
      terminator
```

<400> SEQUENCE: 16

```
Met Ala Asp Thr Ala Arg Gly Thr His His Asp Ile Ile Gly Arg Asp
 1               5                  10                  15
Gln Tyr Pro Met Met Gly Arg Asp Arg Asp Gln Tyr Gln Met Ser Gly
            20                  25                  30
Arg Gly Ser Asp Tyr Ser Lys Ser Arg Gln Ile Ala Lys Ala Ala Thr
        35                  40                  45
Ala Val Thr Ala Gly Gly Ser Leu Leu Val Leu Ser Ser Leu Thr Leu
    50                  55                  60
Val Gly Thr Val Ile Ala Leu Thr Val Ala Thr Pro Leu Leu Val Ile
65                  70                  75                  80
Phe Ser Pro Ile Leu Val Pro Ala Leu Ile Thr Val Ala Leu Leu Ile
                85                  90                  95
Thr Gly Phe Leu Ser Ser Gly Gly Phe Gly Ile Ala Ala Ile Thr Val
            100                 105                 110
Phe Ser Trp Ile Tyr Lys
        115
```

<210> SEQ ID NO 17
<211> LENGTH: 388
<212> TYPE: PRT
<213> ORGANISM: Unknown Organism
<220> FEATURE:
<223> OTHER INFORMATION: Description of Unknown Organism: Phaseolin promoter-oleosin thioredoxin reductase-phaseolin terminator

<400> SEQUENCE: 17

```
Tyr Ala Thr Gly Glu His Pro Gln Gly Ser Asp Lys Leu Asp Ser Ala
 1               5                  10                  15
Arg Met Lys Leu Gly Ser Lys Ala Gln Asp Leu Lys Asp Arg Ala Gln
            20                  25                  30
Tyr Tyr Gly Gln Gln His Thr Gly Gly Glu His Asp Arg Asp Arg Thr
        35                  40                  45
Arg Gly Gly Gln His Thr Thr Met Asn Gly Leu Glu Thr His Asn Thr
    50                  55                  60
Arg Leu Cys Ile Val Gly Ser Gly Pro Ala Ala His Thr Ala Ala Ile
65                  70                  75                  80
Tyr Ala Ala Arg Ala Glu Leu Lys Pro Leu Leu Phe Glu Gly Trp Met
                85                  90                  95
Ala Asn Asp Ile Ala Pro Gly Gly Gln Leu Thr Thr Thr Thr Asp Val
            100                 105                 110
Glu Asn Phe Pro Gly Phe Pro Glu Gly Ile Leu Gly Val Glu Leu Thr
        115                 120                 125
Asp Lys Phe Arg Lys Gln Ser Glu Arg Phe Gly Thr Thr Ile Phe Thr
130                 135                 140
Glu Thr Val Thr Lys Val Asp Phe Ser Ser Lys Pro Phe Lys Leu Phe
145                 150                 155                 160
Thr Asp Ser Lys Ala Ile Leu Ala Asp Ala Val Ile Leu Ala Thr Gly
                165                 170                 175
Ala Val Ala Lys Arg Leu Ser Phe Val Gly Ser Gly Glu Gly Ser Gly
            180                 185                 190
Gly Phe Trp Asn Arg Gly Ile Ser Ala Cys Ala Val Cys Asp Gly Ala
        195                 200                 205
Ala Pro Ile Phe Arg Asn Lys Pro Leu Ala Val Ile Gly Gly Gly Asp
```

-continued

```
                210                 215                 220
Ser Ala Met Glu Glu Ala Asn Phe Leu Thr Lys Tyr Gly Ser Lys Val
225                 230                 235                 240

Tyr Ile Ile His Arg Arg Asp Ala Phe Arg Ala Ser Lys Ile Met Gln
                245                 250                 255

Gln Arg Ala Leu Ser Asn Pro Lys Ile Asp Val Ile Trp Asn Ser Ser
                260                 265                 270

Val Val Glu Ala Tyr Gly Asp Gly Glu Arg Asp Val Leu Gly Gly Leu
                275                 280                 285

Lys Val Lys Asn Val Val Thr Gly Asp Val Ser Asp Leu Lys Val Ser
290                 295                 300

Gly Leu Phe Phe Ala Ile Gly His Glu Pro Ala Thr Lys Phe Leu Asp
305                 310                 315                 320

Gly Gly Val Glu Leu Asp Ser Asp Gly Tyr Val Val Thr Lys Pro Gly
                325                 330                 335

Thr Thr Gln Thr Ser Val Pro Gly Val Phe Ala Ala Gly Asp Val Gln
                340                 345                 350

Asp Lys Lys Tyr Arg Gln Ala Ile Thr Ala Ala Gly Thr Gly Cys Met
                355                 360                 365

Ala Ala Leu Asp Ala Glu His Tyr Leu Gln Glu Ile Gly Ser Gln Gln
                370                 375                 380

Gly Lys Ser Asp
385
```

```
<210> SEQ ID NO 18
<211> LENGTH: 4545
<212> TYPE: DNA
<213> ORGANISM: Unknown Organism
<220> FEATURE:
<221> NAME/KEY: CDS
<222> LOCATION: (1555)..(2907)
<221> NAME/KEY: CDS
<222> LOCATION: (3148)..(3312)
<223> OTHER INFORMATION: Description of Unknown Organism: Phaseolin
      promoter-thioredoxin reductase oleosin-phaseolin
      terminator

<400> SEQUENCE: 18
ctgcaggaat tcattgtact cccagtatca ttatagtgaa agttttggct ctctcgccgg      60 tggttttta cctctatta aaggggtttt ccacctaaaa attctggtat cattctcact      120
ttacttgtta ctttaatttc tcataatctt tggttgaaat tatcacgctt ccgcacacga      180
tatccctaca aatttattat ttgttaaaca ttttcaaacc gcataaaatt ttatgaagtc     240
ccgtctatct ttaatgtagt ctaacattt catattgaaa tatataattt acttaatttt     300
agcgttggta gaaagcataa tgatttattc ttattcttct tcatataaat gtttaatata     360
caatataaac aaattcttta ccttaagaag gatttcccat tttatatttt aaaaatatat    420
ttatcaaata ttttcaacc acgtaaatct cataataata agttgtttca aaagtaataa    480
aatttaactc cataattttt ttattcgact gatcttaaag caacacccag tgacacaact    540
agccattttt ttctttgaat aaaaaaatcc aattatcatt gtattttttt tatacaatga    600
aaatttcacc aaacaatcat ttgtggtatt tctgaagcaa gtcatgttat gcaaaattct    660
ataattccca tttgacacta cggaagtaac tgaagatctg cttttacatg cgagacacat    720
cttctaaagt aatttaata atagttacta tattcaagat ttcatatatc aaatactcaa    780
tattacttct aaaaaattaa ttagatataa ttaaatatt actttttaa ttttaagttt    840
```

```
aattgttgaa tttgtgacta ttgatttatt attctactat gtttaaattg ttttatagat      900
agtttaaagt aaatataagt aatgtagtag agtgttagag tgttacccta aaccataaac      960
tataagattt atggtggact aatttttcata tatttcttat tgcttttacc ttttcttggt    1020
atgtaagtcc gtaactggaa ttactgtggg ttgccatggc actctgtggt cttttggttc    1080
atgcatggat gcttgcgcaa gaaaaagaca agaacaaag aaaaagaca aaacagagag      1140 acaaaacgca atcacacaac caactcaaat tagtcactgg ctgatcaaga tcgccgcgtc    1200
catgtatgtc taaatgccat gcaaagcaac acgtgcttaa catgcacttt aaatggctca    1260
cccatctcaa cccacacaca aacacattgc cttttcttc atcatcacca caaccacctg    1320
tatatattca ttctcttccg ccacctcaat ttcttcactt caacacacgt caacctgcat    1380
atgcgtgtca tcccatgccc aaatctccat gcatgttcca accaccttct ctcttatata    1440
atacctataa atacctctaa tatcactcac ttctttcatc atccatccat ccagagtact    1500
actactctac tactataata ccccaaccca actcatattc aatactactc tact atg      1557
                                                                  Met
                                                                   1 aat ggt ctc gaa act cac aac aca agg ctc tgt atc gta gga agt ggc      1605
Asn Gly Leu Glu Thr His Asn Thr Arg Leu Cys Ile Val Gly Ser Gly
          5                  10                  15 cca gcg gca cac acg gcg gcg att tac gca gct agg gct gaa ctt aaa      1653
Pro Ala Ala His Thr Ala Ala Ile Tyr Ala Ala Arg Ala Glu Leu Lys
         20                  25                  30 cct ctt ctc ttc gaa gga tgg atg gct aac gac atc gct ccc ggt ggt      1701
Pro Leu Leu Phe Glu Gly Trp Met Ala Asn Asp Ile Ala Pro Gly Gly
     35                  40                  45 caa cta aca acc acc acc gac gtc gag aat ttc ccc gga ttt cca gaa      1749
Gln Leu Thr Thr Thr Thr Asp Val Glu Asn Phe Pro Gly Phe Pro Glu
 50                  55                  60                  65 ggt att ctc gga gta gag ctc act gac aaa ttc cgt aaa caa tcg gag      1797
Gly Ile Leu Gly Val Glu Leu Thr Asp Lys Phe Arg Lys Gln Ser Glu
                 70                  75                  80 cga ttc ggt act acg ata ttt aca gag acg gtg acg aaa gtc gat ttc      1845
Arg Phe Gly Thr Thr Ile Phe Thr Glu Thr Val Thr Lys Val Asp Phe
             85                  90                  95 tct tcg aaa ccg ttt aag cta ttc aca gat tca aaa gcc att ctc gct      1893
Ser Ser Lys Pro Phe Lys Leu Phe Thr Asp Ser Lys Ala Ile Leu Ala
        100                 105                 110 gac gct gtg att ctc gct act gga gct gtg gct aag cgg ctt agc ttc      1941
Asp Ala Val Ile Leu Ala Thr Gly Ala Val Ala Lys Arg Leu Ser Phe
    115                 120                 125 gtt gga tct ggt gaa ggt tct gga ggt ttc tgg aac cgt gga atc tcc      1989
Val Gly Ser Gly Glu Gly Ser Gly Gly Phe Trp Asn Arg Gly Ile Ser
130                 135                 140                 145 gct tgt gct gtt tgc gac gga gct gct ccg ata ttc cgt aac aaa cct      2037
Ala Cys Ala Val Cys Asp Gly Ala Ala Pro Ile Phe Arg Asn Lys Pro
                150                 155                 160 ctt gcg gtg atc ggt gga ggc gat tca gca atg gaa gaa gca aac ttt      2085
Leu Ala Val Ile Gly Gly Gly Asp Ser Ala Met Glu Glu Ala Asn Phe
            165                 170                 175 ctt aca aaa tat gga tct aaa gtg tat ata atc cat agg aga gat gct      2133
Leu Thr Lys Tyr Gly Ser Lys Val Tyr Ile Ile His Arg Arg Asp Ala
        180                 185                 190 ttt aga gcg tct aag att atg cag cag cga gct ttg tct aat cct aag      2181
Phe Arg Ala Ser Lys Ile Met Gln Gln Arg Ala Leu Ser Asn Pro Lys
    195                 200                 205 att gat gtg att tgg aac tcg tct gtt gtg gaa gct tat gga gat gga      2229
Ile Asp Val Ile Trp Asn Ser Ser Val Val Glu Ala Tyr Gly Asp Gly
```

```
                Ile Asp Val Ile Trp Asn Ser Ser Val Val Glu Ala Tyr Gly Asp Gly
                210                 215                 220                 225 gaa aga gat gtg ctt gga gga ttg aaa gtg aag aat gtg gtt acc gga           2277
Glu Arg Asp Val Leu Gly Gly Leu Lys Val Lys Asn Val Val Thr Gly
                230                 235                 240 gat gtt tct gat tta aaa gtt tct gga ttg ttc ttt gct att ggt cat           2325
Asp Val Ser Asp Leu Lys Val Ser Gly Leu Phe Phe Ala Ile Gly His
            245                 250                 255 gag cca gct acc aag ttt ttg gat ggt ggt gtt gag tta gat tcg gat           2373
Glu Pro Ala Thr Lys Phe Leu Asp Gly Gly Val Glu Leu Asp Ser Asp
        260                 265                 270 ggt tat gtt gtc acg aag cct ggt act aca cag act agc gtt ccc gga           2421
Gly Tyr Val Val Thr Lys Pro Gly Thr Thr Gln Thr Ser Val Pro Gly
    275                 280                 285 gtt ttc gct gcg ggt gat gtt cag gat aag aag tat agg caa gcc atc           2469
Val Phe Ala Ala Gly Asp Val Gln Asp Lys Lys Tyr Arg Gln Ala Ile
290                 295                 300                 305 act gct gca gga act ggg tgc atg gca gct ttg gat gca gag cat tac           2517
Thr Ala Ala Gly Thr Gly Cys Met Ala Ala Leu Asp Ala Glu His Tyr
                310                 315                 320 tta caa gag att gga tct cag caa ggt aag agt gat atg gcg gat aca           2565
Leu Gln Glu Ile Gly Ser Gln Gln Gly Lys Ser Asp Met Ala Asp Thr
            325                 330                 335 gct aga gga acc cat cac gat atc atc ggc aga gac cag tac ccg atg           2613
Ala Arg Gly Thr His His Asp Ile Ile Gly Arg Asp Gln Tyr Pro Met
        340                 345                 350 atg ggc cga gac cga gac cag tac cag atg tcc gga cga gga tct gac           2661
Met Gly Arg Asp Arg Asp Gln Tyr Gln Met Ser Gly Arg Gly Ser Asp
    355                 360                 365 tac tcc aag tct agg cag att gct aaa gct gca act gct gtc aca gct           2709
Tyr Ser Lys Ser Arg Gln Ile Ala Lys Ala Ala Thr Ala Val Thr Ala
370                 375                 380                 385 ggt ggt tcc ctc ctt gtt ctc tcc agc ctt acc ctt gtt gga act gtc           2757
Gly Gly Ser Leu Leu Val Leu Ser Ser Leu Thr Leu Val Gly Thr Val
                390                 395                 400 ata gct ttg act gtt gca aca cct ctg ctc gtt atc ttc agc cca atc           2805
Ile Ala Leu Thr Val Ala Thr Pro Leu Leu Val Ile Phe Ser Pro Ile
            405                 410                 415 ctt gtc ccg gct ctc atc aca gtt gca ctc ctc atc acc ggt ttt ctt           2853
Leu Val Pro Ala Leu Ile Thr Val Ala Leu Leu Ile Thr Gly Phe Leu
        420                 425                 430 tcc tct gga ggg ttt ggc att gcc gct ata acc gtt ttc tct tgg att           2901
Ser Ser Gly Gly Phe Gly Ile Ala Ala Ile Thr Val Phe Ser Trp Ile
    435                 440                 445 tac aag taagcacaca tttatcatct tacttcataa ttttgtgcaa tatgtgcatg            2957
Tyr Lys
450 catgtgttga gccagtagct ttggatcaat ttttttggtc gaataacaaa tgtaacaata         3017 agaaattgca aattctaggg aacatttggt taactaaata cgaaatttga cctagctagc         3077 ttgaatgtgt ctgtgtatat catctatata ggtaaaatgc ttggtatgat acctattgat         3137 tgtgaatagg tac gca acg gga gag cac cca cag gga tca gac aag ttg            3186
            Tyr Ala Thr Gly Glu His Pro Gln Gly Ser Asp Lys Leu
                        455                 460 gac agt gca agg atg aag ttg gga agc aaa gct cag gat ctg aaa gac           3234
Asp Ser Ala Arg Met Lys Leu Gly Ser Lys Ala Gln Asp Leu Lys Asp
465                 470                 475                 480 aga gct cag tac tac gga cag caa cat act ggt ggg gaa cat gac cgt           3282
Arg Ala Gln Tyr Tyr Gly Gln Gln His Thr Gly Gly Glu His Asp Arg
```

-continued

```
                485                 490                 495
gac cgt act cgt ggt ggc cag cac act act taagcttaat aagtatgaac      3332
Asp Arg Thr Arg Gly Gly Gln His Thr Thr
            500                 505 taaaatgcat gtaggtgtaa gagctcatgg agagcatgga atattgtatc cgaccatgta  3392
acagtataat aactgagctc catctcactt cttctatgaa taaacaaagg atgttatgat  3452
atattaacac tctatctatg caccttattg ttctatgata aatttcctct tattattata  3512
aatcatctga atcgtgacgg cttatggaat gcttcaaata gtacaaaaac aaatgtgtac  3572
tataagactt tctaaacaat tctaacttta gcattgtgaa cgagacataa gtgttaagaa  3632
gacataacaa ttataatgga agaagtttgt ctccatttat atattatata ttacccactt  3692
atgtattata ttaggatgtt aaggagacat aacaattata agagagaag tttgtatcca   3752 tttatatatt atatactacc catttatata ttatacttat ccacttatttt aatgtcttta  3812 taaggtttga tccatgatat ttctaatatt ttagttgata tgtatatgaa agggtactat  3872
ttgaactctc ttactctgta taaaggttgg atcatcctta aagtgggtct atttaatttt  3932
attgcttctt acagataaaa aaaaaattat gagttggttt gataaaatat tgaaggattt  3992
aaaataataa taaataataa ataacatata atatatgtat ataaatttat tataatataa  4052
catttatcta taaaaagta aatattgtca taaatctata caatcgttta gccttgctgg   4112
acgactctca attatttaaa cgagagtaaa catatttgac ttttttggtta tttaacaaat  4172 tattatttaa cactatatga aatttttttt tttatcggc aaggaaataa aattaaatta   4232
ggagggacaa tggtgtgtcc caatccttat acaaccaact tccacaggaa ggtcaggtcg  4292
gggacaacaa aaaaacaggc aagggaaatt ttttaatttg ggttgtcttg tttgctgcat  4352
aatttatgca gtaaaacact acacataacc cttttagcag tagagcaatg gttgaccgtg  4412
tgcttagctt ctttttatttt atttttttat cagcaaagaa taaataaaat aaaatgagac  4472
acttcaggga tgtttcaacc cttatacaaa accccaaaaa caagtttcct agcaccctac  4532
caactaaggt acc                                                     4545
```

<210> SEQ ID NO 19
<211> LENGTH: 451
<212> TYPE: PRT
<213> ORGANISM: Unknown Organism
<220> FEATURE:
<223> OTHER INFORMATION: Description of Unknown Organism: Phaseolin promoter-thioredoxin reductase oleosin-phaseolin terminator

<400> SEQUENCE: 19

```
Met Asn Gly Leu Glu Thr His Asn Thr Arg Leu Cys Ile Val Gly Ser
  1               5                  10                  15

Gly Pro Ala Ala His Thr Ala Ala Ile Tyr Ala Ala Arg Ala Glu Leu
             20                  25                  30

Lys Pro Leu Leu Phe Glu Gly Trp Met Ala Asn Asp Ile Ala Pro Gly
         35                  40                  45

Gly Gln Leu Thr Thr Thr Thr Asp Val Glu Asn Phe Pro Gly Phe Pro
     50                  55                  60

Glu Gly Ile Leu Gly Val Glu Leu Thr Asp Lys Phe Arg Lys Gln Ser
 65                  70                  75                  80

Glu Arg Phe Gly Thr Thr Ile Phe Thr Glu Thr Val Thr Lys Val Asp
                 85                  90                  95

Phe Ser Ser Lys Pro Phe Lys Leu Phe Thr Asp Ser Lys Ala Ile Leu
```

```
                100                 105                 110
Ala Asp Ala Val Ile Leu Ala Thr Gly Ala Val Ala Lys Arg Leu Ser
            115                 120                 125

Phe Val Gly Ser Gly Glu Gly Ser Gly Gly Phe Trp Asn Arg Gly Ile
    130                 135                 140

Ser Ala Cys Ala Val Cys Asp Gly Ala Ala Pro Ile Phe Arg Asn Lys
145                 150                 155                 160

Pro Leu Ala Val Ile Gly Gly Asp Ser Ala Met Glu Glu Ala Asn
                165                 170                 175

Phe Leu Thr Lys Tyr Gly Ser Lys Val Tyr Ile Ile His Arg Arg Asp
            180                 185                 190

Ala Phe Arg Ala Ser Lys Ile Met Gln Gln Arg Ala Leu Ser Asn Pro
        195                 200                 205

Lys Ile Asp Val Ile Trp Asn Ser Ser Val Val Glu Ala Tyr Gly Asp
    210                 215                 220

Gly Glu Arg Asp Val Leu Gly Gly Leu Lys Val Lys Asn Val Val Thr
225                 230                 235                 240

Gly Asp Val Ser Asp Leu Lys Val Ser Gly Leu Phe Phe Ala Ile Gly
                245                 250                 255

His Glu Pro Ala Thr Lys Phe Leu Asp Gly Gly Val Glu Leu Asp Ser
            260                 265                 270

Asp Gly Tyr Val Val Thr Lys Pro Gly Thr Thr Gln Thr Ser Val Pro
        275                 280                 285

Gly Val Phe Ala Ala Gly Asp Val Gln Asp Lys Lys Tyr Arg Gln Ala
    290                 295                 300

Ile Thr Ala Ala Gly Thr Gly Cys Met Ala Ala Leu Asp Ala Glu His
305                 310                 315                 320

Tyr Leu Gln Glu Ile Gly Ser Gln Gly Lys Ser Asp Met Ala Asp
                325                 330                 335

Thr Ala Arg Gly Thr His His Asp Ile Ile Gly Arg Asp Gln Tyr Pro
            340                 345                 350

Met Met Gly Arg Asp Arg Asp Gln Tyr Gln Met Ser Gly Arg Gly Ser
        355                 360                 365

Asp Tyr Ser Lys Ser Arg Gln Ile Ala Lys Ala Ala Thr Ala Val Thr
    370                 375                 380

Ala Gly Gly Ser Leu Leu Val Leu Ser Ser Leu Thr Leu Val Gly Thr
385                 390                 395                 400

Val Ile Ala Leu Thr Val Ala Thr Pro Leu Leu Val Ile Phe Ser Pro
                405                 410                 415

Ile Leu Val Pro Ala Leu Ile Thr Val Ala Leu Leu Ile Thr Gly Phe
            420                 425                 430

Leu Ser Ser Gly Gly Phe Gly Ile Ala Ala Ile Thr Val Phe Ser Trp
        435                 440                 445

Ile Tyr Lys
    450

<210> SEQ ID NO 20
<211> LENGTH: 55
<212> TYPE: PRT
<213> ORGANISM: Unknown Organism
<220> FEATURE:
<223> OTHER INFORMATION: Description of Unknown Organism: Phaseolin
      promoter-thioredoxin reductase oleosin-phaseolin
      terminator

<400> SEQUENCE: 20
```

-continued

```
Tyr Ala Thr Gly Glu His Pro Gln Gly Ser Asp Lys Leu Asp Ser Ala
 1               5                  10                  15

Arg Met Lys Leu Gly Ser Lys Ala Gln Asp Leu Lys Asp Arg Ala Gln
             20                  25                  30

Tyr Tyr Gly Gln Gln His Thr Gly Gly Glu His Asp Arg Asp Arg Thr
         35                  40                  45

Arg Gly Gly Gln His Thr Thr
     50                  55

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 21
taccatggct tcggaagaag ga                                          22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 22
gaaagcttaa gccaagtgtt tg                                          22

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 23
ggccagcaca ctaccatgaa tggtctcgaa actcac                           36

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 24
ttaagcttca atcactctta ccttgctg                                    28
```

We claim:

1. A method for the preparation of an emulsion formulation, comprising:
   (a) introducing into a plant cell a chimeric nucleic acid sequence comprising
      (1) a first regulatory nucleic acid sequence, that regulates transcription in said cell, operatively linked to
      (2) a coding nucleic acid sequence that codes for a recombinant fusion polypeptide, said coding nucleic sequence comprising
         (i) a first nucleic acid sequence, encoding at least the central domain of an oil body protein to provide targeting to an oil body, linked in reading frame to
         (ii) a second nucleic acid sequence, encoding a thioredoxin or thioredoxin reductase, operatively linked to
      (3) a second regulatory nucleic acid sequence that regulates termination of transcription in said plant cell, such that said recombinant fusion polypeptide comprises an oil body protein and thioredoxin or thioredoxin reductase;
   wherein said plant cell is selected from the group consisting of an almond cell, an anise cell, an avocado cell, a beach nut cell, a borage cell, a Brazil nut cell, a candle nut cell, a cashew nut cell, a castor cell, a coconut cell, a coriander cell, a cotton cell, a crambe cell, a croton cell, a *Cuphea* cell, a *Euphorbia* cell, a *Dimorphoteca* cell, a false flax cell, a fennel cell, a groundnut cell, a hazelnut cell, a hemp cell, a honesty plant cell, a jojoba cell, a kapok fruit cell, a kukui nut cell, a *Lesquerella* cell, a linseed cell, a macademia nut cell, a maize cell, a meadow foam cell, a mustard cell, a oil palm cell, a oiticia cell, a paw paw cell, a pecan cell, a perilla cell, a physic nut cell, pilinut cell, a pine nut cell, a pistachio cell, a poppy seed cell, a rapeseed cell, a safflower cell, a sesame seed cell, a soybean cell, a squash cell, a sal tree cell, a Stokes a aster cell, a sunflower cell, a tukuma cell, a tung nut cell, and a veronia cell;

(b) growing said plant cell to express said recombinant fusion polypeptide in a progeny plant cell comprising oil bodies;

(c) isolating said oil bodies from said progeny plant cell expressing said recombinant fusion polypeptide;

(d) washing said oil bodies to obtain a washed oil body preparation comprised of substantially intact oil bodies that comprise said recombinant fusion polypeptide; and (e) formulating said washed oil body preparation comprising substantially intact oil bodies into an emulsion.

2. A method according to claim 1, wherein said oil body protein is an oleosin or a caleosin.

3. A method according to claim 1, wherein the oil bodies are obtained from plant seeds.

4. A method according to claim 1, wherein said thioredoxin and thioredoxin reductase in said emulsion chemically reduces a target.

5. A method for the preparation of an emulsion formulation, comprising:

(a) providing oil bodies from a plant cell comprising a recombinant nucleic acid encoding a thioredoxin or thioredoxin reductase, wherein said plant cell is selected from the group consisting of an almond cell, an anise cell, an avocado cell, a beach nut cell, a borage cell, a Brazil nut cell, a candle nut cell, a cashew nut cell, a castor cell, a coconut cell, a coriander cell, a cotton cell, a crambe cell, a croton cell, a *Cuphea* cell, a *Euphorbia* cell, a *Dimorphoteca* cell, a false flax cell, a fennel cell, a groundnut cell, a hazelnut cell, a hemp cell, a honesty plant cell, a jojoba cell, a kapok fruit cell, a kukui nut cell, a *Lesquerella* cell, a linseed cell, a macademia nut cell, a maize cell, a meadow foam cell, a mustard cell, a oil palm cell, a oiticia cell, a paw paw cell, a pecan cell, a perilla cell, a physic nut cell, pilinut cell, a pine nut cell, a pistachio cell, a poppy seed cell, a rapeseed cell, a safflower cell, a sesame seed cell, a soybean cell, a squash cell, a sal tree cell, a Stokes a aster cell, a sunflower cell, a tukuma cell, a tung nut cell, and a veronia cell;

(b) washing said oil bodies to obtain a washed oil body preparation comprised of substantially intact oil bodies; and (c) formulating said washed oil body preparation comprising substantially intact oil bodies into an emulsion.

6. A method for the preparation of an emulsion formulation, comprising;

(a) obtaining a washed oil body preparation comprising substantially intact oil bodies obtained from a plant cell comprising a recombinant nucleic acid encoding a thioredoxin or thioredoxin reductase, wherein said plant cell is selected from the group consisting of an almond cell, an anise cell, an avocado cell, a beach nut cell, a borage cell, a Brazil nut cell, a candle nut cell, a cashew nut cell, a castor cell, a coconut cell, a coriander cell, a cotton cell, a crambe cell, a croton cell, a *Cuphea* cell, a *Euphorbia* cell, a *Dimorphoteca* cell, a false flax cell, a fennel cell, a groundnut cell, a hazelnut cell, a hemp cell, a honesty plant cell, a jojoba cell, a kapok fruit cell, a kukui nut cell, a *Lesquerella* cell, a linseed cell, a macademia nut cell, a maize cell, a meadow foam cell, a mustard cell, a oil palm cell, a oiticia cell, a paw paw cell, a pecan cell, a perilla cell, a physic nut cell, pilinut cell, a pine nut cell, a pistachio cell, a poppy seed cell, a rapeseed cell, a safflower cell, a sesame seed cell, a soybean cell, a squash cell, a sal tree cell, a Stokes a aster cell, a sunflower cell, a tukuma cell, a tung nut cell, and a veronia cell; and (b) formulating said washed oil body preparation comprising substantially intact oil bodies into an emulsion.

\* \* \* \* \*

UNITED STATES PATENT AND TRADEMARK OFFICE
CERTIFICATE OF CORRECTION

PATENT NO. : 7,585,645 B2 Page 1 of 1
APPLICATION NO. : 09/897898
DATED : September 8, 2009
INVENTOR(S) : Deckers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 111 days.

Signed and Sealed this

Fourteenth Day of September, 2010

David J. Kappos
*Director of the United States Patent and Trademark Office*